(12) United States Patent
Turtle et al.

(10) Patent No.: US 8,703,795 B2
(45) Date of Patent: Apr. 22, 2014

(54) THIENOPYRIDINE COMPOUNDS, AND METHODS OF USE THEREOF

(75) Inventors: Eric D. Turtle, Belmont, CA (US); Lee A. Flippin, Woodside, CA (US); Michael P. Arend, Foster City, CA (US); Heng Cheng, Millbrae, CA (US)

(73) Assignee: Fibrogen, Inc., San Francisco, CA (US)

( * ) Notice: Subject to any disclaimer, the term of this patent is extended or adjusted under 35 U.S.C. 154(b) by 1877 days.

(21) Appl. No.: 11/367,969

(22) Filed: Mar. 2, 2006

(65) Prior Publication Data

US 2006/0199836 A1    Sep. 7, 2006

Related U.S. Application Data

(60) Provisional application No. 60/658,131, filed on Mar. 2, 2005.

(51) Int. Cl.
*A61K 31/4365* (2006.01)
*C07D 495/04* (2006.01)

(52) U.S. Cl.
USPC .......................................... 514/301; 546/114

(58) Field of Classification Search
USPC .......................................... 546/114; 514/301
See application file for complete search history.

(56) References Cited

U.S. PATENT DOCUMENTS 5,658,933 A    8/1997   Weldman et al.

FOREIGN PATENT DOCUMENTS

| EP | 650961 | 10/1994 |
|----|--------|---------|
| EP | 661269 | 12/1994 |
| WO | WO 03/010141 | 2/2003 |
| WO | WO 03/014377 | 2/2003 |
| WO | WO 03/053997 | 7/2003 |
| WO | WO 2004/108121 | 12/2004 |
| WO | WO 2004/108681 | 12/2004 |

OTHER PUBLICATIONS

Balant et al., "Metabolic Considerations, etc.," in Manfred ed. Burger's Medicinal Chemistry and Drug Discovery, 5rh ed. vol. 1: Principles and Practice, John Wiley & Sons, Inc., 1995.*
Testa, "Prodrug Research, etc.," Biochemical Pharmacology 68 (2004) 2097-2106.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*

* cited by examiner

*Primary Examiner* — Patricia L Morris
(74) *Attorney, Agent, or Firm* — Sheppard, Mullin, Richter & Hampton LLP

(57) ABSTRACT

The present invention relates to novel compounds capable of modulating the stability and/or activity of hypoxia inducible factor (HIF).

14 Claims, No Drawings

THIENOPYRIDINE COMPOUNDS, AND METHODS OF USE THEREOF

CROSS REFERENCE TO RELATED APPLICATIONS

This application claims priority under 35 U.S.C. §119(e) of U.S. Provisional Application No. 60/658,131 filed on Mar. 2, 2005, which is hereby incorporated by reference in its entirety.

BACKGROUND OF THE INVENTION

1. Field of the Invention

This invention relates to novel compounds capable of modulating the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang, et al., (1996) J. Biol. Chem., 271:17771-17778; Iliopoulus, et al., (1996) Proc. Natl. Acad. Sci. USA, 93:10595-10599; Maxwell, et al., (1999), Nature, 399:271-275; Sutter, et al., (2000) Proc. Natl. Acad. Sci. USA, 97:4748-4753; Cockman, et al., (2000) J. Biol. Chem., 275:25733-25741; and Tanimoto, et al., (2000) EMBO. J. 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as myocardial acute ischemia, and early infarction, pulmonary hypertension, inflammation, and anemia.

HIFα levels are also increased by a number of factors that mimic hypoxia, including iron chelators such as desferrioxamine (DFO), and divalent metal salts such as $CoCl_2$. Additionally, compounds originally identified as inhibitors of procollagen prolyl hydroxylase enzymes have been found to stabilize HIFα. Examples of such compounds can be found, e.g., in Majamaa et al. (1984) Eur J Biochem 138:239-245; Majamaa et al. (1985) Biochem J 229:127-133; Kivirikko, and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19):812-815; and Franklin et al. (2001) Biochem J 353:333-338. Additionally, compounds that stabilize HIFα have been described in, e.g., International Publication Nos. WO 03/049686, WO 02/074981, WO 03/080566, and WO 2004/108681.

There remains a need for compounds that are effective in the prevention of disorders associated with HIF, including anemia, and tissue damage caused by ischemia that occurs due to, e.g., atherosclerosis, diabetes, and pulmonary disorders such as pulmonary embolism, and the like. Compounds that modulate HIF and can thus be used to treat and prevent HIF-associated disorders including conditions involving anemia, ischemia, and hypoxia are provided herein.

SUMMARY OF THE INVENTION

This invention is directed to novel compounds, and methods that can modulate the stability and/or activity of hypoxia inducible factor (HIF).

In one aspect, there are provided compounds represented by formula I:

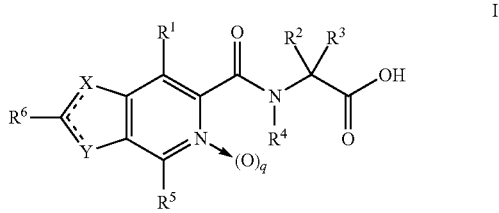

wherein
q is 0 or 1;
one of X or Y is —S—, and the other is $=C(R^7)$—;
$R^1$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, heterocyclyloxy, substituted heterocyclyloxy, mercapto, thioether, amino, substituted amino, and aminoacyl;
$R^2$ is selected from the group consisting of hydrogen, deuterium, and methyl;
$R^3$ is selected from the group consisting of hydrogen, deuterium, alkyl, and substituted alkyl;
$R^4$ is selected from the group consisting of hydrogen, alkyl, and substituted alkyl;
$R^5$ is selected from the group consisting of hydrogen, halo, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, thioether, cyano, and acyl;
$R^6$ and $R^7$ are independently selected from the group consisting of hydrogen, hydroxy, cyano, halo, nitro, acyl, amino, substituted amino, acylamino, sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, thioether, arylthio, substituted arylthio, heteroaryl, and substituted heteroaryl;
and pharmaceutically acceptable salts, single stereoisomers, mixtures of stereoisomers, esters, and prodrugs thereof.

The invention also provides pharmaceutical compositions comprising one or more compounds of Formula I and a pharmaceutically acceptable excipient. In some embodiments, the composition further comprises at least one additional therapeutic agent. In some embodiments, the agent is selected from the group consisting of vitamin B12, folic acid, ferrous sulfate, recombinant human erythropoietin and an erythropoiesis stimulating protein (ESP).

The invention is also directed to methods of treating, pretreating, or delaying onset of a condition mediated at least in part by hypoxia inducible factor (HIF) and/or erythropoietin (EPO), comprising administering to a patient, a therapeutically effective amount of a compound of Formula I.

DETAILED DESCRIPTION OF THE INVENTION

Before the present compositions, and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

As stated above, the invention is directed to compounds of formula I:

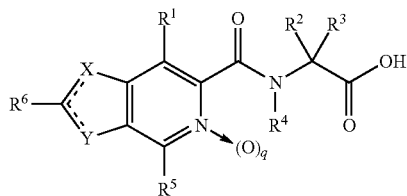

wherein
q is 0 or 1;
one of X or Y is —S—, and the other is =C($R^7$)—;
$R^1$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, heterocyclyloxy, substituted heterocyclyloxy, mercapto, thioether, amino, substituted amino, and aminoacyl;
$R^2$ is selected from the group consisting of hydrogen, deuterium, and methyl;
$R^3$ is selected from the group consisting of hydrogen, deuterium, alkyl, and substituted alkyl;
$R^4$ is selected from the group consisting of hydrogen, alkyl, and substituted alkyl;
$R^5$ is selected from the group consisting of hydrogen, halo, alkyl, substituted alkyl, alkenyl, substituted alkenyl, alkynyl, substituted alkynyl, alkoxy, substituted alkoxy, cycloalkyl, substituted cycloalkyl, cycloalkoxy, substituted cycloalkoxy, amino, substituted amino, aminoacyl, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, substituted heterocyclyloxy, thioether, cyano, and acyl;
$R^6$ and $R^7$ are independently selected from the group consisting of hydrogen, hydroxy, cyano, halo, nitro, acyl, amino, substituted amino, acylamino, sulfonyl, alkyl, substituted alkyl, alkenyl, substituted alkenyl, alkynyl, substituted alkynyl, alkoxy, substituted alkoxy, aryl, substituted aryl, aryloxy, substituted aryloxy, thioether, arylthio, substituted arylthio, heteroaryl, and substituted heteroaryl;
and pharmaceutically acceptable salts, single stereoisomers, mixtures of stereoisomers, esters, and prodrugs thereof.

In one embodiment, this invention relates to compounds of formula Ia:

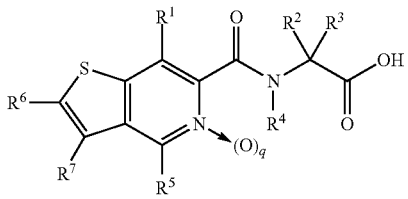

wherein $R^1$, $R^2$, $R^3$, $R^4$, $R^5$, $R^6$, $R^7$, and q are as defined above.
In another embodiment, the invention relates to compounds of formula Ib:

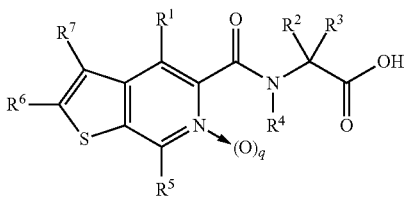

wherein $R^1$, $R^2$, $R^3$, $R^4$, $R^5$, $R^6$, $R^7$, and q are as defined above.
In some embodiments, q is 0.
In some embodiments, $R^1$ is hydroxy. In particular embodiments wherein $R^1$ is hydroxy, $R^2$, $R^3$, and $R^4$ are all hydrogen.
In some embodiments, $R^5$ is selected from the group consisting of hydrogen, alkyl, halo, aryl, substituted aryl, cyano, alkynyl, and heteroaryl. In particular embodiments, $R^5$ is selected from hydrogen, methyl, bromo, chloro, phenyl, fluorophenyl, cyano, ethynyl, furanyl, and thienyl.
In some embodiments, $R^6$ is selected from the group consisting of hydrogen, halo, alkyl, substituted alkyl, alkenyl, substituted alkenyl, aryl, substituted aryl, aryloxy, arylthio, and cyano. In particular embodiments, $R^6$ is selected from the group consisting of hydrogen, bromo, methyl, phenyl, trifluoromethylphenyl, phenoxyphenyl, fluorophenyl, phenylsulfanyl, phenoxy, phenethyl, phenylethenyl, and cyano.
In some embodiments, $R^7$ is hydrogen, aryl, or substituted aryl. In particular embodiments, $R^7$ is hydrogen, phenyl, or fluorophenyl.
In another embodiment, the present invention relates to compounds of formula Ia wherein
$R^1$ is hydroxy;
$R^2$, $R^3$, and $R^4$ are hydrogen;
$R^5$ is hydrogen, halo, alkyl, or aryl;
$R^6$ is hydrogen, halo, alkyl, substituted alkyl, aryl, substituted aryl, arylthio, alkenyl, substituted alkenyl, or aryloxy; and
$R^7$ is hydrogen, aryl, or substituted aryl;
or pharmaceutically acceptable salts, single stereoisomers, mixtures of stereoisomers, esters, and prodrugs thereof.
In another embodiment, the present invention relates to compounds of formula Ia wherein
$R^1$ is hydroxy;
$R^2$, $R^3$, and $R^4$ are hydrogen;
$R^5$ is halo, alkyl, alkynyl, cyano, aryl, substituted aryl, or heteroaryl;
$R^6$ is hydrogen, halo, alkyl, aryl, substituted aryl or cyano; and
$R^7$ is hydrogen, aryl, or substituted aryl;
or pharmaceutically acceptable salts, single stereoisomers, mixtures of stereoisomers, esters, and prodrugs thereof.

In another embodiment, the invention relates to compounds of formula Ib wherein
$R^1$ is hydroxy;
$R^2$, $R^3$, and $R^4$ are hydrogen;
$R^5$ is hydrogen, halo, alkyl, or aryl; and
$R^6$ is halo, alkyl, aryl, substituted aryl, or arylthio; and
$R^7$ is hydrogen or substituted aryl;
or pharmaceutically acceptable salts, single stereoisomers, mixtures of stereoisomers, esters, and prodrugs thereof.

In another embodiment, the invention relates to compounds of formula Ib wherein
$R^1$ is hydroxy;
$R^2$, $R^3$, and $R^4$ are hydrogen;
$R^5$ is hydrogen, halo, alkyl, aryl, substituted aryl, heteroaryl, alkynyl, or cyano;
$R^6$ is hydrogen, halo, alkyl, substituted aryl, arylsulfanyl, or cyano; and
$R^7$ is hydrogen or substituted aryl;
or pharmaceutically acceptable salts, single stereoisomers, mixtures of stereoisomers, esters, and prodrugs thereof.

Representative compounds for this application are presented in Table A. It will be understood that the dashed line in the structure below and the structures throughout represents a double bond that is either present between X and the adjacent carbon or Y and the adjacent carbon.

TABLE A

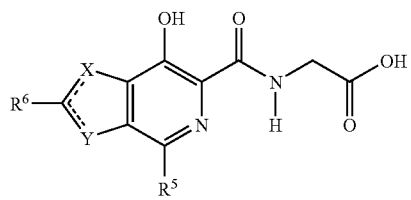

| No. | Formula | $R^5$ | $R^6$ | X | Y |
|---|---|---|---|---|---|
| 1 | Ib | H | bromo | =CH— | —S— |
| 2 | Ia | H | bromo | —S— | =CH— |
| 3 | Ib | H | 4-methoxyphenyl | =CH— | —S— |
| 4 | Ia | H | 4-methoxyphenyl | —S— | =CH— |
| 5 | Ib | methyl | methyl | =CH— | —S— |
| 6 | Ia | methyl | methyl | —S— | =CH— |
| 7 | Ia | methyl | 4-phenoxyphenyl | —S— | =CH— |
| 8 | Ib | methyl | 4-phenoxyphenyl | =CH— | —S— |
| 9 | Ib | H | 4-phenoxyphenyl | =CH— | —S— |
| 10 | Ia | H | 4-phenoxyphenyl | —S— | =CH— |
| 11 | Ib | bromo | bromo | =CH— | —S— |
| 12 | Ib | chloro | bromo | =CH— | —S— |
| 13 | Ia | H | H | —S— | =CH— |
| 14 | Ib | H | H | =CH— | —S— |
| 15 | Ia | chloro | bromo | —S— | =CH— |
| 16 | Ia | bromo | bromo | —S— | =CH— |
| 17 | Ia | H | phenylsulfanyl | —S— | =CH— |
| 18 | Ib | H | phenylsulfanyl | =CH— | —S— |
| 19 | Ib | phenyl | phenyl | =CH— | —S— |
| 20 | Ia | phenyl | phenyl | —S— | =CH— |
| 21 | Ia | H | (E)-styryl | —S— | =CH— |
| 22 | Ia | H | phenoxy | —S— | =CH— |
| 23 | Ia | H | phenethyl | —S— | =CH— |
| 24 | Ia | H | 3-(trifluoromethyl)-phenyl | —S— | =CH— |
| 25 | Ia | bromo | 3-(trifluoromethyl)-phenyl | —S— | =CH— |
| 26 | Ia | cyano | 3-(trifluoromethyl)-phenyl | —S— | =CH— |
| 27 | Ia | H | cyano | —S— | =CH— |
| 28 | Ia | H | 4-(trifluoromethyl)-phenyl | —S— | =CH— |
| 29 | Ia | H | 2-(trifluoromethyl)-phenyl | —S— | =CH— |
| 30 | Ia | bromo | H | —S— | =C(4-fluorophenyl)- |
| 31 | Ia | H | H | —S— | =C(4-fluorophenyl)- |
| 32 | Ia | methyl | H | —S— | =C(4-fluorophenyl)- |
| 33 | Ia | cyano | H | —S— | =C(4-fluorophenyl)- |
| 34 | Ia | H | 4-fluorophenyl | —S— | =CH— |
| 35 | Ia | methyl | 4-fluorophenyl | —S— | =CH— |
| 36 | Ia | H | 4-fluorophenyl | —S— | =C(4-fluorophenyl)- |
| 37 | Ib | bromo | H | =C(4-fluorophenyl)- | —S— |
| 38 | Ib | H | H | =C(4-fluorophenyl)- | —S— |
| 39 | Ib | H | 4-fluorophenyl | =CH— | —S— |

TABLE A-continued

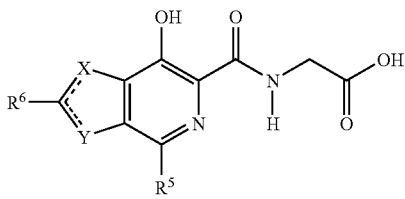

| No. | Formula | R⁵ | R⁶ | X | Y |
|---|---|---|---|---|---|
| 40 | Ib | methyl | 4-fluorophenyl | =CH— | —S— |
| 41 | Ib | chloro | H | =CH— | —S— |
| 42 | Ia | chloro | H | —S— | =CH— |
| 43 | Ib | bromo | H | =CH— | —S— |
| 44 | Ia | bromo | H | —S— | =CH— |
| 45 | Ib | phenyl | H | =CH— | —S— |
| 46 | Ia | phenyl | H | —S— | =CH— |
| 47 | Ib | 4-fluorophenyl | H | =CH— | —S— |
| 48 | Ia | 4-fluorophenyl | H | —S— | =CH— |
| 49 | Ib | 2-furyl | H | =CH— | —S— |
| 50 | Ia | 2-furyl | H | —S— | =CH— |
| 51 | Ib | 3-furyl | H | =CH— | —S— |
| 52 | Ia | 3-furyl | H | —S— | =CH— |
| 53 | Ib | 2-thienyl | H | =CH— | —S— |
| 54 | Ia | 2-thienyl | H | —S— | =CH— |
| 55 | Ib | 3-thienyl | H | =CH— | —S— |
| 56 | Ia | 3-thienyl | H | —S— | =CH— |
| 57 | Ib | methyl | H | =CH— | —S— |
| 58 | Ia | methyl | H | —S— | =CH— |
| 59 | Ib | ethynyl | H | =CH— | —S— |
| 60 | Ia | ethynyl | H | —S— | =CH— |
| 61 | Ib | cyano | H | =CH— | —S— |
| 62 | Ia | cyano | H | —S— | =CH— |

Compounds included within the scope of this invention include, for example, [(2-bromo-4-hydroxy-thieno[2,3-c]pyridine-5-carbonyl)-amino]-acetic acid; [(2-bromo-7-hydroxy-thieno[3,2-c]pyridine-6-carbonyl)-amino]-acetic acid; {[4-hydroxy-2-(4-methoxy-phenyl)-thieno[2,3-c]pyridine-5-carbonyl]-amino}-acetic acid; {[7-hydroxy-2-(4-methoxy-phenyl)-thieno[3,2-c]pyridine-6-carbonyl]amino}-acetic acid; [(4-hydroxy-2,7-dimethyl-thieno[2,3-c]pyridine-5-carbonyl)-amino]-acetic acid; [(7-hydroxy-2,4-dimethyl-thieno[3,2-c]pyridine-6-carbonyl)-amino]-acetic acid; {[7-hydroxy-4-methyl-2-(4-phenoxy-phenyl)-thieno[3,2-c]pyridine-6-carbonyl]-amino}-acetic acid; {[4-hydroxy-2-(4-phenoxy-phenyl)-7-methyl-thieno[2,3-c]pyridine-5-carbonyl]-amino}-acetic acid; {[4-hydroxy-2-(4-phenoxy-phenyl)-thieno[2,3-c]pyridine-5-carbonyl]-amino}-acetic acid; {[7-hydroxy-2-(4-phenoxy-phenyl)-thieno[3,2-c]pyridine-6-carbonyl]-amino}-acetic acid; [(2,7-dibromo-4-hydroxy-thieno[2,3-c]pyridine-5-carbonyl)-amino]-acetic acid; [(2-bromo-7-chloro-4-hydroxy-thieno[2,3-c]pyridine-5-carbonyl)-amino]-acetic acid; [(7-hydroxy-thieno[3,2-c]pyridine-6-carbonyl)-amino]-acetic acid; [(4-hydroxy-thieno[2,3-c]pyridine-5-carbonyl)-amino]-acetic acid; [(2-bromo-4-chloro-7-hydroxy-thieno[3,2-c]pyridine-6-carbonyl)-amino]-acetic acid; [(2,4-dibromo-7-hydroxy-thieno[3,2-c]pyridine-6-carbonyl)-amino]-acetic acid; [(7-hydroxy-2-phenylsulfanyl-thieno[3,2-c]pyridine-6-carbonyl)-amino]-acetic acid; [(4-hydroxy-2-phenylsulfanyl-thieno[2,3-c]pyridine-5-carbonyl)-amino]-acetic acid; [(4-hydroxy-2,7-diphenyl-thieno[2,3-c]pyridine-5-carbonyl)-amino]-acetic acid; [(7-hydroxy-2,4-diphenyl-thieno[3,2-c]pyridine-6-carbonyl)-amino]-acetic acid; [(7-hydroxy-2-styryl-thieno[3,2-c]pyridine-6-carbonyl)-amino]-acetic acid; [(7-hydroxy-2-phenoxy-thieno[3,2-c]pyridine-6-carbonyl)-amino]-acetic acid; [(7-hydroxy-2-phenethyl-thieno[3,2-c]pyridine-6-carbonyl)-amino]-acetic acid; {[7-hydroxy-2-(3-trifluoromethyl-phenyl)-thieno[3,2-c]pyridine-6-carbonyl]-amino}-acetic acid; {[4-bromo-7-hydroxy-2-(3-trifluoromethyl-phenyl)-thieno[3,2-c]pyridine-6-carbonyl]-amino}-acetic acid; {[4-cyano-7-hydroxy-2-(3-trifluoromethyl-phenyl)-thieno[3,2-c]pyridine-6-carbonyl]-amino}-acetic acid; [(2-cyano-7-hydroxy-thieno[3,2-c]pyridine-6-carbonyl)-amino]-acetic acid; {[7-hydroxy-2-(4-trifluoromethyl-phenyl)-thieno[3,2-c]pyridine-6-carbonyl]-amino}-acetic acid; {[7-hydroxy-2-(2-trifluoromethyl-phenyl)-thieno[3,2-c]pyridine-6-carbonyl]-amino}-acetic acid; {[4-bromo-3-(4-fluoro-phenyl)-7-hydroxy-thieno[3,2-c]pyridine-6-carbonyl]-amino}-acetic acid; {[3-(4-fluoro-phenyl)-7-hydroxy-thieno[3,2-c]pyridine-6-carbonyl]-amino}-acetic acid; {[3-(4-fluoro-phenyl)-7-hydroxy-4-methyl-thieno[3,2-c]pyridine-6-carbonyl]-amino}-acetic acid; {[4-cyano-3-(4-fluoro-phenyl)-7-hydroxy-thieno[3,2-c]pyridine-6-carbonyl]-amino}-acetic acid; {[2-(4-fluoro-phenyl)-7-hydroxy-thieno[3,2-c]pyridine-6-carbonyl]-amino}-acetic acid; {[2-(4-fluoro-phenyl)-7-hydroxy-4-methyl-thieno[3,2-c]pyridine-6-carbonyl]-amino}-acetic acid; {[2,3-bis-(4-fluoro-phenyl)-7-hydroxy-thieno[3,2-c]pyridine-6-carbonyl]-amino}-acetic acid; {[7-bromo-3-(4-fluoro-phenyl)-4-hydroxy-thieno[2,3-c]pyridine-5-carbonyl]-amino}-acetic acid; {[3-(4-fluoro-phenyl)-4-hydroxy-thieno[2,3-c]pyridine-5-carbonyl]-amino}-acetic acid; {[2-(4-fluoro-phenyl)-4-hydroxy-thieno[2,3-c]pyridine-5-carbonyl]-amino}-acetic acid; {[2-(4-fluoro-phenyl)-4-hydroxy-7-methyl-thieno[2,3-c]pyridine-5-carbonyl]-amino}-acetic acid; [(7-chloro-4-hydroxy-thieno[2,3-c]pyridine-5-carbonyl)-amino]-acetic acid; [(4-chloro-7-hydroxy-thieno[3,2-c]pyridine-6-carbonyl)- amino]-acetic acid; [(7-bromo-4-hydroxy-thieno[2,3-c]pyridine-5-carbonyl)-amino]-acetic acid; [(4-bromo-7-hydroxy-thieno[3,2-c]pyridine-6-carbonyl)-amino]-acetic acid; [(4-hydroxy-7-phenyl-thieno[2,3-c]pyridine-5-carbonyl)-amino]-acetic acid; [(7-hydroxy-4-phenyl-thieno[3,2-c]pyridine-6-carbonyl)-amino]-acetic acid; {[7-(4-fluoro-phenyl)-4-hydroxy-thieno[2,3-c]pyridine-5-carbonyl]-amino}-acetic acid; {[4-(4-fluoro-phenyl)-7-hydroxy-thieno[3,2-c]pyridine-6-carbonyl]-amino}-acetic acid; 2-(7-(furan-2-yl)-4-hydroxythieno[2,3-c]pyridine-5-carboxamido)acetic acid; [(4-furan-2-yl-7-hydroxy-thieno[3,2-c]pyridine-6-carbonyl)-amino]-acetic acid; [(7-furan-3-yl-4-hydroxy-thieno[2,3-c]pyridine-5-carbonyl)-amino]-acetic acid; [(4-furan-3-yl-7-hydroxy-thieno[3,2-c]pyridine-6-carbonyl)-amino]-acetic acid; 2-(4-hydroxy-7-(thiophen-2-yl)thieno[2,3-c]pyridine-5-carboxamido)acetic acid; [(7-hydroxy-4-thiophen-2-yl-thieno[3,2-c]pyridine-6-carbonyl)-amino]-acetic acid; [(4-hydroxy-7-thiophen-3-yl-thieno[2,3-c]pyridine-5-carbonyl)-amino]-acetic acid; [(7-hydroxy-4-thiophen-3-yl-thieno[3,2-c]pyridine-6-carbonyl)-amino]-acetic acid; [(4-hydroxy-7-methyl-thieno[2,3-c]pyridine-5-carbonyl)-amino]-acetic acid; [(7-hydroxy-4-methyl-thieno[3,2-c]pyridine-6-carbonyl)-amino]-acetic acid; [(7-ethynyl-4-hydroxy-thieno[2,3-c]pyridine-5-carbonyl)-amino]-acetic acid; [(4-ethynyl-7-hydroxy-thieno[3,2-c]pyridine-6-carbonyl)-amino]-acetic acid; [(7-cyano-4-hydroxy-thieno[2,3-c]pyridine-5-carbonyl)-amino]-acetic acid; [(4-cyano-7-hydroxy-thieno[3,2-c]pyridine-6-carbonyl)-amino]-acetic acid; and pharmaceutically acceptable salts, single stereoisomers, mixtures of stereoisomers, esters, and prodrugs thereof.

2. Compositions and Methods of the Invention

The invention also provides for use of a compound of formula I, Ia, and/or Ib for the manufacture of a medicament for use in treating various conditions or disorders as described below. In one embodiment, a pharmaceutical composition is provided comprising a pharmaceutically acceptable excipient or carrier, and a therapeutically effective amount of at least one compound selected from the group consisting of formulae I, Ia, and/or Ib.

The invention also contemplates the medicament or composition further comprising at least one additional therapeutic agent selected from the group including, but not limited to, vitamin B12, ferrous sulfate, folic acid, and/or recombinant erythropoietin or an erythropoiesis stimulating protein (ESP).

The invention is also directed to use of a compound, or composition or medicament thereof, to treat, pretreat, or delay onset of a condition mediated at least in part by hypoxia inducible factor (HIF) and/or erythropoietin (EPO). The use comprises administering to a mammalian patient a therapeutically effective amount of a medicament or pharmaceutical composition comprising one or more compounds of formulae I, Ia, and/or Ib.

The condition can be selected from the group consisting of anemic disorders; neurological disorders and/or injuries including cases of stroke, trauma, epilepsy, and neurodegenerative disease; myocardial infarction, liver ischemia, renal ischemia, peripheral vascular disorders, ulcers, burns, and chronic wounds; pulmonary embolism; and ischemic-reperfusion injury.

The invention is also directed to a method of inhibiting the activity of at least one hydroxylase enzyme which modifies the alpha subunit of hypoxia inducible factor. The method comprises contacting the enzyme with an inhibiting effective amount of one or more compounds selected from the group comprising compounds of formulae I, Ia, and/or Ib.

3. Definitions

It must be noted that as used herein, and in the appended claims, the singular forms "a," "an," and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) J. Biol. Chem 272:19253-19260), amino acid 556 to 575 (Tanimoto et al., supra), amino acid 557 to 571 (Srinivas et al. (1999) Biochem Biophys Res. Commun 260:557-561), and amino acid 556 to 575 (Ivan, and Kaelin (2001) Science 292:464-468). Further, HIFα fragments include any fragment containing at least one occurrence of the motif LXXLAP, e.g., as occurs in the human HIF-1α native sequence from $L_{397}$ to $P_{402}$, and from $L_{559}$ to $P_{564}$.

The term "HIF PH" refers to any enzyme capable of hydroxylating a proline residue in the HIF protein. Preferably, the proline residue hydroxylated by HIF PH includes the proline found within the motif LXXLAP. HIF PH includes members of the Egl-Nine (EGLN) gene family described by Taylor (2001, Gene 275:125-132), and characterized by Aravind, and Koonin (2001, Genome Biol 2: RESEARCH 0007), Epstein et al. (2001, Cell 107:43-54), and Bruick and McKnight (2001, Science 294:1337-1340). HIF PH2, as used in assays described herein, may be selected from human EGLN1 (hEGLN1, GenBank Accession No. AAG33965; Dupuy et al. (2000) Genomics 69:348-54), mouse EGLN1 (GenBank Accession No. CAC42515), and rat EGLN1 (GenBank Accession No. P59722). Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AAO46039); human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retain at least one structural or functional characteristic.

The term "anemia" as used herein refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

Anemia can arise due to conditions such as acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively and refer to any condition deviating from normal.

The terms "anemic conditions" and "anemic disorders" refer to any condition, disease, or disorder associated with anemia. Such disorders include, but are not limited to, those disorders listed above. Anemic disorders further include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

The term "erythropoietin-associated conditions" is used inclusively and refers to any condition associated with below normal, abnormal, or inappropriate modulation of erythropoietin. Erythropoietin-associated conditions include any condition wherein an increase in EPO level would provide therapeutic benefit. Levels of erythropoietin associated with such conditions can be determined by any measure accepted and utilized by those of skill in the art. Erythropoietin-associated conditions include anemic conditions such as those described above.

Erythropoietin-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The term "erythropoietin" refers to any recombinant or naturally occurring erythropoietin or ESP including, e.g., human erythropoietin (GenBank Accession No. AAA52400; Lin et al. (1985) Proc Nat'l Acad. Sci USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), glycosylated erythropoietin such as those described in U.S. Pat. No. 6,930,086 (which is incorporated by reference), etc.

The term "alkyl" refers to saturated monovalent hydrocarbyl groups having from 1 to 10 carbon atoms, preferably from 1 to 5 carbon atoms, and more preferably 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group, of from 1 to 10 carbon atoms, preferably, 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl.

The term "alkoxy" refers to the group "alkyl-O-" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O-".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" and the prefix "carbamoyl" or "carboxamide" or "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to an acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, provided that both R$^{41}$ groups are not hydrogen; or the R$^{41}$ groups can be joined together with the nitrogen atom to form a heterocyclic or substituted heterocyclic ring.

The term "acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O- substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy" or as a prefix "carbamoyloxy" or "substituted carbamoyloxy" refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)NR$^{49}$— where each R$^{49}$ is independently selected from the group consisting of hydrogen and alkyl.

The term "aminothiocarbonylamino" refers to the group —NR$^{49}$C(S)NR$^{49}$— where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl, and naphthyl.

The term "substituted aryl" refers to aryl groups, as defined herein, which are substituted with from 1 to 4, preferably 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^5$-heterocyclic, —NR$^{51}$S(O)$_2$—NR$^{51}$-substituted heterocyclic, where each R$^{51}$ is independently selected from hydrogen or alkyl, wherein each of the terms is as defined herein.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl esters" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo, and preferably is fluoro or chloro.

The term "heteroaryl" refers to an aromatic group of from 1 to 15 carbon atoms, preferably from 1 to 10 carbon atoms, and 1 to 4 heteroatoms selected from the group consisting of oxygen, nitrogen, and sulfur within the ring. Such heteroaryl groups can have a single ring (e.g., pyridinyl, furyl, or thienyl) or multiple condensed rings (e.g., indolizinyl or benzothienyl). The nitrogen and/or sulfur ring atoms can optionally be oxidized to provide for the N-oxide or the sulfoxide, and sulfone derivatives. Preferred heteroaryls include pyridinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl.

The term "heteroaryloxy" refers to the group —O-heteroaryl, and "substituted heteroaryloxy" refers to the group —O-substituted heteroaryl.

The term "heterocycle" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic, and "substituted heterocyclyloxy" refers to the group —O-substituted heterocyclic.

"Thiol" or "mercapto" refers to the group —SH. The term "sulfonyl" refers to the group —$SO_2H$.

"Alkylsulfanyl", "alkylthio", and "thioether" refer to the groups —S-alkyl where alkyl is as defined above.

"Substituted alkylthio" and "substituted alkylsulfanyl" refer to the group —S-substituted alkyl where alkyl is as defined above.

"Cycloalkylthio" or "cycloalkylsulfanyl" refers to the groups —S-cycloalkyl where cycloalkyl is as defined above.

"Substituted cycloalkylthio" refers to the group —S-substituted cycloalkyl where substituted cycloalkyl is as defined above.

"Arylthio" or "arylsulfanyl" refers to the group —S-aryl, and "substituted arylthio" refers to the group —S-substituted aryl where aryl and substituted aryl are as defined above.

"Heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

"Heterocyclicthio" refers to the group —S-heterocyclic, and "substituted heterocyclicthio" refers to the group —S-substituted heterocyclic where heterocyclic, and substituted heterocyclic are as defined above.

The term "amino acid" refers to any of the naturally occurring amino acids, as well as synthetic analogs (e.g., D-stereoisomers of the naturally occurring amino acids, such as D-threonine), and derivatives thereof. α-Amino acids comprise a carbon atom to which is bonded an amino group, a carboxyl group, a hydrogen atom, and a distinctive group referred to as a "side chain." The side chains of naturally occurring amino acids are well known in the art, and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine, and tryptophan), substituted arylalkyl (e.g., as in tyrosine), and heteroarylalkyl (e.g., as in histidine). Unnatural amino acids are also known in the art, as set forth in, for example, Williams, ed. (1989) Synthesis of Optically Active α-Amino Acids, Pergamon Press; Evans et al. (1990) J. Amer. Chem. Soc. 112:4011-4030; Pu et al. (1991) J. Amer. Chem. Soc. 56:1280-1283; Williams et al. (1991) J. Amer. Chem. Soc. 113:9276-9286; and all references cited therein. The present invention includes the side chains of unnatural amino acids as well.

"Pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The term "prodrug", as used herein, refers to compounds of formula I, Ia, and Ib that include chemical groups which, in vivo, can be converted into the carboxylate group on the glycine or alanine substituent of the compounds and/or can be split off from the amide N-atom and/or can be split off from the 4-O atom of the thieno[2,3-c]pyridine or the 7-O atom of the thieno[3,2-c]pyridine; and/or can be split off from the N-atom of the pyridyl ring to provide for the active drug, a pharmaceutically acceptable salt thereof, or a biologically active metabolite thereof. Suitable groups are well known in the art and particularly include: for the carboxylic acid moiety on the glycine or alanine substituent, a prodrug selected from, e.g., esters including, but not limited to, those derived from alkyl alcohols, substituted alkyl alcohols, hydroxy substituted aryls and heteroaryls and the like; amides, particularly amides derived from amines of the formula $HNR^{20}R^{21}$ where $R^{20}$ and $R^{21}$ are independently hydrogen, alkyl, substituted alkyl, aryl, substituted aryl, and the like; hydroxymethyl, aldehyde and derivatives thereof; and for the pyridyl N atom, a prodrug selected from, e.g., N-oxides and N-alkyl derivatives.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group

19 alpha to ethenylic or acetylenic unsaturation). Such impermissible substitution patterns are well known to the skilled artisan.

4. Compound Preparation

The compounds of this invention can be prepared from readily available starting materials using, for example, the following general methods, and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Scheme 1

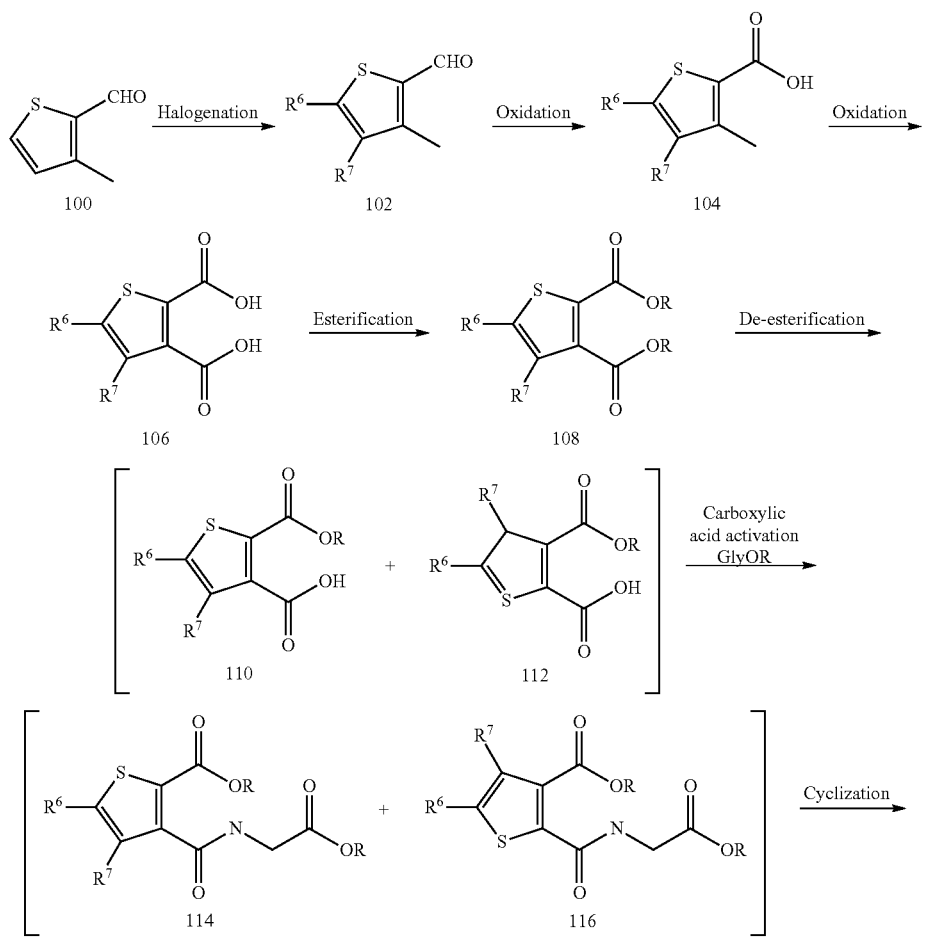

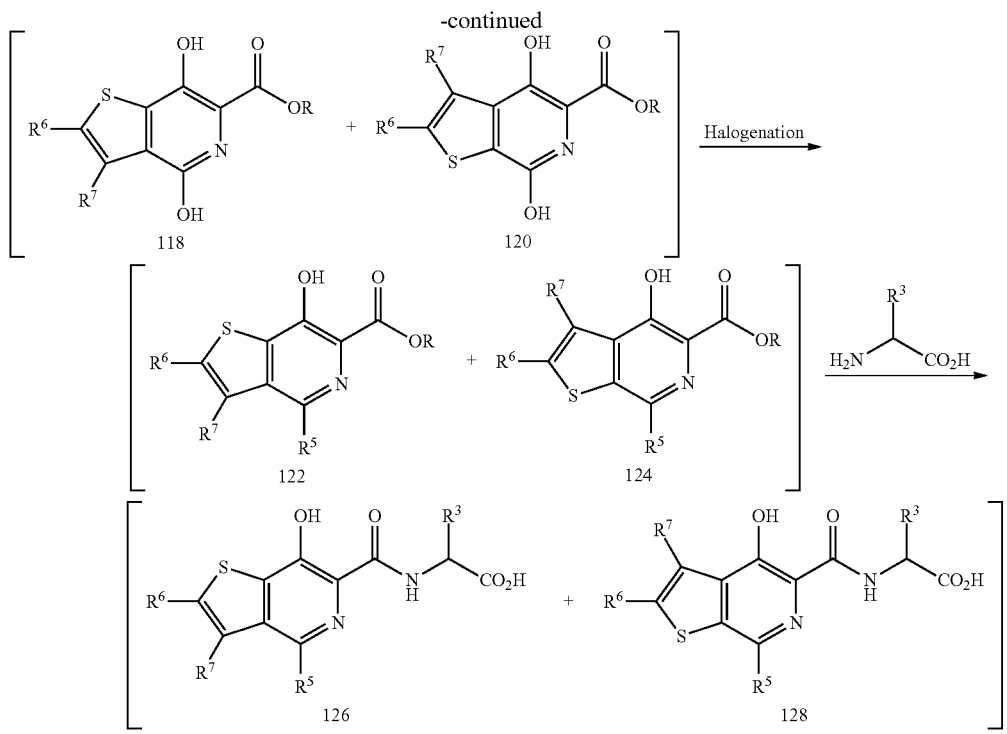

Scheme 1 illustrates a general method for the preparation of intermediates and compounds of this invention. These compounds are prepared from starting materials either known in the art or commercially available.

In Scheme 1, compounds of the formula 100, such as commercially available 3-methylthiophene-2-carboxaldehyde, are halogenated through conventional methods to produce compounds of formula 102 where halogen occupies the $R^6$ or $R^6$ and $R^7$ positions. A preferred halogenation method is bromination with an equivalent of bromine, to provide for 5-bromo-3-methyl-thiophene-2-carboxaldehyde, a compound of the formula 102 where $R^6$=Br and $R^7$=H. In turn, the carboxaldehyde substituent of compounds of the formula 102 is oxidized under conventional conditions, for example, by treatment with sodium chlorite, Jones reagent, or silver oxide, to provide for functionalized-3-methylthiophene-2-carboxylic acid, compounds of the formula 104. Alternatively, commercially available versions of compounds of the formula 104 can be utilized, such as 3-methyl-5-bromothiophene-2-carboxylic acid where $R^6$=H and $R^7$=Br, or 3-methyl-thiophene-2-carboxylic acid where $R^6$=H and $R^7$=H. Alternatively, known synthetic methods may be used to produce-intermediates of type 104 where $R^6$ or $R^7$ may be H, Br, Cl, I, $NO_2$, F, aryl, and substituted aryl. Subsequent oxidation of the 3-methyl substituent to the corresponding 3-carboxylic acid group of dicarboxylic acid compounds of the formula 106 proceed, again, by conventional methods using, for example, an excess of potassium permanganate as the oxidizing agent. Alternatively, compounds of the formula 102 may be directly oxidized to compounds of the formula 106, for example, by treatment with excess potassium permanganate.

Esterification of the dicarboxylic acid groups of compounds of the formula 106 proceeds conventionally to provide for the corresponding diester of compounds of the formula 108. In one embodiment, esterification is accomplished by treatment of the di-acid with an activating species, such as thionyl chloride or oxalyl chloride, followed by addition of alcohol, such as methanol, ethanol, or butanol, where methanol is preferred, or for example, by treatment of 106 with a strong acid in the presence of excess alcohol. Mono-deesterification of compounds of the formula 108 proceeds using an equivalent of sodium hydroxide which provides for a mixture of thiophene-2,3-dicarboxylic acid 2-methyl ester and thiophene-2,3-dicarboxylic acid 3-methyl ester, compounds of the formula 110 and 112. The free acid group of compounds of the formula 110 and 112 are amidated via conventional methods to provide for compounds of the formula 114 and 116.

Cyclization of compounds of the formula 114 and 116 in the presence of a suitable base, such as sodium alkoxide, where sodium n-butoxide in n-butanol is preferred, provides for functionalized-4,7-dihydroxythieno[2,3-c]pyridine-5-carboxylic acid alkyl ester and functionalized-4,7-dihydroxythieno[3,2-c]pyridine-6-carboxylic acid alkyl ester, compounds of the formula 118 and 120, where the n-butyl ester is preferred. The hydroxyl group alpha to the nitrogen atom in the pyridinyl group of compounds of the formula 118 and 120 is substantially more reactive than the opposing hydroxyl group and, accordingly, allows for selective differentiation over the opposing hydroxyl group. Differentiation can be achieved by treating compounds of the formula 118 and 120 with an excess of a phosphorus oxyhalide, such as $POCl_3$ or $POBr_3$, which results in halogenation to produce compounds of the formula 122 and 124 where $R^5$ is halogen. Conventional amidation conditions using a compound of the formula $H_2NCR^2R^3C(O)OH$ or an ester thereof then provides for compounds of the formula 126 and 128 (after de-esterification if the ester is used).

Scheme 2 illustrates an alternative method for preparing intermediates useful in preparing compounds of this invention.

Scheme 2

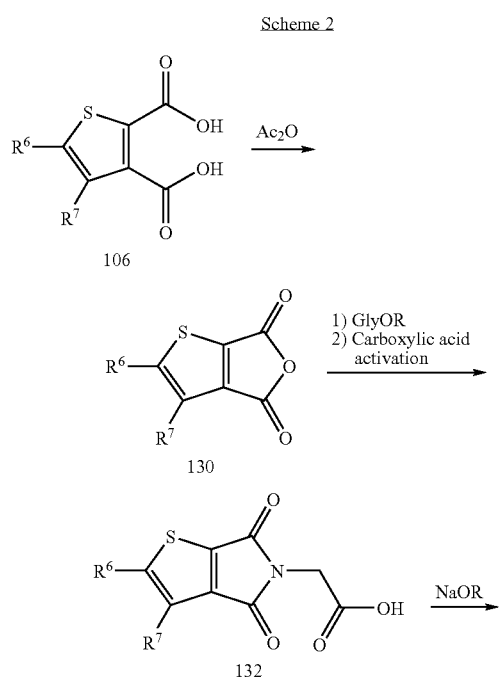

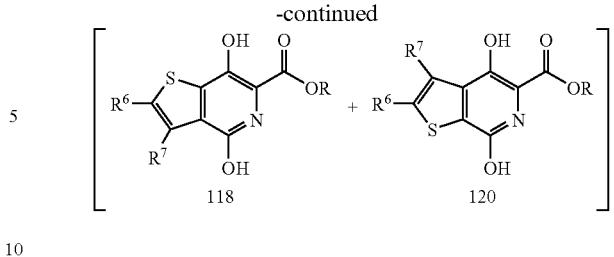

Specifically, compounds of the formula 106, prepared as in Scheme 1, are converted first to the corresponding anhydride, compounds of the formula 130, by treatment with an excess of acetic anhydride. The anhydride is converted to the corresponding N-substituted imide, compounds of the formula 132, by reaction with a glycine ester (GlyOR, where R may be, but is not limited to, methyl, ethyl, or n-butyl) followed by treatment with a carboxylic acid activating species, such as thionyl chloride, pivaloyl chloride, chloroformate derivatives, carbodiimides, or oxalyl chloride. Ring expansion and generation of functionalized-4,7-dihydroxythieno[2,3-c]pyridine-5-carboxylic acid alkyl ester and functionalized-4,7-dihydroxythieno[3,2-c]pyridine-6-carboxylic acid alkyl ester, compounds of the formula 118 and 120, then proceeds via reaction with a suitable base such as a sodium alkoxide in alcohol, where sodium n-butoxide in n-butanol is preferred.

Scheme 3

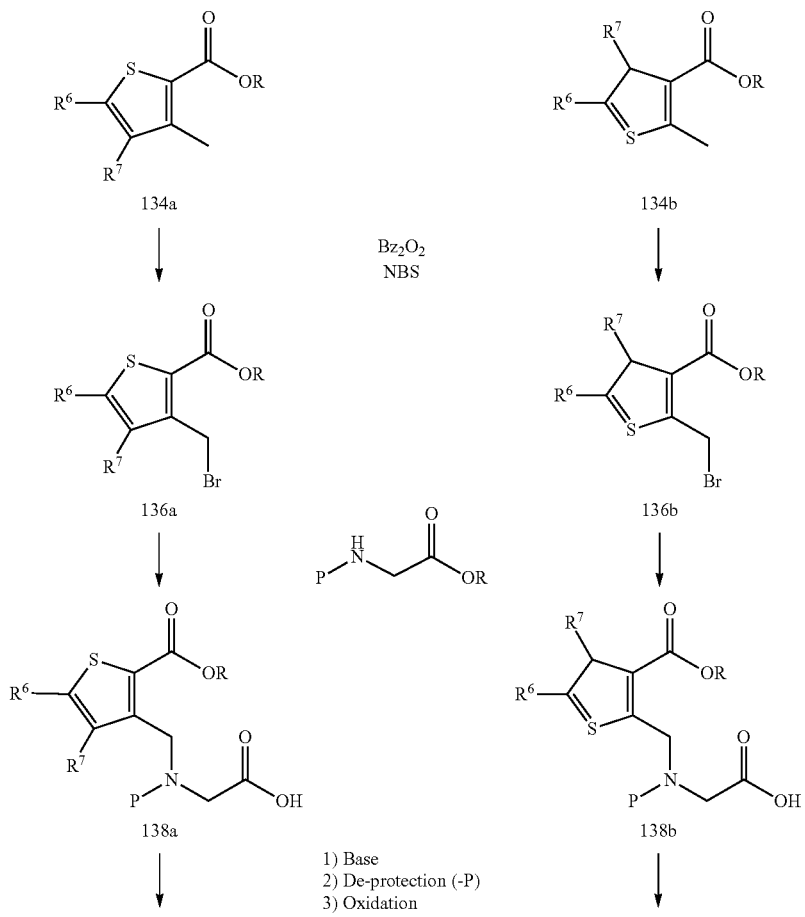

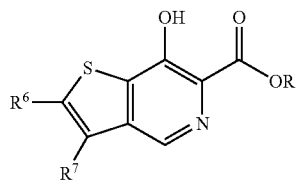

140a

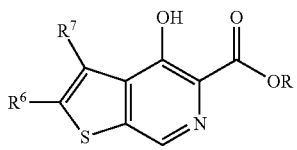

140b

Halogenation

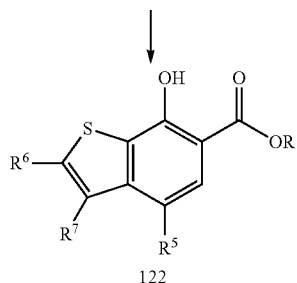

122

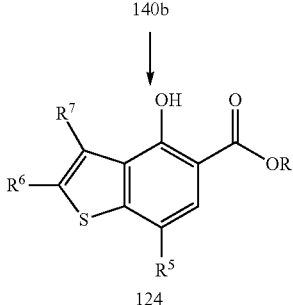

124

Alternatively, Scheme 3 illustrates a second general route for the preparation of intermediates to compounds pertaining to this invention.

For illustrative purposes only, $R^6$ and $R^7$ may be hydrogen or halogen. Compounds of the formula 134a and 134b where R may be, but is not limited to, methyl, ethyl, or n-butyl, may be prepared, e.g., by the esterification of compounds of the formula 104, which are described in Scheme 1, by conventional methods. Compounds of the formula 134a and 134b are halogenated at the methyl position to produce either 3-bromomethyl-thiophene-2-carboxylic esters of the formula 136a or 2-bromomethyl-thiophene-3-carboxylic esters of the formula 136b by conventional methods; for example, addition of a halogen source (such as N-bromosuccinimide) and a radical initiator (such as benzoyl peroxide or azobisisobutyronitrile) in appropriate solvent (such as carbon tetrachloride, benzene, or dichloromethane), and allowing to react (thermally or UV initiation) for an appropriate length of time, where the thermal reaction of N-bromosuccinimide and benzoyl peroxide in carbon tetrachloride is preferred. Alternative methods of this transformation may include, but are not limited to, oxidation of the methyl substituent to hydroxymethyl followed by conversion of the hydroxy group into an appropriate leaving group, such as a halogen, as illustrated above, or substituted sulfonate.

Compounds of the formula 136a and 136b are reacted with an appropriate N-protected glycine ester under conventional conditions, such as stirring in DMF in the presence of an appropriate base, to form compounds of the formula 138a and 138b, respectively. Glycine derived reactants may include, but are not limited to, compounds with tert-butoxy carbonyl, tosyl, benzyl, or substituted benzyl groups (P) on the glycine nitrogen; and methyl, ethyl, or n-butyl groups (R) on the carboxylate; where N-(2,4-dimethoxy-benzyl)glycine ethyl ester is a preferred reactant. Compounds of the formula 138a and 138b are converted to compounds of the formula 140a and 140b, respectively, by a series of steps in which intermediates may be isolated or may be used without purification. First, compounds of the formula 138a and 138b are treated with an appropriate base, such as potassium tert-butoxide, lithium diisopropylamide, or lithium bis(trimethylsilyl) amide, to affect a Dieckman condensation. The resulting compounds are then deprotected, using conventional conditions appropriate for the removal of the protecting group (P), and oxidized, using conventional conditions such as stirring under an oxygen-containing atmosphere or treating with an oxidizing agent such as bromine, to form compounds of the formula 140a and 140b. The process of oxidation and deprotection may be done simultaneously, with use of a protecting group that is labile under the oxidative conditions. One preferred method of this transformation is stirring a compound of formula 136a or 136b with N-(2,4-dimethoxy-benzyl)glycine ethyl ester in DMF with potassium carbonate to affect condensation, cyclizing with potassium tert-butoxide in THF, and then oxidizing and cleaving the N-2,4-dimethoxy-benzyl group by treatment with thionyl chloride in dichloromethane to provide compounds of the formula 140a or 140b, respectively. Compounds of the formula 140a and 140b may be selectively halogenated to introduce a halogen alpha to the nitrogen of the pyridyl ring to produce compounds of the formula 122 and 124, respectively, where $R^5$ is halogen. Conventional methods of halogenation may be used, such as treatment with N-bromosuccinimide or N-chlorosuccinamide in the presence of a radical initiator, or electrophilic reaction of N-bromosuccinimide in acetonitrile, where heating N-bromosuccinimide, benzoyl peroxide, and 140a or 140b in a carbon tetrachloride solution at reflux temperature for an appropriate period of time is preferred.

Compounds of the formula 140a and 140b may also be converted to compounds of formula 126 and 128 by conventional amidation conditions using a compound of the formula $H_2NCR^2R^3C(O)OH$ or an ester thereof, followed by appropriate de-esterification when necessary.

As exemplified in schemes 4-6 below, intermediates that contain one or more halogens, for example bromine, at $R^5$, $R^6$, and/or $R^7$ positions, may be modified by conventional means to transform the halogen into an alternate functional group. Examples may include, but are not limited to transformation of bromine into a hydrogen, cyano, alkoxy, aryloxy, thioether, acly, alkyl, alkenyl, aryl, or alkynyl substituent, which may occur at several points along the proceeding generic routes exemplified in schemes 1-3. These transformations may include, but are not limited to, Suzuki coupling reactions, Stille coupling reactions, Heck couplings, Castro-Stevens (Sonogashira) couplings, transition metal mediated carbonyl insertions, nucleophilic displacement, hydrogenation, metal exchange and electrophilic substitution. Once incorporated into the intermediate structures, these new functional groups may be chemically modified further through additional chemical transformations not shown on the general schemes. Dependent on functional group compatibility, transformation of halogens to an alternative substituent may occur on, but are not limited to, compounds of the formula 102, 104, 106, 108, 114, 116, 118, 120, 122, 124, 126, 128, 130, 132, 134a, 134b, 138a, 138b, 140a, and 140b, and compounds containing new substituents at the $R^5$, $R^6$, and/or $R^7$ positions may then be elaborated to final compounds following the generic synthetic schemes shown above. Sequential modification of compounds with multiple halogens may be employed to introduce non-equivalent substituents, such as exemplified in scheme 6.

Scheme 4 below illustrates some specific conversion pathways to the synthesis of compounds of formula I, in particular how intermediates containing multiple halogens are converted to non-halogenated compounds.

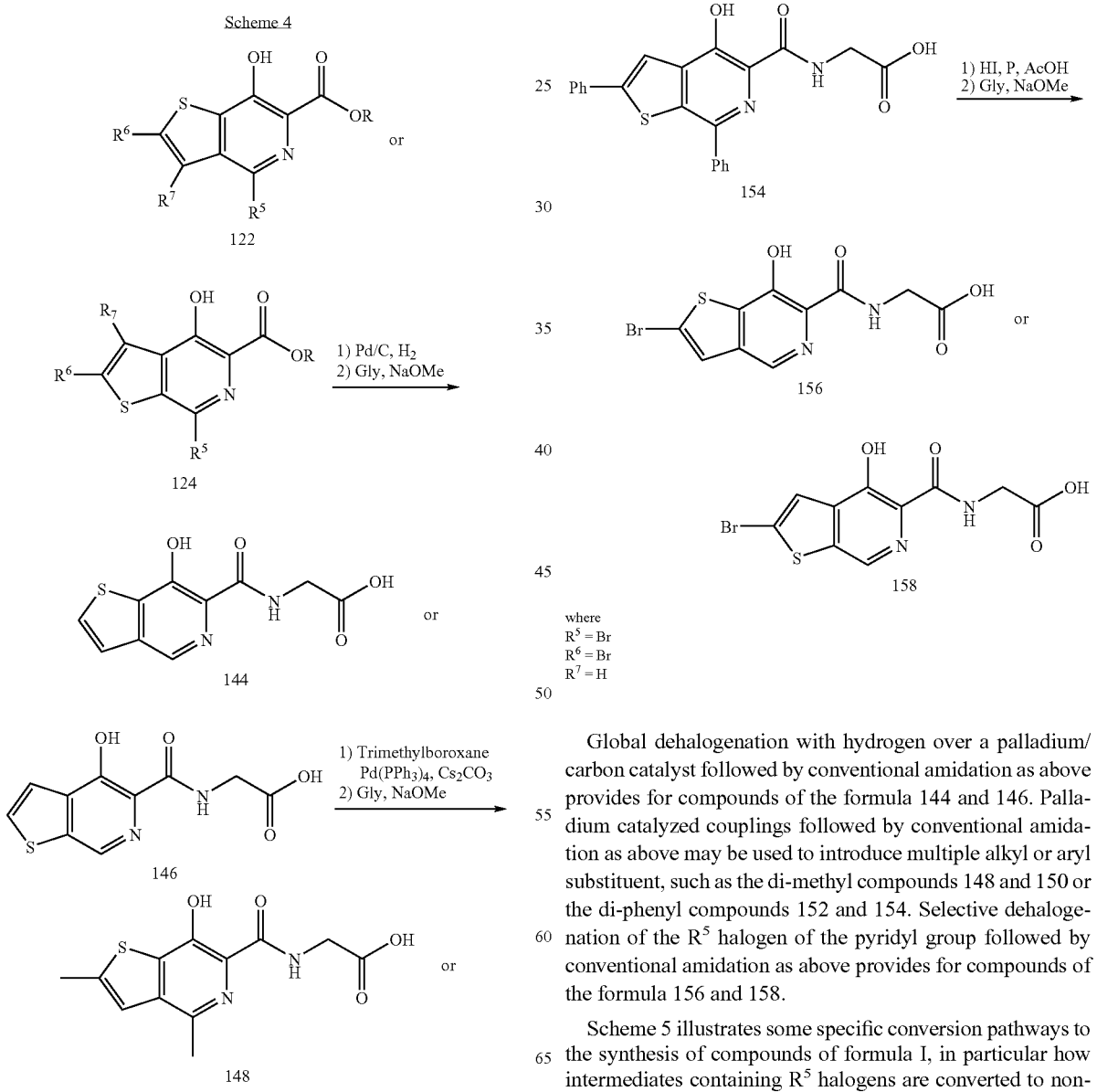

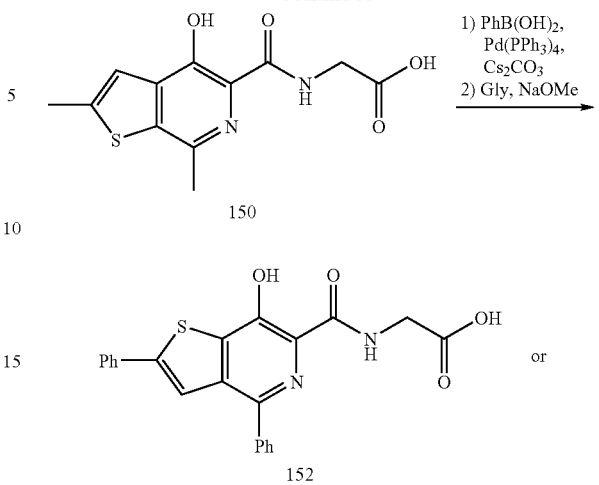

where
$R^5$ = Br
$R^6$ = Br
$R^7$ = H

Global dehalogenation with hydrogen over a palladium/carbon catalyst followed by conventional amidation as above provides for compounds of the formula 144 and 146. Palladium catalyzed couplings followed by conventional amidation as above may be used to introduce multiple alkyl or aryl substituent, such as the di-methyl compounds 148 and 150 or the di-phenyl compounds 152 and 154. Selective dehalogenation of the $R^5$ halogen of the pyridyl group followed by conventional amidation as above provides for compounds of the formula 156 and 158.

Scheme 5 illustrates some specific conversion pathways to the synthesis of compounds of formula I, in particular how intermediates containing $R^5$ halogens are converted to non-halogenated compounds.

Scheme 5

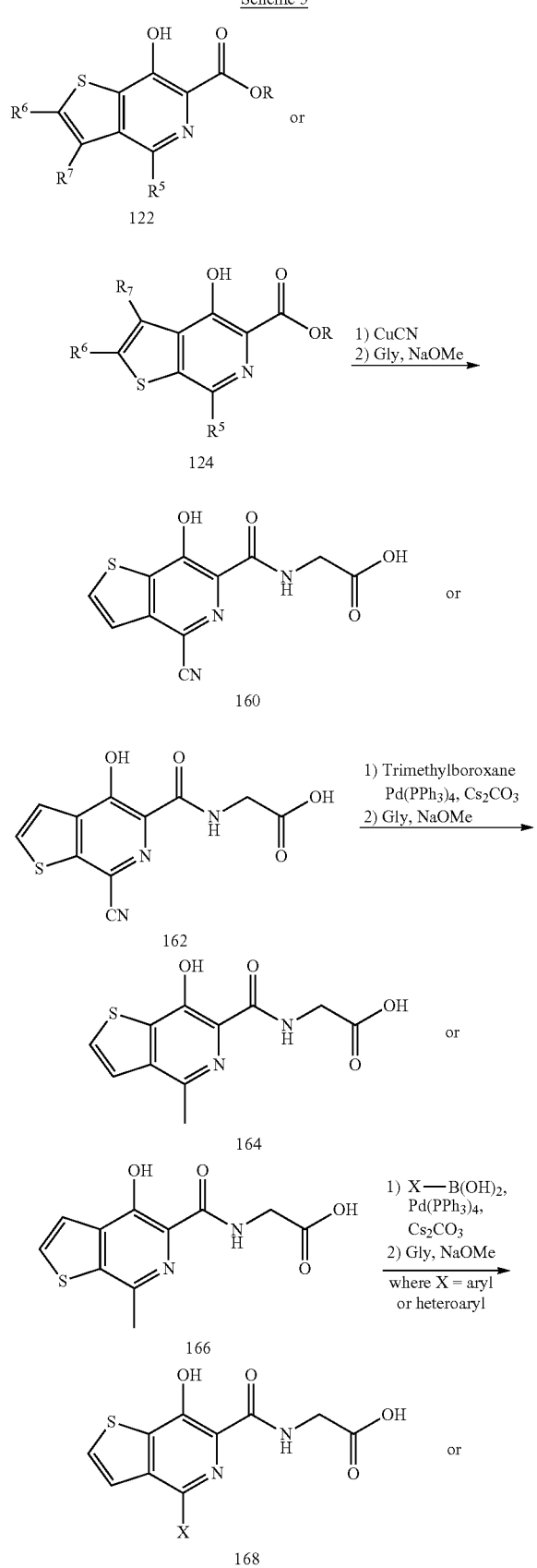

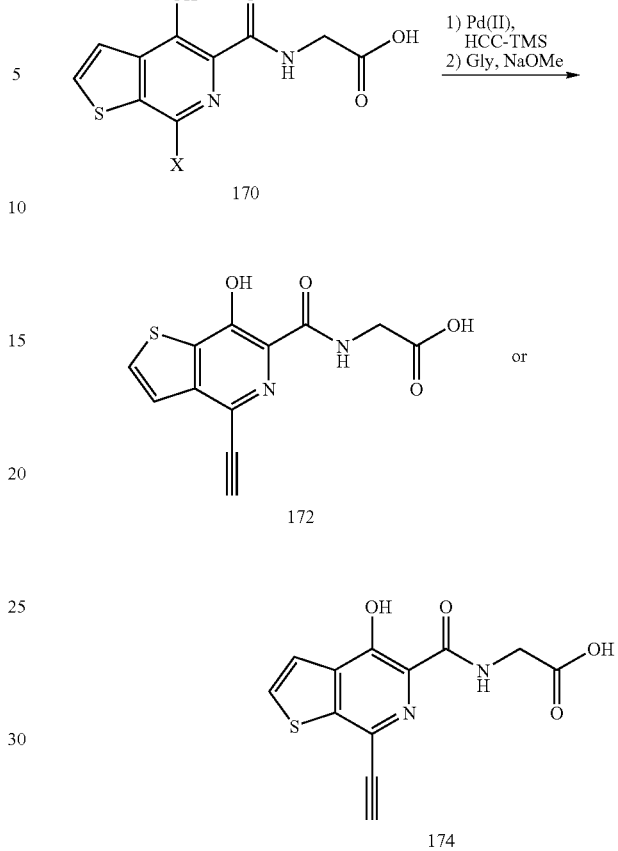

where
$R^5 = Br$
$R^6 = H$
$R^7 = H$

Compounds of the formula 122 and 124 where $R^5$ is a halogen, such as bromine, and $R^6$ and $R^7$ are hydrogen are readily transformed into non-halogen species using conventional methods. For example, treatment with appropriate nucleophilic species, such as copper cyanide, followed by conventional amidation methods are used to convert compounds 122 and 124 to compounds 160 and 162, respectively. Alternatively, treatment with the appropriate transition metal catalyst, such as Pd(0) or Pd(II) reagents, and an appropriate organo-metal species, for example organo tin reagents or organoborane reagents, illustrate conventional methods for the introduction of alkyl, alkenyl, alkynyl, aryl, and heteroaryl substituents at the $R^5$ position. Examples of such products are illustrated in scheme 5, where methyl, phenyl, substituted phenyl, 2-furanyl, 3-furanyl, 2-thienyl, 3-thienyl, and ethynyl substituents are illustrated within the scope of compounds 164, 166, 168, 170, 172, or 174. Hydrogenation, under standard conditions, of the alkynyl group, the corresponding alkenyl or alkyl compound can be provided.

Scheme 6 illustrates one example of a specific conversion pathway for the synthesis of compounds of formula I where intermediates containing halogens are converted to non-equivalent non-halogen substituents at $R^5$, $R^6$, and/or $R^7$.

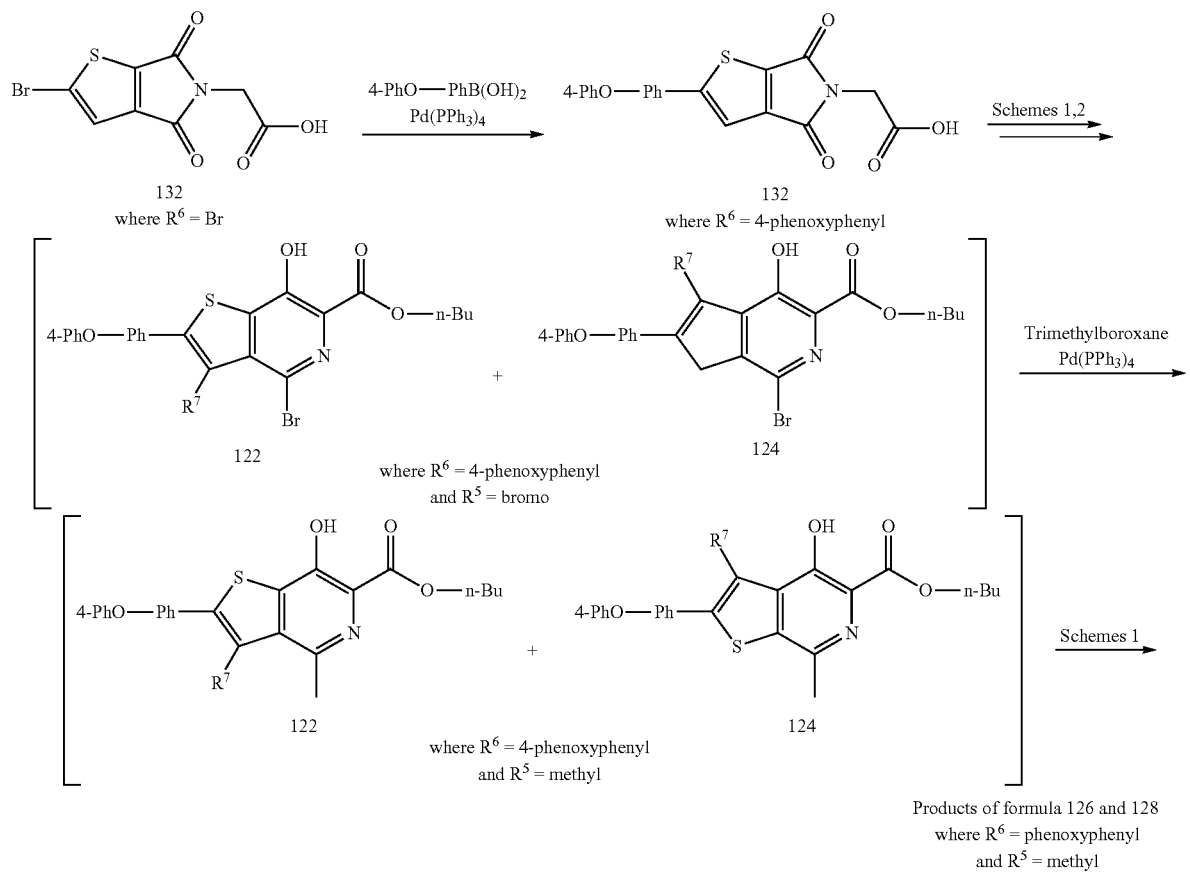

Intermediates along schemes 1-3 that contain mono halogenation may be transformed by numerous conventional methods into non-halogen based intermediates. For example, as illustrated in scheme 6 for $R^6$=4-phenoxyphenyl and $R^5$=methyl, intermediates of the formula 132 may be transformed by Suzuki coupling into intermediates of formula 132 where $R^6$=aryl or alkyl, which in turn may be converted to intermediates of formula 122 and 124 following the reaction sequences found in schemes 1 and 2. Intermediates of type 122 and 124 may then undergo a second Suzuki coupling to introduce, e.g., a methyl group at the $R^5$ position. Introduction of two independent halogen transforming reactions along general reaction schemes 1-3 allows for examples of formula I where, for example, $R^6$ and $R^5$ are not equal to halogen or hydrogen and are non-equivalent.

After derivatization of the 6-hydroxyl of the pyridyl group on any of the above compounds, derivatization of the 3-hydroxyl group can proceed via conventional methods. For example, reaction of compounds 122, 124, 126, or 128 with a strong base such as lithium diisopropylamide (LDA) provides for an anionic oxygen substituent. This intermediate is typically reacted in situ with a compound of the formula R'—Z (where R' and the 3-oxygen of the pyridyl group provide for the $R^1$ group of formula I, and Z is a leaving group such as a halide) to provide for ether linkages.

Ether linkages at the 6-position of the pyridyl group can also proceed in the above manner provided that the stoichiometry is controlled to facilitate either mono etherification (at the 6-position) or di-etherification (at the 3- and 6-positions).

Alternatively, amination of the 6-halide proceeds under conventional conditions by contact with ammonia, a primary amine or a secondary amine.

Further, oxidation of the sulfur atom in the thiophene ring to the corresponding sulfoxide or sulfone proceeds via conventional oxidation procedures including use of the appropriate stoichiometric amount of a suitable oxidizing agent such as m-chloroperbenzoic acid.

Other modifications to arrive at compounds of this invention are well within the skill of the art.

7. Use of Compounds of the Invention

The compounds of the present invention can be used to modulate the stability and/or activity of HIF, and thereby activate HIF-regulated gene expression. The compounds can be used in methods to treat, pretreat, or delay progression or onset of conditions associated with HIF including, but not limited to, anemic, ischemic, and hypoxic conditions. In various embodiments, the compound is administered immediately following a condition producing acute ischemia, e.g., myocardial infarction, pulmonary embolism, intestinal infarction, ischemic stroke, and renal ischemic-reperfusion injury. In another embodiment, the compound is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., UV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an UV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

8. Testing and Administration a. Biological Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 ml of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[1-$^{14}$C]-sodium salt Ketoglutaric acid-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, Methods Enzymol 82:245-304). Assay reactions contain 50 mM HEPES (pH 7.4), 100 µM α-ketoglutaric acid sodium salt, 0.30 µCi/ml ketoglutaric acid α-[1-$^{14}$C]-sodium salt, 40 µM $FeSO_4$, 1 mM ascorbate, 1541.8 units/ml Catalase, with or without 50 µM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

9. Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject having or at risk for anemia due to, e.g., chronic renal failure, diabetes, cancer, AIDS, radiation therapy, chemotherapy, kidney dialysis, or surgery. In a preferred embodiment, the subject is a mammalian subject, and in a most preferred embodiment, the subject is a human subject.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro-)suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and Ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

μl=Microliter
1-BuOH=1-butanol
aq.=Aqueous
Atm=Atmosphere
Brs=broad singlet
Ca.=circa
Conc.=concentrated
d=Doublet
DIEA=diisopropylethylamine
DMF=dimethyl formamide
DMF=dimethylfuran
DMSO=dimethyl sulfoxide
EtOAc=ethyl acetate
g=Gram
Gly=glycine
GlyOEt=glycine ethyl ester
h=Hour
Hz=Hertz
L=Liter
M=Molar
m=Multiplet
m/z=mass to charge ratio
MeOH=methanol
mg=Milligram
MHz=mega Hertz
min=Minute
mL=Milliliter
mmol=Millimolar
mol=Mole
N=Normal
NaOBu=sodium butoxide
NaOMe=sodium methoxide NMR=nuclear magnetic resonance
PSI=pound per square inch
q=quartet
R$_f$=retention factor
s=singlet
t=triplet
TEA=triethylamine
THF=tetrahydrofuran Example 1

[(2-Bromo-4-hydroxy-thieno[2,3-c]pyridine-5-carbonyl)-amino]-acetic acid a) 5-Bromo-3-methyl-thiophene-2-carbaldehyde Bromine (104 mL, 2.02 mol) was added dropwise to a 0° C. solution of 255 g of 3-methylthiophene-2-carboxaldehyde (2.02 mol) in 1.7 L of chloroform cooled with an external ice bath. After the addition was complete, the mixture was allowed to slowly warm to room temperature, and then heated at reflux temperature for 2 hours. The red mixture was diluted with 1 L methylene chloride and successively washed with water, saturated bicarbonate solution, and brine. The organic fraction was dried over anhydrous sodium sulfate and concentrated to a red oil. The crude oil was then vacuum distilled to isolate fractions which eluted at 101-106° C. at ca. 2 torr, which produced 301 g of a pale yellow-green solid. $^1$H NMR (CDCl$_3$, 200 MHz): δ=9.87 (s, 1H), 6.94 (s, 1H) 2.53 (s, 3H).

b) 5-Bromo-3-methyl-thiophene-2-carboxylic acid

A solution of 50.4 g of sodium phosphate, monobasic, (1.5 mol) in 600 mL of water, followed by 131 mL of a 35% hydrogen peroxide solution were added to a solution of 5-bromo-3-methyl-thiophene-2-carbaldehyde (300 g, 1.46 mol), example 1-a, in 1.5 L of acetonitrile. The resultant solution was cooled to 0° C. with an external ice bath, and a solution of 170 g of sodium perchlorite in 2 L of water was added dropwise over a 2 hour period. The reaction mixture was allowed to warm to room temperature, and stirred for 1.5 h. The reaction was quenched with the addition of 10 g of sodium sulfite, and stirred for 15 min. The mixture was acidified to ca. pH 3 with 1 N HCl solution, and cooled to 0° C. An off-white precipitate was collected on a medium glass filter funnel. The precipitate was washed twice with water and then dissolved in ethyl acetate. The aqueous acetonitrile solution was extracted once with ethyl acetate, and the organic fraction was combined with the pervious ethyl acetate solution. The combined organic fractions were dried over anhydrous magnesium sulfate and concentrated under hi-vacuum to produce 305 g of a tan solid. $^1$H NMR (CDCl$_3$, 200 MHz): δ=6.91 (s, 1H), 2.52 (s, 3H); MS: (-) m/z 218.92, 220.94 (M-1, $^{79}$Br/$^{81}$Br)

c) 5-Bromo-thiophene-2,3-dicarboxylic acid

A suspension of 5-bromo-3-methyl-thiophene-2-carboxylic acid (177 g, 0.80 mol), example 1-b, and sodium hydroxide (720 g, 18 mol) in 3 L of water was heated to 80° C. Potassium permanganate (513 g, 3.25 mol) was added in 25 g portions to the warm solution over 2-3 hours. The resultant suspension was heated to reflux temperature for 2 hours and then cooled to room temperature. The solid was filtered off and washed twice with 1 N NaOH and twice with water. The aqueous solution was acidified to pH <3 with concentrated sulfuric acid. The resulting white precipitate was collected on a medium fritted glass filter, washed twice with cold water, and dried under high vacuum to produce 112 g of a white solid. MS: (-) m/z 248.91, 250.98 (M-1, $^{79}$Br/$^{81}$Br)

d) (2-Bromo-4,6-dioxo-3a,4,6,6a-tetrahydro-thieno[2,3-c]pyrrol-5-yl)-acetic acid ethyl ester 5-Bromo-thiophene-2,3-dicarboxylic acid (3.1 g), example 1-c, was suspended in 13 mL of acetic anhydride and heated to reflux for 1.5 h, in which time the solid completely dissolved. The reaction mixture was concentrated under hi-vacuum and dried to a solid residue. The solid was suspended in 30 mL of anhydrous dichloromethane and cooled to 0° C. with an external ice bath. Triethylamine (5.2 mL) and glycine ethyl ester hydrochloride salt (2.6 g) were added slowly to the cold solution. The reaction mixture was warmed to room temperature and stirred for 16 h. The reaction mixture was diluted with ethyl acetate and washed successively with 1 N HCl and brine. The organic solution was dried over anhydrous sodium sulfate and concentrated to 3.7 g of a pale yellow solid under high vacuum.

The crude solid was suspended in 90 mL of anhydrous 1,4 dioxane. Thionyl chloride (8 mL) was added and the suspension was heated to reflux for 1.25 h. The solution was cooled and concentrated to a crude solid residue. The crude product was purified by flash chromatography eluting from silica gel with 3:7 ethyl acetate:hexanes to produce 2.3 g of a white solid. $^1$H NMR (CDCl$_3$, 200 MHz): δ=7.33 (s, 1H), 4.32 (s, 2H), 4.32-4.15 (q, J=7.02 Hz, 2H), 1.31-1.25 (t, J=7.02 Hz, 3H).

e) 2-Bromo-4,7-dihydroxy-thieno[2,3-c]pyridine-5-carboxylic acid butyl ester and 2-bromo-4,7-dihydroxy-thieno[3,2-c]pyridine-6-carboxylic acid butyl ester (2-Bromo-4,6-dioxo-3a,4,6,6a-tetrahydro-thieno[2,3-c]pyrrol-5-yl)-acetic acid ethyl ester (250 mg, 0.786 mmol), example 1-d, was added to 3 mL of 0.5 N sodium n-butoxide in n-butanol. The reaction mixture was heated at reflux temperature for 1.25 hours, cooled, and 8 mL of 0.5 N HCl was added to precipitate the desired products. The precipitate was collected on a fine glass filter funnel and washed twice with water. The crude product was dried and purified by column chromatography, eluting a mixture of the two products from silica gel with a gradient of 3-30% ethyl acetate in dichloromethane: 136 mg of a mixture of the title products were obtained. $^1$H NMR of ca. 1:1 mixture (d$_6$-DMSO, 200 MHz): δ=11.0 (br s, 2H), 10.29 (s, 1H), 10.24 (s, 1H), 7.74 (s, 1H), 7.70 (s, 1H), 4.33-4.27 (t, 4H), 1.75-1.64 (m, 4H), 1.46-1.35 (m, 4H), 0.95-0.92 (t, 6H).

f) 2-Bromo-7-chloro-4-hydroxy-thieno[2,3-c]pyridine-5-carboxylic acid butyl ester and 2-bromo-4-chloro-7-hydroxy-thieno[3,2-c]pyridine-6-carboxylic acid butyl ester A mixture of 2-bromo-4,7-dihydroxy-thieno[2,3-c]pyridine-5-carboxylic acid butyl ester and 2-bromo-4,7-dihydroxy-thieno[3,2-c]pyridine-6-carboxylic acid butyl ester (100 mg, 0.289 mmol), example 1-e, was suspended in 2 mL of anhydrous toluene. Phosphorous oxychloride (43 μL, 0.462 mmol) was added, and the reaction mixture was heated to 125° C. for 10 min. using a microwave reactor (CEM, Matthews, N.C.). The reaction mixture was diluted with 10 mL ethyl acetate and 10 mL of saturated sodium bicarbonate solution was added. The biphasic mixture was stirred for 15 min., filtered to remove insoluble materials, and separated to isolate the organic fraction. The organic fraction was washed with brine, dried over anhydrous sodium sulfate, and concentrated under high vacuum to yield 74 mg of the mixture of title compounds. $^1$H NMR of ca. 1:1 mixture (CDCl$_3$, 200 MHz): δ=11.50 (s, 1H), 11.48 (s, 1H), 7.69 (s, 1H), 7.52 (s, 1H), 4.50-4.37 (t, 7.0 Hz, 4H), 1.92-1.74 (m, 4H), 1.56-1.38 (m, 4H), 0.99-0.95 (t, J=7.4 Hz, 6H).

g) 2-Bromo-4-hydroxy-thieno[2,3-c]pyridine-5-carboxylic acid butyl ester (A) and 2-bromo-7-hydroxy-thieno[3,2-c]pyridine-6-carboxylic acid butyl ester (B)

A mixture (ca. 1:1) of 2-bromo-7-chloro-4-hydroxy-thieno[2,3-c]pyridine-5-carboxylic acid butyl ester and 2-bromo-4-chloro-7-hydroxy-thieno[3,2-c]pyridine-6-carboxylic acid butyl ester (70 mg, 0.192 mmol, example 1-f), red phosphorous (12 mg, 0.384 mmol), and 57% HI$_{(aq)}$ solution (43 µL, 0.576 mmol) in 1 mL of glacial acetic acid was heated at reflux temperature for 30 min. The reaction mixture was cooled, filtered through a celite pad which was then washed twice with dicloromethane, and the combined organic fractions were concentrated to a residue under high vacuum. The residue was dissolved in ethyl acetate and washed with a saturated sodium metabisulfite solution and a brine solution. The organic fraction was dried over anhydrous sodium sulfate and concentrated to a solid residue under high vacuum. The crude products were purified by flash chromatography eluting the two desired products with a gradient of 10-40% ethyl acetate in hexanes. Product A, first fraction, 7 mg; MS: (+) m/z 329.91, 331.90 (M+1, $^{79}$Br/81Br); Product B, second fraction, 8 mg, MS: (+) m/z 329.92, 331.91 (M+1, $^{79}$Br/$^{81}$Br)

h) [(2-Bromo-4-hydroxy-thieno[2,3-c]pyridine-5-carbonyl)-amino]-acetic acid

2-Bromo-4-hydroxy-thieno[2,3-c]pyridine-5-carboxylic acid butyl ester (7 mg, 0.020 mmol, example 1.g) and glycine (38 mg, 0.5 mmol) were suspended in 1 mL of 0.5 N sodium methoxide in methanol. The resultant mixture was heated to 120° C. for 10 min. using a CEM microwave reactor. The reaction mixture was cooled, concentrated to ca. 0.2 mL under high vacuum, and diluted with 1 mL of 1.0 N HCl. The resultant precipitate was collected on a fine glass filter funnel, washed twice with water, and dried under hi-vacuum to yield 7 mg of the title compound. MS: (−) m/z 328.98, 331.03 (M−1, $^{79}$Br/$^{81}$Br)

Example 2

[(2-Bromo-7-hydroxy-thieno[3,2-c]pyridine-6-carbonyl)-amino]-acetic acid

The title compound was prepared from 2-bromo-7-hydroxy-thieno[3,2-c]pyridine-6-carboxylic acid butyl ester (example 1-g-B), analogously to experimental example 1-h. MS: (−) m/z 328.95, 330.97 (M−1, $^{79}$Br/$^{81}$Br).

Example 3

{[4-Hydroxy-2-(4-methoxy-phenyl)-thieno[2,3-c]pyridine-5-carbonyl]-amino}-acetic acid a) [2-(4-Methoxy-phenyl)-4,6-dioxo-3a,4,6,6a-tetrahydro-thieno[2,3-c]pyrrol-5-yl]-acetic acid ethyl ester Under a nitrogen atmosphere, (2-bromo-4,6-dioxo-3a,4,6,6a-tetrahydro-thieno[2,3-c]pyrrol-5-yl)-acetic acid ethyl ester, example 1-d (431 mg, 1.35 mmol), 4-methoxy-phenyl boronic acid (309 mg, 2.0 mmol), cesium carbonate (1.10 g, 3.4 mmol), and tetrakis(triphenylphosphine)palladium(0) (157 mg, 0.14 mmol) were suspended in 8 mL of ethylene glycol dimethyl ether. The reaction mixture was heated at reflux temperature for 5 hours, cooled to room temperature, and diluted with ethyl acetate. The organic mixture was successively washed with saturated sodium bicarbonate and brine solutions. The organic fractions were dried over anhydrous sodium sulfate and concentrated to a crude solid residue, which was then purified by column chromatography, eluting the title compound from silica gel with a gradient of (5-30%) ethyl acetate in hexanes to yield 197 mg of a white solid. MS: (+) m/z 348.05 (M+1).

b) 4,7-Dihydroxy-2-(4-methoxy-phenyl)-thieno[2,3-c]pyridine-5-carboxylic acid butyl ester and 4,7-dihydroxy-2-(4-methoxy-phenyl)-thieno[3,2-c]pyridine-6-carboxylic acid butyl ester The title compound was prepared from [2-(4-methoxy-phenyl)-4,6-dioxo-3a,4,6,6a-tetrahydro-thieno[2,3-c]pyrrol-5-yl]-acetic acid ethyl ester, example 3-a, under conditions analogous to experimental example 1-e. MS: (+) m/z 374.00 (M+1).

c) 7-Chloro-4-hydroxy-2-(4-methoxy-phenyl)-thieno[2,3-c]pyridine-5-carboxylic acid butyl ester and 4-chloro-7-hydroxy-2-(4-methoxy-phenyl)-thieno[3,2-c]pyridine-6-carboxylic acid butyl ester The title compound was prepared from a mixture of 4,7-dihydroxy-2-(4-methoxy-phenyl)-thieno[2,3-c]pyridine-5-carboxylic acid butyl ester and 4,7-dihydroxy-2-(4-methoxy-phenyl)-thieno[3,2-c]pyridine-6-carboxylic acid butyl ester, example 3-b, under conditions analogous to experimental example 1-f. MS: (+) m/z 390.24, 392.19 (M+1, $^{35}$Cl/$^{37}$Cl).

d) 4-Hydroxy-2-(4-methoxy-phenyl)-thieno[2,3-c]pyridine-5-carboxylic acid butyl ester The title compound was prepared from a mixture of 7-chloro-4-hydroxy-2-(4-methoxy-phenyl)-thieno[2,3-c]pyridine-5-carboxylic acid butyl ester and 4-chloro-7-hydroxy-2-(4-methoxy-phenyl)-thieno[3,2-c]pyridine-6-carboxylic acid butyl ester, example 3-c, analogously to experimental conditions for example 1-g; with isolation of the lower R$_f$ isomer. MS: (+) m/z 358.05 (M+1).

e) {[4-Hydroxy-2-(4-methoxy-phenyl)-thieno[2,3-c]pyridine-5-carbonyl]-amino}-acetic acid 4-Hydroxy-2-(4-methoxy-phenyl)-thieno[2,3-c]pyridine-5-carboxylic acid butyl ester, example 3-d, (23 mg, 0.064 mmol) and glycine (63 mg, 0.64 mmol) were suspended in 1.3 mL of 0.5 N NaOMe in methanol. The reaction mixture was heated at reflux temperature for 16 hours, cooled, and diluted with 1 N HCl to precipitate out a white solid. The precipitate was collected on a fine glass fritted filter, washed twice with water, and dried under hi-vacuum to isolate 20 mg of the title compound. MS: (+) m/z 359.04 (M+1).

Example 4

{[7-Hydroxy-2-(4-methoxy-phenyl)-thieno[3,2-c]pyridine-6-carbonyl]-amino}-acetic acid a) 7-Hydroxy-2-(4-methoxy-phenyl)-thieno[3,2-c]pyridine-6-carboxylic acid butyl ester The title compound was prepared from a mixture of 7-chloro-4-hydroxy-2-(4-methoxy-phenyl)-thieno[2,3-c]pyridine-5-carboxylic acid butyl ester and 4-chloro-7-hydroxy-2-(4-methoxy-phenyl)-thieno[3,2-c]pyridine-6-carboxylic acid butyl ester, example 3-c, analogously to experimental conditions for example 1-g; with isolation of the higher R$_f$ isomer. MS: (+) m/z 358.05 (M+1).

b) {[7-Hydroxy-2-(4-methoxy-phenyl)-thieno[3,2-c]pyridine-6-carbonyl]-amino}-acetic acid The title compound was prepared from 7-hydroxy-2-(4-methoxy-phenyl)-thieno[3,2-c]pyridine-6-carboxylic acid butyl ester, example 4.a, under conditions analogous to experimental example 3-e. MS: (+) m/z 359.03 (M+1).

Example 5

[(4-Hydroxy-2,7-dimethyl-thieno[2,3-c]pyridine-5-carbonyl)-amino]-acetic acid a) 2,4-Dibromo-7-hydroxy-thieno[3,2-c]pyridine-6-carboxylic acid butyl ester and 2,7-dibromo-4-hydroxy-thieno[2,3-c]pyridine-5-carboxylic acid butyl ester A mixture of 2-bromo-4,7-dihydroxy-thieno[2,3-c]pyridine-5-carboxylic acid butyl ester and 2-bromo-4,7-dihydroxy-thieno[3,2-c]pyridine-6-carboxylic acid butyl ester (1.5 g, 4.3 mmol), example 1-e, were suspended in 20 mL of anhydrous toluene. Phosphorous oxybromide (1.85 g, 6.45 mmol) was added, and the reaction mixture was heated at 100° C. for 25 min. using a CEM microwave reactor. The reaction mixture was diluted with ethyl acetate, and saturated sodium bicarbonate solution was then added. The biphasic mixture was stirred for 15 min. and separated to isolate the organic fraction. The organic fraction was washed with brine, dried over anhydrous sodium sulfate, and concentrated under hi-vacuum to give 1.48 g of the mixture of title compounds. $^1$H NMR of ca. 1:1 mixture (CDCl$_3$, 200 MHz): δ=11.49 (s, 2H), 7.74 (s, 1H), 7.50 (s, 1H), 4.50-4.43 (t, J=7.0 Hz, 4H), 1.88-1.77 (m, 4H), 1.52-1.42 (m, 4H), 1.02-0.95 (t, J=7.02, 6H).

b) 4-Hydroxy-2,7-dimethyl-thieno[2,3-c]pyridine-5-carboxylic acid butyl ester (A) and 7-hydroxy-2,4-dimethyl-thieno[3,2-c]pyridine-6-carboxylic acid butyl ester (B)

Under a nitrogen atmosphere, a mixture of 2,4-dibromo-7-hydroxy-thieno[3,2-c]pyridine-6-carboxylic acid butyl ester and 2,7-dibromo-4-hydroxy-thieno[2,3-c]pyridine-5-carboxylic acid butyl ester (250 mg, 0.61 mmol, example 5-a), trimethylboroxane (230 mg, 1.83 mmol), potassium carbonate (422 mg, 3.05 mmol), and tetrakis(triphenylphosphine)palladium(0) (282 mg, 0.24 mmol) were suspended in 3 mL of anhydrous 1,4 dioxane. The reaction mixture was heated at 100° C. for 16 hours, cooled to room temperature, and diluted with ethyl acetate. The organic mixture was successively washed with water, saturated sodium bicarbonate, and brine solutions. The organic fractions were dried over anhydrous sodium sulfate and concentrated to a crude solid residue, which was then purified by column chromatography, eluting two major products from silica gel with a gradient of 15-60% ethyl acetate in hexanes: A (Higher R$_f$ product), 35 mg of white solid; MS: (−) m/z 278.23 (M−1); B (Lower R$_f$ product), 38 mg of pale yellow solid. $^1$H NMR (CDCl$_3$, 200 MHz): δ=11.36 (s, 1H), 7.10 (s, 1H), 4.51-4.43 (t, J=7.4 Hz, 2H), 2.73 (s, 3H) 2.67 (s, 3H), 1.90-1.83 (m, 2H), 1.53-1.42 (m, 2H), 1.02-0.95 (t, J=7.02, 3H).

c) [(4-Hydroxy-2,7-dimethyl-thieno[2,3-c]pyridine-5-carbonyl)-amino]-acetic acid 4-Hydroxy-2,7-dimethyl-thieno[2,3-c]pyridine-5-carboxylic acid butyl ester (30 mg, 0.11 mmol, example 5-b-A) and glycine (75 mg, 1.0 mmol) were suspended in 2.0 mL of 0.5 N NaOMe in methanol. The resultant mixture was heated to 120° C. for 10 min. using a CEM microwave reactor. The reaction mixture was cooled, and diluted with 0.25 N HCl until pH <3. The mixture was extracted two times with ethyl acetate, and the organic fractions were dried over anhydrous magnesium sulfate and concentrated to 27 mg of a pale yellow solid. MS: (−) m/z 279.01 (M−1).

Example 6

[(7-Hydroxy-2,4-dimethyl-thieno[3,2-c]pyridine-6-carbonyl)-amino]-acetic acid

The title compound was prepared from 7-hydroxy-2,4-dimethyl-thieno[3,2-c]pyridine-6-carboxylic acid butyl ester, example 5-b-B, under conditions analogous to experimental example 5-c. The final product was further purified by trituration with methanol to provide the pure title compound. MS: (−) m/z 279.06 (M−1).

Example 7

{[7-Hydroxy-4-methyl-2-(4-phenoxy-phenyl)-thieno[3,2-c]pyridine-6-carbonyl]-amino}-acetic acid a) [2-(4-Phenoxy-phenyl)-4,6-dioxo-3a,4,6,6a-tetrahydro-thieno[2,3-c]pyrrol-5-yl]-acetic acid ethyl ester The title compound was prepared from (2-bromo-4,6-dioxo-3a,4,6,6a-tetrahydro-thieno[2,3-c]pyrrol-5-yl)-acetic acid ethyl ester, example 1-d, and 4-phenoxy-phenyl boronic acid under conditions analogous to experimental example 3-a. $^1$H NMR (CDCl$_3$, 200 MHz): δ=7.58-7.54 (d, J=8.97 Hz, 2H), 7.41-7.34 (m, 3H), 7.20-7.0 (m, 4H), 4.35 (s, 2H), 4.27-4.17 (q, J=7.0, 2H), 1.32-1.25 (t, J=7.0 Hz, 3H).

b) 4,7-Dihydroxy-2-(4-phenoxy-phenyl)-thieno[2,3-c]pyridine-5-carboxylic acid butyl ester and 4,7-dihydroxy-2-(4-phenoxy-phenyl)-thieno[3,2-c]pyridine-6-carboxylic acid butyl ester The title compound was prepared from [2-(4-phenoxy-phenyl)-4,6-dioxo-3a,4,6,6a-tetrahydro-thieno[2,3-c]pyrrol-5-yl]-acetic acid ethyl ester, example 7-a, under conditions analogous to example 1-e. The crude precipitate from this reaction mixture did not require further purification. MS: (+) m/z 346.03 (M+1).

c) 4-Bromo-7-hydroxy-2-(4-phenoxy-phenyl)-thieno[3,2-c]pyridine-6-carboxylic acid butyl ester and 7-bromo-4-hydroxy-2-(4-phenoxy-phenyl)-thieno[2,3-c]pyridine-5-carboxylic acid butyl ester The title compound was prepared from a mixture of 4,7-dihydroxy-2-(4-phenoxy-phenyl)-thieno[2,3-c]pyridine-5-carboxylic acid butyl ester and 4,7-dihydroxy-2-(4-phenoxy-phenyl)-thieno[3,2-c]pyridine-6-carboxylic acid butyl ester, example 7-b, under conditions analogous to experimental example 5-a. The title compounds were further purified by column chromatography, eluting as a mixture from silica gel with a gradient of 10-30% ethyl acetate in hexanes. $^1$H NMR of ca. 1:1 mixture (CDCl$_3$, 200 MHz): δ=11.53 (s, 1H), 11.50 (s, 1H), 7.8-7.0 (m, 18H), 4.51-4.34 (t, 7.4 Hz, 4H), 1.90-1.82 (m, 4H), 1.54-1.45 (m, 4H), 0.99-0.95 (t, J=7.8 Hz, 6H).

d) 4-Hydroxy-2-(4-phenoxy-phenyl)-7-methyl-thieno[2,3-c]pyridine-5-carboxylic acid butyl ester (A) and 7-hydroxy-2-(4-phenoxy-phenyl)-4-methyl-thieno[3,2-c]pyridine-6-carboxylic acid butyl ester (B)

Under a nitrogen atmosphere, a mixture of 4-bromo-7-hydroxy-2-(4-phenoxy-phenyl)-thieno[3,2-c]pyridine-6-carboxylic acid butyl ester and 7-bromo-4-hydroxy-2-(4-phenoxy-phenyl)-thieno[2,3-c]pyridine-5-carboxylic acid butyl ester (108 mg, 0.217 mmol), example 7-c, trimethylboroxane (41 mg, 0.33 mmol), potassium carbonate (105 mg, 0.76 mmol), and tetrakis(triphenylphosphine)palladium(0) (52 mg, 0.045 mmol) were suspended in 1.1 mL of anhydrous 1,4 dioxane. The reaction mixture was heated at 70° C. for 40 hours, cooled to room temperature, and diluted with ethyl acetate. The organic mixture was successively washed with water, saturated sodium bicarbonate, and brine solutions. The organic fractions were dried over anhydrous sodium sulfate and concentrated to a crude oily residue, which was then purified by column chromatography, eluting two major products from silica gel with a gradient of 10-50% ethyl acetate in hexanes: A (Higher R$_f$ product), 7 mg; MS: (−) m/z 432.30 (M−1); B (Lower R$_f$ product), 11 mg; MS: (−) m/z 432.35 (M−1).

e) {[7-Hydroxy-4-methyl-2-(4-phenoxy-phenyl)-thieno[3,2-c]pyridine-6-carbonyl]-amino}-acetic acid The title compound was prepared from 7-hydroxy-2-(4-phenoxy-phenyl)-4-methyl-thieno[3,2-c]pyridine-6-carboxylic acid butyl ester, example 7-d-B, under conditions analogous to example 5-c. MS: (−) m/z 433.11 (M−1).

Example 8

{[4-Hydroxy-2-(4-phenoxy-phenyl)-7-methyl-thieno[2,3-c]pyridine-5-carbonyl]-amino}-acetic acid The title compound was prepared from 4-hydroxy-2-(4-phenoxy-phenyl)-7-methyl-thieno[2,3-c]pyridine-5-carboxylic acid butyl ester, example 7-d-A, under conditions analogous to example 5-c. MS: (−) m/z 433.11 (M−1).

Example 9

{[4-Hydroxy-2-(4-phenoxy-phenyl)-thieno[2,3-c]pyridine-5-carbonyl]-amino}-acetic acid a) 4-Hydroxy-2-(4-phenoxy-phenyl)-thieno[2,3-c]pyridine-5-carboxylic acid butyl ester The title compound was prepared from a mixture of 4-bromo-7-hydroxy-2-(4-phenoxy-phenyl)-thieno[3,2-c]pyridine-6-carboxylic acid butyl ester and 7-bromo-4-hydroxy-2-(4-phenoxy-phenyl)-thieno[2,3-c]pyridine-5-carboxylic acid butyl ester, example 7-c, under conditions analogous to experimental example 13-a with isolation of the lower R$_f$ isomer. MS: (+) m/z 420.06 (M+1).

b) {[4-Hydroxy-2-(4-phenoxy-phenyl)-thieno[2,3-c]pyridine-5-carbonyl]-amino}-acetic acid The title compound was prepared from 4-hydroxy-2-(4-phenoxy-phenyl)-thieno[2,3-c]pyridine-5-carboxylic acid butyl ester, example 9.a, under conditions analogous to experimental example 5-c. MS: (+) m/z 421.01 (M+1).

Example 10

{[7-Hydroxy-2-(4-phenoxy-phenyl)-thieno[3,2-c]pyridine-6-carbonyl]-amino}-acetic acid a) 7-Hydroxy-2-(4-phenoxy-phenyl)-thieno[3,2-c]pyridine-6-carboxylic acid butyl ester The title compound was prepared from a mixture of 4-bromo-7-hydroxy-2-(4-phenoxy-phenyl)-thieno[3,2-c]pyridine-6-carboxylic acid butyl ester and 7-bromo-4-hydroxy-2-(4-phenoxy-phenyl)-thieno[2,3-c]pyridine-5-carboxylic acid butyl ester, example 7-c, under conditions analogous to experimental example 13-a with isolation of the higher R$_f$ isomer. MS: (+) m/z 420.03 (M+1).

b) {[7-Hydroxy-2-(4-phenoxy-phenyl)-thieno[3,2-c]pyridine-6-carbonyl]-amino}-acetic acid The title compound was prepared from 7-hydroxy-2-(4-phenoxy-phenyl)-thieno[3,2-c]pyridine-6-carboxylic acid butyl ester, example 10-a, under conditions analogous to experimental example 5-c. MS: (+) m/z 421.00 (M+1).

Example 11

[(2,7-Dibromo-4-hydroxy-thieno[2,3-c]pyridine-5-carbonyl)-amino]-acetic acid a) 5-Bromo-thiophene-2,3-dicarboxylic acid dimethyl ester 5-Bromo-thiophene-2,3-dicarboxylic acid (124 g, 0.49 mol), example 1-c, was suspended in 750 mL of thionyl chloride and heated to reflux temperature for 1 hour. The solution was cooled and concentrated to a solid residue under hi-vacuum. The crude solid was suspended in 2.5 L of cold methanol, and heated to reflux temperature for 4 hours. The resultant mixture was filtered to remove trace solid, and concentrated to ca. 500 mL under reduced pressure. The solution was diluted with ethyl acetate and successively washed with water, bicarbonate solution, and brine. The organic fraction was dried over anhydrous magnesium sulfate and concentrated to 101 g of a tan liquid. MS (+): 278.77, 280.80 (M+1, $^{79}$Br/$^{81}$Br).

b) 5-Bromo-thiophene-2,3-dicarboxylic acid 3-methyl ester and 5-bromo-thiophene-2,3-dicarboxylic acid 2-methyl ester 5-Bromo-thiophene-2,3-dicarboxylic acid dimethyl ester (124 g, 444 mmol) was dissolved in 888 mL of methanol and cooled to 0° C. with an external ice bath. A solution of 222 mL of 2 N NaOH was added dropwise to the cold solution and stirred at 0° C. for 2 h. The reaction mixture was concentrated to ca. 300 mL and partitioned between 0.5 N HCl and ethyl

47 acetate and extracted with ethyl acetate twice. The organic fractions were washed once with acidic brine solution, dried over anhydrous magnesium sulfate, and concentrated to a solid residue. The crude residue was triturated with 200 mL of hexanes and dried under hi-vacuum to 112 g of a tan solid. MS (+): 264.84, 266.86 (M+1, $^{79}$Br/$^{81}$Br).

c) 2-Bromo-4,7-dihydroxy-thieno[2,3-c]pyridine-5-carboxylic acid butyl ester (A) and 2-bromo-4,7-dihydroxy-thieno[3,2-c]pyridine-6-carboxylic acid butyl ester (B)

A mixture of 5-bromo-thiophene-2,3-dicarboxylic acid 3-methyl ester and 5-bromo-thiophene-2,3-dicarboxylic acid 2-methyl ester (110 g, 415 mmol) was dissolved in 500 mL THF and cooled to 0° C. Oxalyl chloride (54.2 mL, 0.622 mol) and DMF (1 mL) were added and the reaction mixture was stirred at 0° C. for 15 min and then allowed to warm to room temperature and stirred for 1 hour. The solution was concentrated to a residue under hi-vacuum and re-dissolved in 200 mL of 1,4 dioxane. The solution was cooled to 0° C. with an external ice bath, and a suspension of glycine ethyl ester hydrochloride salt (86.5 g, 622 mmol) and triethylamine (173 mL, 1.24 mol) in 300 mL of 1:1 DMF:1,4 dioxane was added. The ice bath was removed and 300 mL of 1,4 dioxane was added. The reaction mixture was stirred for 2.5 hours, diluted with ethyl acetate, and washed successively with two portions of 0.5 N HCl, water, saturated bicarbonate solution, and brine. The organic fraction was dried over sodium sulfate and concentrated to 100 g of crude solid. The crude solid was partially purified by column chromatography, eluting the desired products from silica gel with 30% ethyl acetate in hexanes to give 80 g of tan solid.

A portion of the crude intermediate (10 g, 28.6 mmol) was added to 120 mL of 0.5 N sodium n-butoxide in n-butanol. The reaction mixture was heated at reflux temperature for 45 min, cooled, and 70 mL of 1 N HCl, 50 ml water and 20 mL ethyl acetate was added to precipitate the desired products. The precipitate was collected on a fine glass filter funnel and washed twice with water and twice with ethyl acetate to give 6.0 g of a mixture of 2-bromo-4,7-dihydroxy-thieno[2,3-c]pyridine-5-carboxylic acid butyl ester and 2-bromo-4,7-dihydroxy-thieno[3,2-c]pyridine-6-carboxylic acid butyl ester. MS (+): 345.95, 347.94 (M+1, $^{79}$Br/$^{81}$Br).

A portion of the product mixture was separated by column chromatography, where a careful elution of the two isomers from silica gel with a gradient of 0-20% ethyl acetate in dichloromethane provided pure products: (A) 2-Bromo-4,7-dihydroxy-thieno[2,3-c]pyridine-5-carboxylic acid butyl ester, higher $R_f$ isomer; $^1$H NMR (d$_6$-DMSO, 200 MHz): δ=11.12 (br s, 1H), 10.28 (br s, 1H), 7.74 (s, 1H), 4.33-4.27 (t, J=6.3 Hz, 2H), 1.78-1.64 (m, 2H), 1.50-1.32 (m, 2H), 0.96-0.88 (t, J=7.4 Hz, 3H); (B) 2-Bromo-4,7-dihydroxy-thieno[3,2-c]pyridine-6-carboxylic acid butyl ester, lower $R_f$ isomer; $^1$H NMR (d$_6$-DMSO, 200 MHz): δ=10.95 (br s, 1H), 10.24 (br s, 1H), 7.69 (s, 1H), 4.33-4.27 (t, J=6.3 Hz, 2H), 1.74-1.64 (m, 2H), 1.46-1.35 (m, 2H), 0.96-0.88 (t, J=7.0 Hz, 3H).

d) 2,7-Dibromo-4-hydroxy-thieno[2,3-c]pyridine-5-carboxylic acid butyl ester

The title compound was prepared from 2-bromo-4,7-dihydroxy-thieno[2,3-c]pyridine-5-carboxylic acid butyl ester, example 11.c-A, under conditions analogous to experimental example 5-a. $^1$H NMR (CDCl$_3$, 200 MHz): δ=11.49 (s, 1H), 7.74 (s, 1H), 4.50-4.46 (t, 2H), 1.91-1.84 (m, 2H), 1.57-1.41 (m, 2H), 1.02-0.95 (t, 3H).

48 e) [(2,7-Dibromo-4-hydroxy-thieno[2,3-c]pyridine-5-carbonyl)-amino]-acetic acid

The title compound was prepared from 2,7-dibromo-4-hydroxy-thieno[2,3-c]pyridine-5-carboxylic acid butyl ester, example 11-d, under conditions analogous to experimental example 1-h. MS (−): 406.94, 408.96, 410.96 (M−1, $^{79}$Br/$^{81}$Br).

Example 12

[(2-Bromo-7-chloro-4-hydroxy-thieno[2,3-c]pyridine-5-carbonyl)-amino]-acetic acid a) 2-Bromo-7-chloro-4-hydroxy-thieno[2,3-c]pyridine-5-carboxylic acid butyl ester The title compound was prepared from 2-bromo-4,7-dihydroxy-thieno[2,3-c]pyridine-5-carboxylic acid butyl ester, example 11.c-A, under conditions analogous to experimental example 1-f. $^1$H NMR (CDCl$_3$, 200 MHz): δ=11.50 (s, 1H), 7.67 (s, 1H), 4.50-4.43 (t, 2H), 1.91-1.80 (m, 2H), 1.58-1.41 (m, 2H), 1.02-0.95 (t, 3H).

b) [(2-Bromo-7-chloro-4-hydroxy-thieno[2,3-c]pyridine-5-carbonyl)-amino]-acetic acid The title compound was prepared from 2-bromo-7-chloro-4-hydroxy-thieno[2,3-c]pyridine-5-carboxylic acid butyl ester, example 12-a, under conditions analogous to experimental example 1-h. MS (−): 363.00, 365.00, 366.98 (M−1, $^{79}$Br/$^{81}$Br-$^{35}$Cl/$^{37}$Cl).

Example 13

[(7-Hydroxy-thieno[3,2-c]pyridine-6-carbonyl)-amino]-acetic acid a) 4-Hydroxy-thieno[2,3-c]pyridine-5-carboxylic acid butyl ester (A) and 7-hydroxy-thieno[3,2-c]pyridine-6-carboxylic acid butyl ester (B)

A mixture of 2,4-dibromo-7-hydroxy-thieno[3,2-c]pyridine-6-carboxylic acid butyl ester and 2,7-dibromo-4-hydroxy-thieno[2,3-c]pyridine-5-carboxylic acid butyl ester (165 mg, 0.40 mmol), example 5-a, was dissolved in 7 mL of 1:1 methanol: ethyl acetate. Sodium acetate (100 mg, 1.2 mmol) and 10% palladium on carbon (115 mg) were added, and the mixture was shaken under a H$_2$ atmosphere at 20 PSI for 5 hours. The mixture was filtered through a pad of celite and concentrated to a crude residue. The crude products were purified by column chromatography eluting the two products from silica gel with a gradient of 10-50% ethyl acetate in hexanes. A, Higher $R_f$ isomer: 29 mg; MS (+): 252.00 (M+1); B, Lower $R_f$ isomer: 31 mg; MS (+): 252.01 (M+1).

b) [(7-Hydroxy-thieno[3,2-c]pyridine-6-carbonyl)-amino]-acetic acid

The title compound was prepared from 7-hydroxy-thieno[3,2-c]pyridine-6-carboxylic acid butyl ester, example 13.a-B, under conditions analogous to experimental example 1.h; MS (+): 253.05 (M+1)

Example 14

[(4-Hydroxy-thieno[2,3-c]pyridine-5-carbonyl)-amino]-acetic acid

The title compound was prepared from 4-hydroxy-thieno[2,3-c]pyridine-5-carboxylic acid butyl ester, example 13-a-A, under conditions analogous to experimental example 1-h. MS (−): 251.09 (M−1)

Example 15

[(2-Bromo-4-chloro-7-hydroxy-thieno[3,2-c]pyridine-6-carbonyl)-amino]-acetic acid a) 2-Bromo-4-chloro-7-hydroxy-thieno[3,2-c]pyridine-6-carboxylic acid butyl ester The title compound was prepared from 2-bromo-4,7-dihydroxy-thieno[3,2-c]pyridine-6-carboxylic acid butyl ester, example 11-c-B, under conditions analogous to experimental example 1-f. MS (−): 362.06, 364.20, 366.26 (M−1, $^{79}$Br/$^{81}$Br-$^{35}$Cl/$^{37}$Cl).

b) [(2-Bromo-4-chloro-7-hydroxy-thieno[3,2-c]pyridine-6-carbonyl)-amino]-acetic acid The title compound was prepared from 2-bromo-4-chloro-7-hydroxy-thieno[3,2-c]pyridine-6-carboxylic acid butyl ester, example 15-a, under conditions analogous to experimental example 1-h. MS (−): 362.96, 364.93, 366.99 (M−1, $^{79}$Br/$^{81}$Br-$^{35}$Cl/$^{37}$Cl).

Example 16

[(2,4-Dibromo-7-hydroxy-thieno[3,2-c]pyridine-6-carbonyl)-amino]-acetic acid a) 2,4-Dibromo-7-hydroxy-thieno[3,2-c]pyridine-6-carboxylic acid butyl ester The title compound was prepared from 2-bromo-4,7-dihydroxy-thieno[3,2-c]pyridine-6-carboxylic acid butyl ester, example 11-e-B, under conditions analogous to experimental example 5-a. MS (−): 406.18, 408.15, 410.20 (M−1, $^{79}$Br/$^{81}$Br).

b) [(2,4-Dibromo-7-hydroxy-thieno[3,2-c]pyridine-6-carbonyl)-amino]-acetic acid The title compound was prepared from 2,4-dibromo-7-hydroxy-thieno[3,2-c]pyridine-6-carboxylic acid butyl ester, example 16-a, under conditions analogous to experimental example 1-h. MS (−): 406.95, 408.97, 410.97 (M−1, $^{79}$Br/$^{81}$Br).

Example 17

[(7-Hydroxy-2-phenylsulfanyl-thieno[3,2-c]pyridine-6-carbonyl)-amino]-acetic acid a) 4,7-Dihydroxy-2-phenylsulfanyl-thieno[3,2-c]pyridine-6-carboxylic acid n-butyl ester and 4,7-dihydroxy-2-phenylsulfanyl-thieno[2,3-c]pyridine-5-carboxylic acid n-butyl ester A mixture of 2-bromo-4,7-dihydroxy-thieno[3,2-c]pyridine-6-carboxylic acid n-butyl ester and 2-bromo-4,7-dihydroxy-thieno[2,3-c]pyridine-5-carboxylic acid n-butyl ester, example 1.e, (750 mg, 2.16 mmol) suspended in 1.5 mL of benzenethiol was heated to 145° C. for 45 minutes using a CEM microwave reactor. The mixture was concentrated under high vacuum. The residue was purified by flash chromatography, eluting fractions of a mixture containing the desired products and starting materials with a gradient of 0-20% ethyl acetate in dichloromethane, 336 mg of a tan oil; MS(+) m/z 375.98 (M+1)

b) 4-Bromo-7-hydroxy-2-phenylsulfanyl-thieno[3,2-c]pyridine-6-carboxylic acid n-butyl ester and 7-bromo-4-hydroxy-2-phenylsulfanyl-thieno[2,3-c]pyridine-5-carboxylic acid n-butyl ester The title compound was prepared from a mixture of 4,7-dihydroxy-2-phenylsulfanyl-thieno[3,2-c]pyridine-6-carboxylic acid n-butyl ester and 4,7 dihydroxy-2-phenylsulfanyl-thieno[2,3-c]pyridine-5-carboxylic acid n-butyl ester, example 17.a, under conditions analogous to experimental conditions 5.a. The products were obtained as a mixture of the two isomers; MS: (+) m/z 437.91, 439.91 (M+1, $^{79}$Br/$^{81}$Br).

c) 7-Hydroxy-2-phenylsulfanyl-thieno[3,2-c]pyridine-6-carboxylic acid n-butyl ester (A) and 4-hydroxy-2-phenylsulfanyl-thieno[2,3-c]pyridine-5-carboxylic acid n-butyl ester (B)

The title compound was prepared from a mixture of 4-bromo-7-hydroxy-2-phenylsulfanyl-thieno[3,2-c]pyridine-6-carboxylic acid n-butyl ester and 7-bromo-4-hydroxy-2-phenylsulfanyl-thieno[2,3-c]pyridine-5-carboxylic acid n-butyl ester, example 17.b, under conditions analogous to experimental example 1.g. The products were purified by column chromatography eluting from silica gel with a gradient of 20-60% ethyl acetate in hexanes. Product A, (Lower $R_f$ product); MS: (+) m/z 360.01 (M+1); Product B, (Higher $R_f$ product); MS: (+) m/z 360.02 (M+1).

d) [(7-Hydroxy-2-phenylsulfanyl-thieno[3,2-c]pyridine-6-carbonyl)-amino]-acetic acid 7-Hydroxy-2-phenylsulfanyl-thieno[3,2-c]pyridine-6-carboxylic acid n-butyl ester, example 17.c.A, (25 mg, 0.07 mmol) and glycine (52 mg, 0.7 mmol) were suspended in 1.4 mL of 0.5 N NaOMe in methanol. The reaction mixture was heated at 120° C. for 10 minutes using a CEM microwave reactor, cooled, and diluted with 0.25 N HCl to precipitate out a white solid. The precipitate was collected on a fine glass fritted filter, washed twice with water, and dried under hi-vacuum to isolate 23 mg of the title compound. MS: (+) m/z 361.4 (M+1).

Example 18

[(4-Hydroxy-2-phenylsulfanyl-thieno[2,3-c]pyridine-5-carbonyl)-amino]-acetic acid The title compound was prepared from 4-hydroxy-2-phenylsulfanyl-thieno[2,3-c]pyridine-5-carboxylic acid n-butyl ester, example 17.c.B, under conditions analogous to experimental example 17.d; MS: (+) m/z 361.3 (M+1)

Example 19

[(4-Hydroxy-2,7-diphenyl-thieno[2,3-c]pyridine-5-carbonyl)-amino]-acetic acid a) 4-Hydroxy-2,7-diphenyl-thieno[2,3-c]pyridine-5-carboxylic acid butyl ester (A) and 7-hydroxy-2,4-diphenyl-thieno[3,2-c]pyridine-6-carboxylic acid butyl ester (B)

Under a nitrogen atmosphere a mixture of 2,4-dibromo-7-hydroxy-thieno[3,2-c]pyridine-6-carboxylic acid butyl ester and 2,7-dibromo-4-hydroxy-thieno[2,3-c]pyridine-5-carboxylic acid butyl ester (150 mg, 0.366 mmol, example 5-a), phenylboronic acid (133 mg, 1.09 mmol), cesium carbonate (475 mg, 1.46 mmol), and tetrakis(triphenylphosphine)palladium(0) (58 mg, 0.05 mmol) were suspended in 1.8 mL of anhydrous 1,4 dioxane. The reaction mixture was heated at 120° C. for 20 minutes in a CEM microwave reactor, cooled to room temperature, and diluted with ethyl acetate. The organic mixture was successively washed with water, saturated sodium bicarbonate, and brine solutions. The organic fractions were dried over anhydrous sodium sulfate and concentrated to a crude solid residue, which was then purified by column chromatography eluting two major products from silica gel with a gradient of 0-20% ethyl ether in toluene to isolate the desired products. A (Higher $R_f$ product) MS: (+) m/z 404.60 (M+1); B (Lower $R_f$ product) MS: (+) m/z 404.53 (M+1)

b) [(4-Hydroxy-2,7-diphenyl-thieno[2,3-c]pyridine-5-carbonyl)-amino]-acetic acid The title compound was prepared from 4-hydroxy-2,7-diphenyl-thieno[2,3-c]pyridine-5-carboxylic acid n-butyl ester, example 19.a.A, under conditions analogous to experimental example 17.d; MS: (+) m/z 405.38 (M+1)

Example 20

[(7-Hydroxy-2,4-diphenyl-thieno[3,2-c]pyridine-6-carbonyl)-amino]-acetic acid The title compound was prepared from 7-hydroxy-2,4-diphenyl-thieno[3,2-c]pyridine-6-carboxylic acid butyl ester, example 19.a.B, under conditions analogous to experimental example 17.d; MS: (+) m/z 405.20 (M+1)

Example 21

[(7-Hydroxy-2-styryl-thieno[3,2-c]pyridine-6-carbonyl)-amino]-acetic acid a) 5-Bromo-3-methyl-thiophene-2-carboxylic acid ethyl ester

5-Bromo-3-methyl-thiophene-2-carboxylic acid (example 1.b, 10.0 g, 45.2 mmol) was suspended in 40 mL of thionyl chloride. The mixture was heated at reflux temperature for 1 hour and then cooled to 0° C. with an external ice bath. Cold ethyl alcohol (150 mL) was carefully added, and the solution was heated at reflux temperature for 16 hours. Under reduced pressure, the solution was concentrated to ca. one third of the original volume and then diluted with ethyl acetate and washed successively twice with saturated sodium bicarbonate solution, and once with brine. The organic fractions were dried over anhydrous sodium sulfate and concentrated to 7.9 g of a yellow oil: $^1$H NMR (CDCl$_3$, 200 MHz): δ=6.87 (s, 1H), 4.34-4.23 (q, 1H, J=7.0 Hz), 2.50 (s, 3H), 1.39-1.32 (t, 3H, J=7.0 Hz).

b) 5-Bromo-3-{[(2,4-dimethoxy-benzyl)-ethoxycarbonylmethyl-amino]-methyl}-thiophene-2-carboxylic acid ethyl ester 5-Bromo-3-methyl-thiophene-2-carboxylic acid ethyl ester (example 21.a, 5.0 g, 20.0 mmol), N-bromosuccinimide (3.65 g, 20.5 mmol), and benzoyl peroxide (484 mg, 2.00 mmol) were suspended in 50 mL of benzene and heated at reflux temperature for 16 hours. The reaction mixture was cooled and purified by column chromatography to elute 6.34 g of a crude mixture, which contained di-brominated product, from silica gel with a gradient of 0-20% ethyl acetate in hexanes.

6.10 g of the crude mixture (ca. 14.1 mmol of di-bromo intermediate) was dissolved in 35 mL of dry benzene. N-(2,4-dimethoxy-benzyl)glycine ethyl ester (4.0 g, 14.2 mmol) and potassium carbonate (2.14 g, 15.5 mmol) were added and the reaction mixture was stirred at room temperature for 18 hours. The reaction mixture was diluted with ethyl acetate and washed with water and brine. The organic fraction was dried over anhydrous sodium sulfate before being dissolved in 200 mL of 2:1 ethyl ether-hexanes. Approximately 3.6 mL of 4 N HCl in dioxane was added to precipitate a white solid/gum. The solution was decanted and the solid was washed three times with cold ether. These combined washes were set aside then back-extracted with 1 N HCl. The aqueous solution was basified with solid sodium bicarbonate, and extracted with ether. The ether solution was then washed with brine and combined with the ethereal solution below.

The solid, crude HCl-salt was partitioned between ethyl ether and sodium bicarbonate solution and washed with brine. The combined organic fractions were dried over sodium sulfate and concentrated to 7.26 g of a tan oil: MS: (+) m/z 500.2, 502.2 (M+1, $^{79}$Br/$^{81}$Br)

c) 2-Bromo-5-(2,4-dimethoxy-benzyl)-7-oxo-4,5,6,7-tetrahydro-thieno[3,2-c]pyridine-6-carboxylic acid ethyl ester 5-Bromo-3-{[(2,4-dimethoxy-benzyl)-ethoxycarbonylmethyl-amino]-methyl}-thiophene-2-carboxylic acid ethyl ester (example 21.b, 7.0 g, 14.1 mmol) was dissolved in 140 mL of anhydrous THF and cooled to −15° C. in a brine dry ice bath. A solution of 30 mL of 1.0 M potassium tert-butoxide in THF was added slowly to cold solution, and the reaction mixture was stirred at −15° C. for 30 min. and then at room temperature for 2 hours. The reaction was quenched with 29 mL of 1N HCl. and 400 mL ammonium chloride, and extracted twice with 300 mL ethyl acetate. The organic fractions were washed with brine, dried over anhydrous sodium sulfate and concentrated to 5.67 g of a tan viscous oil: MS: (+) m/z 453.6, 455.5 (M+1, $^{79}$Br/$^{81}$Br)

d) 2-Bromo-7-hydroxy-thieno[3,2-c]pyridine-6-carboxylic acid ethyl ester

2-Bromo-5-(2,4-dimethoxy-benzyl)-7-oxo-4,5,6,7-tetrahydro-thieno[3,2-c]pyridine-6-carboxylic acid ethyl ester (example 21.c, 5.66 g, 12.5 mmol) was dissolved in 85 mL of anhydrous dichloromethane. To the solution was added 1.37 mL of thionyl chloride, and the reaction mixture was stirred for 5 hours. The solution was filtered on a fine glass frit filter to collect a white solid precipitate. The solid was washed e) 7-Hydroxy-2-styryl-thieno[3,2-c]pyridine-6-carboxylic acid ethyl ester

Under a nitrogen atmosphere ester 2-Bromo-7-hydroxy-thieno[3,2-c]pyridine-6-carboxylic acid ethyl ester (250 mg, 0.83 mmol, example 21.d), styreneboronic acid (185 mg, 1.25 mmol), cesium carbonate (675 mg, 2.08 mmol), and tetrakis(triphenylphosphine)palladium(0) (92 mg, 0.08 mmol) were suspended in 4 mL of anhydrous 1,4 dioxane. The reaction mixture was heated at 120° C. for 30 minutes in a CEM microwave reactor, cooled to room temperature, and diluted with ethyl acetate. The organic mixture was successively washed with water, saturated sodium bicarbonate, and brine solutions. The organic fractions were dried over anhydrous sodium sulfate and concentrated to a crude solid residue, which was then purified by column chromatography, eluting the desired product from silica gel with a gradient of 20-60% ethyl acetate in hexanes: 224 mg of an off-white solid. MS: (+) m/z 326.0 (M+1)

f) [(7-Hydroxy-2-styryl-thieno[3,2-c]pyridine-6-carbonyl)-amino]-acetic acid The title compound was prepared from 7-hydroxy-2-styryl-thieno[3,2-c]pyridine-6-carboxylic acid ethyl ester, example 21.e, under conditions analogous to experimental example 17.d; MS: (+) m/z 354.9 (M+1).

Example 22

[(7-Hydroxy-2-phenoxy-thieno[3,2-c]pyridine-6-carbonyl)-amino]-acetic acid a) 3-Methyl-5-phenoxy-thiophene-2-carbaldehyde

A solution of 5-bromo-3-methyl-thiophene-2-carbaldehyde (example 1.a, 30.8 g, 150 mmol), phenol (28.2 g, 300 mmol), cesium carbonate (97 g, 300 mmol), copper(I) trifluoromethanesulfonate benzene complex (90%, 7.5 g, 15 mmol), and ethyl acetate (750 µL, 7.5 mmol) in 150 mL of anhydrous toluene was heated at reflux temperature for 48 hours. The resultant mixture was diluted with dichloromethane and 2 N NaOH(aq) and filtered through a small pad of celite, the solid was washed with additional dichloromethane and NaOH solution. The biphasic mixture was separated and the organic fraction was successively washed with 2 N NaOH and brine. The organic fraction was dried over anhydrous magnesium sulfate and concentrated to a residue. The crude product was purified by column chromatography, eluting the desired product from silica gel with a gradient of 5-30% ethyl acetate in hexanes to provide 6.4 g of product; MS: (+) m/z 219.4 (M+1)

b) 3-Methyl-5-phenoxy-thiophene-2-carboxylic acid

3-Methyl-5-phenoxy-thiophene-2-carbaldehyde, (example 22.a, 5.68 g, 25.9 mmol) was added to 26 mL of ethanol. To the mixture were added 21 mL of 5 N NaOH(aq) and silver nitrate (8.81 g, 52 mmol), and the resultant mixture was stirred for 19 hours at room temperature. The mixture was filtered through a pad of celite, washing the solid with ca. 50-100 mL portions of 1 N NaOH solution three times. The basic solution was washed with ethyl ether, then acidified with concentrated $H_2SO_4$, and extracted twice with ethyl acetate. The organic fractions were dried over anhydrous sodium sulfate and concentrated under high vacuum to 5.7 g of a yellow solid: MS: (−) m/z 232.9 (M−1)

c) 3-Methyl-5-phenoxy-thiophene-2-carboxylic acid ethyl ester

The title compound was prepared from 3-methyl-5-phenoxy-thiophene-2-carboxylic acid, example 22.b, analogously to experimental example 21.a. The product was isolated by column chromatography, eluting the desired product from silica gel with a gradient of 0-30% ethyl acetate in hexanes: MS: (+) m/z 262.9 (M+1)

d) 3-{[(2,4-Dimethoxy-benzyl)-ethoxycarbonylmethyl-amino]-methyl}-5-phenoxy-thiophene-2-carboxylic acid ethyl ester A solution of 3-methyl-5-phenoxy-thiophene-2-carboxylic acid ethyl ester (example 22.a, 693 mg, 2.64 mmol), N-bromosuccinimide (494 mg, 2.77 mmol), and benzoyl peroxide (50 mg, 0.2 mmol) in carbon tetrachloride was heated at reflux temperature for 20 h. The reaction mixture was cooled and run through a short column of silica gel, eluting with dichloromethane, to isolate a mixture of crude brominated intermediate.

The crude mixture was concentrated to a residue and dissolved in 4 mL of anhydrous DMF. To the solution was added N-(2,4-dimethoxy-benzyl)glycine ethyl ester (281 mg, 1 mmol) and potassium carbonate (138 mg, 1 mmol), and the reaction mixture was stirred for 19 hours at room temperature. The reaction mixture was diluted with ethyl acetate and washed successively with water, saturated bicarbonate solution, and brine. The organic solution was dried over anhydrous sodium sulfate and concentrated to a residue under high-vacuum. The desired product was isolated by column chromatography, eluting from silica gel with a gradient of 5-50% ethyl acetate in hexanes to give 357 mg of a viscous yellow oil.

$^1$H NMR (CDCl$_3$, 200 MHz): δ=7.35-7.1 (m, 6H), 6.82 (s, 1H), 6.42-6.38 (m, 2H), 4.3-4.05 (m, 6H), 3.78 (s, 3H), 3.75 (s, 2H), 3.70 (s, 3H), 3.29 (s, 2H), 1.31 (t, 3H, J=7.0 Hz), 1.24 (t, 3H, J=7.4 Hz)

e) 5-(2,4-Dimethoxy-benzyl)-7-oxo-2-phenoxy-4,5,6,7-tetrahydro-thieno[3,2-c]pyridine-6-carboxylic acid ethyl ester The title compound was prepared from 3-{[(2,4-dimethoxy-benzyl)-ethoxycarbonylmethyl-amino]-methyl}-5-phenoxy-thiophene-2-carboxylic acid ethyl ester, example 22.b, under experimental conditions analogous to example 21.c; MS: (−) m/z 466.1 (M−1)

f) 7-Hydroxy-2-phenoxy-thieno[3,2-c]pyridine-6-carboxylic acid ethyl ester

The title compound was prepared from 5-(2,4-dimethoxy-benzyl)-7-oxo-2-phenoxy-4,5,6,7-tetrahydro-thieno[3,2-c]pyridine-6-carboxylic acid ethyl ester, example 22.c, under experimental conditions analogous to example 21.d; MS: (+) m/z 344.9 (M+1)

g) [(7-Hydroxy-2-phenoxy-thieno[3,2-c]pyridine-6-carbonyl)-amino]-acetic acid The title compound was prepared from 7-hydroxy-2-phenoxy-thieno[3,2-c]pyridine-6-carboxylic acid ethyl ester, example 22.d, under conditions analogous to experimental example 17.d; MS: (+) m/z 344.9 (M+1)

Example 23

[(7-Hydroxy-2-phenethyl-thieno[3,2-c]pyridine-6-carbonyl)-amino]-acetic acid a) 7-Hydroxy-2-phenethyl-thieno[3,2-c]pyridine-6-carboxylic acid ethyl ester A mixture of 7-hydroxy-2-styryl-thieno[3,2-c]pyridine-6-carboxylic acid ethyl ester (example 21.g, 0.44 mmol) and 10% palladium on carbon (100 mg) in 20 mL of 1:1 ethyl acetate: ethyl alcohol was placed under a hydrogen atmosphere at 19 PSI on a parr shaker. At 7 hours an additional 60 mg of 10% Pd/C was added, after 24 hours an additional 75 mg of 10% Pd/C was added, and the reaction was stopped at 29 hours. The mixture was filtered through a celite pad and purified by flash chromatography, eluting the desired product from silica gel with a gradient of 20-80% ethyl acetate in hexanes to give 77 mg of desired product: MS: (+) m/z 327.9 (M+1)

b) [(7-Hydroxy-2-phenethyl-thieno[3,2-c]pyridine-6-carbonyl)-amino]-acetic acid

The title compound was prepared from 7-hydroxy-2-phenethyl-thieno[3,2-c]pyridine-6-carboxylic acid ethyl ester, example 23.a, under conditions analogous to experimental example 17.d; MS: (+) m/z 357.0 (M+1)

Example 24

{[7-Hydroxy-2-(3-trifluoromethyl-phenyl)-thieno[3,2-c]pyridine-6-carbonyl]-amino}-acetic acid a) 7-Hydroxy-2-(3-trifluoromethyl-phenyl)-thieno[3,2-c]pyridine-6-carboxylic acid ethyl ester The title compound was prepared from 3-(trifuoromethyl) phenyl boronic acid and 2-bromo-7-hydroxy-thieno[3,2-c]pyridine-6-carboxylic acid ethyl ester, example 21.d, under conditions analogous to experimental example 21.e; MS: (+) m/z 368.0 (M+1)

b) {[7-Hydroxy-2-(3-trifluoromethyl-phenyl)-thieno[3,2-c]pyridine-6-carbonyl]-amino}-acetic acid The title compound was prepared from 7-hydroxy-2-(3-trifluoromethyl-phenyl)-thieno[3,2-c]pyridine-6-carboxylic acid ethyl ester, example 24.b, under conditions analogous to experimental example 17.d; MS: (+) m/z 396.9 (M+1)

Example 25

{[4-Bromo-7-hydroxy-2-(3-trifluoromethyl-phenyl)-thieno[3,2-c]pyridine-6-carbonyl]-amino}-acetic acid a) 4-Bromo-7-hydroxy-2-(3-trifluoromethyl-phenyl)-thieno[3,2-c]pyridine-6-carboxylic acid ethyl ester A suspension of 7-hydroxy-2-(3-trifluoromethyl-phenyl)-thieno[3,2-c]pyridine-6-carboxylic acid ethyl ester (example 24.b, 120 mg, 0.32 mmol), N-bromosuccinimide (60 mg, 0.34 mmol), and benzoyl peroxide (7.3 mg, 0.03 mmol) in 0.8 mL of carbon tetrachloride was heated at reflux temperature for 5 hours. The reaction mixture was cooled and chromatographed on silica gel, eluting the desired product with 30% ethyl acetate in hexanes to provide 126 mg of a white solid: MS: (+) m/z 445.9, 447.9 (M+1, $^{79}$Br/$^{81}$Br)

b) {[4-Bromo-7-hydroxy-2-(3-trifluoromethyl-phenyl)-thieno[3,2-c]pyridine-6-carbonyl]-amino}-acetic acid The title compound was prepared from 4-bromo-7-hydroxy-2-(3-trifluoromethyl-phenyl)-thieno[3,2-c]pyridine-6-carboxylic acid ethyl ester, example 25.a, under conditions analogous to experimental example 17.d; MS: (−) m/z 472.9, 475.0 (M−1, $^{79}$Br/$^{81}$Br)

Example 26

{[4-Cyano-7-hydroxy-2-(3-trifluoromethyl-phenyl)-thieno[3,2-c]pyridine-6-carbonyl]-amino}-acetic acid a) 4-Cyano-7-hydroxy-2-(3-trifluoromethyl-phenyl)-thieno[3,2-c]pyridine-6-carboxylic acid ethyl ester A mixture of 4-bromo-7-hydroxy-2-(3-trifluoromethyl-phenyl)-thieno[3,2-c]pyridine-6-carboxylic acid ethyl ester (example 25.a, 108 mg, 0.24 mmol) and copper(I) cyanide (45 mg, 0.5 mmol) suspended in 1 mL DMF was heated at 135° C. for 15 minutes in a CEM microwave reactor. The resultant mixture was partitioned between ethyl acetate and water, and the organic fraction was washed with brine, dried over anhydrous sodium sulfate, and concentrated to a crude residue. The desired product was purified by column chromatography eluting from silica gel with a gradient of 10-60% ethyl acetate in hexanes to give 48 mg of a white solid; MS: (+) m/z 392.9 (M+1)

b) {[4-Cyano-7-hydroxy-2-(3-trifluoromethyl-phenyl)-thieno[3,2-c]pyridine-6-carbonyl]-amino}-acetic acid The title compound was prepared from 4-cyano-7-hydroxy-2-(3-trifluoromethyl-phenyl)-thieno[3,2-c]pyridine-6-carboxylic acid ethyl ester, example 26.a, under conditions analogous to experimental example 17.d; MS: (−) m/z 420.0 (M−1)

Example 27

[(2-Cyano-7-hydroxy-thieno[3,2-c]pyridine-6-carbonyl)-amino]-acetic acid a) 2-Cyano-7-hydroxy-thieno[3,2-c]pyridine-6-carboxylic acid ethyl ester A mixture of 2-bromo-7-hydroxy-thieno[3,2-c]pyridine-6-carboxylic acid ethyl ester (example 21.d, 150 mg, 0.5 mmol) and copper(I) cyanide (90 mg, 1.0 mmol) suspended in 2 mL DMF was heated at 140° C. for 30 minutes in a CEM microwave reactor. The resultant mixture was partitioned between ethyl acetate and water, and the organic fraction was washed with brine, dried over anhydrous sodium sulfate, and concentrated to a crude residue. The desired product was purified by column chromatography eluting from silica gel with a gradient of 20-70% ethyl acetate in hexanes to give 24 mg of a white solid; MS: (+) m/z 248.9 (M+1)

b) [(2-Cyano-7-hydroxy-thieno[3,2-c]pyridine-6-carbonyl)-amino]-acetic acid

The title compound was prepared from 2-cyano-7-hydroxy-thieno[3,2-c]pyridine-6-carboxylic acid ethyl ester, example 27.a, under conditions analogous to experimental example 17.d. The crude precipitated product was further purified by dissolution in ethyl acetate and washing with water. The organic solution was dried over anhydrous sodium sulfate and concentrated under high vacuum to give the desired product; MS: (−) m/z 276.0 (M−1)

Example 28

{[7-Hydroxy-2-(4-trifluoromethyl-phenyl)-thieno[3,2-c]pyridine-6-carbonyl]-amino}-acetic acid a) 7-Hydroxy-2-(4-trifluoromethyl-phenyl)-thieno[3,2-c]pyridine-6-carboxylic acid ethyl ester The title compound was prepared from 4-(trifuoromethyl)phenyl boronic acid and 2-bromo-7-hydroxy-thieno[3,2-c]pyridine-6-carboxylic acid ethyl ester, example 21.d, under conditions analogous to experimental example 21.e; MS: (+) m/z 367.9 (M+1)

b) {[7-Hydroxy-2-(4-trifluoromethyl-phenyl)-thieno[3,2-c]pyridine-6-carbonyl]-amino}-acetic acid The title compound was prepared from 7-hydroxy-2-(4-trifluoromethyl-phenyl)-thieno[3,2-c]pyridine-6-carboxylic acid ethyl ester, example 28.a, under conditions analogous to experimental example 17.d; MS: (−) m/z 395.0 (M−1)

Example 29

{[7-Hydroxy-2-(2-trifluoromethyl-phenyl)-thieno[3,2-c]pyridine-6-carbonyl]-amino}-acetic acid a) 7-Hydroxy-2-(2-trifluoromethyl-phenyl)-thieno[3,2-c]pyridine-6-carboxylic acid ethyl ester The title compound was prepared from 2-(trifuoromethyl)phenyl boronic acid and 2-bromo-7-hydroxy-thieno[3,2-c]pyridine-6-carboxylic acid ethyl ester, example 21.d, under conditions analogous to experimental example 21.e; MS: (+) m/z 367.9 (M+1)

b) {[7-Hydroxy-2-(2-trifluoromethyl-phenyl)-thieno[3,2-c]pyridine-6-carbonyl]-amino}-acetic acid The title compound was prepared from 7-hydroxy-2-(2-trifluoromethyl-phenyl)-thieno[3,2-c]pyridine-6-carboxylic acid ethyl ester, example 29.a, under conditions analogous to experimental example 17.d; MS: (−) m/z 395.0 (M−1)

Example 30

{[4-Bromo-3-(4-fluoro-phenyl)-7-hydro-thieno[3,2-c]pyridine-6-carbonyl]-amino}-acetic acid a) 4-Bromo-thiophene-2,3-dicarboxylic acid A suspension of 4-bromo-3-methyl-thiophene-2-carboxylic acid (7.37 g, 33.3 mmol, purchased from Oakwood Products), in the aqueous sodium hydroxide solution (3.75 N, 154.8 mL, 0.58 mol) was heated to 80° C. Potassium permanganate (21.1 g, 0.133 mmol) was added in 4.21 g portions to the warm solution over 2 hours. The resultant suspension was heated to reflux temperature for 3 hours and then cooled to room temperature. The solid was filtered off and washed twice with 1 N NaOH and twice with water. The aqueous solution was acidified to pH <3 with concentrated hydrochloric acid, washed twice with methylene chloride, and concentrated to a solid residue. The crude product was recrystallized from water to produce 4.46 g of a white solid. MS: (−) m/z 248.8, 250.9 (M−1, $^{79}$Br/$^{81}$Br).

b) 4-Bromo-thiophene-2,3-dicarboxylic acid dimethyl ester

4-Bromo-thiophene-2,3-dicarboxylic acid (0.5 g, 1.99 mmol), example 30-a, was suspended in thionyl chloride (10 mL) and heated to reflux for 1.5 h, in which time the solid completely dissolved. The reaction mixture was concentrated under hi-vacuum and dried to a solid residue. The solid was suspended in anhydrous methanol (15 mL), and the reaction mixture was refluxed overnight. The reaction mixture was diluted with ethyl acetate and washed successively with water, saturated sodium bicarbonate solution and brine. The organic solution was dried over anhydrous sodium sulfate, filtered and concentrated. The crude product was purified by flash chromatography eluting from silica gel with a gradient of 0-40% ethyl acetate in hexanes to produce 0.17 g of a white solid. MS: (+) m/z 278.8, 280.8. (M+1, $^{79}$Br/$^{81}$Br).

c) 4-Bromo-thiophene-2,3-dicarboxylic acid 3-methyl ester and 4-bromo-thiophene-2,3-dicarboxylic acid 2-methyl ester The aqueous sodium hydroxide (2 N, 3.14 mL, 6.28 mmol) was added to a solution of 4-bromo-thiophene-2,3-dicarboxylic acid dimethyl ester (1.67 g, 5.98 mmol), example 30-b, in methanol (12.6 mL) at 0° C. The reaction mixture was then stirred at ambient temperature for 2 h. After the solvent was evaporated, water (15 mL) was added. The aqueous solution was washed with ethyl acetate, acidified to pH 1~2, and extracted with ethyl acetate. The combined organic layers were dried, filtered, and concentrated to produce 1.41 g of a mixture of the title compounds. MS: (−) m/z 262.7, 264.7 (M−1, $^{79}$Br/$^{81}$Br).

d) 4-Bromo-2-(ethoxycarbonylmethyl-carbamoyl)-thiophene-3-carboxylic acid methyl ester and 4-bromo-3-(ethoxycarbonylmethyl-carbamoyl)-thiophene-2-carboxylic acid methyl ester N,N-Dimethylformamide (13 µL) was added to a solution of oxalyl chloride (0.696 mL, 7.97 mmol), 4-bromo-thiophene-2,3-dicarboxylic acid 3-methyl ester and 4-bromo-thiophene-2,3-dicarboxylic acid 2-methyl ester (1.41 g, 5.32 mmol), example 30-c, in tetrahydrofuran (6.4 mL) at 0° C. The reaction mixture was stirred at 0° C. for 15 min, and then at ambient temperature for 1 h. After the reaction mixture was concentrated and dried under hi-vacuum, the residue was dissolved in 1,4-dioxane (2.5 mL) and cooled to 0° C. with an external ice bath. Triethylamine (2.22 mL, 16.0 mmol) and glycine ethyl ester hydrochloride salt (1.11 g, 7.97 mmol) were added slowly to the cold solution. The reaction mixture was warmed to room temperature and stirred for 2.5 h. The reaction mixture was diluted with ethyl acetate and washed successively with 0.5 N HCl, water, saturated sodium bicarbonate solution and brine. The organic solution was dried over anhydrous sodium sulfate and concentrated. The crude product was purified by flash chromatography eluting from silica gel with a gradient of 0-60% ethyl acetate in hexanes to produce 1.0 g of 4-bromo-2-(ethoxycarbonylmethyl-carbamoyl)-thiophene-3-carboxylic acid methyl ester and 0.1 g of 4-bromo-3-(ethoxycarbonylmethyl-carbamoyl)thiophene-2-carboxylic acid methyl ester. MS for 4-bromo-2-(ethoxycarbonylmethyl-carbamoyl)-thiophene-3-carboxylic acid methyl ester: (+) m/z 349.9, 351.9 (M+1, $^{79}Br/^{81}Br$). MS for 4-bromo-3-(ethoxycarbonylmethyl-carbamoyl)-thiophene-2-carboxylic acid methyl ester: (+) m/z 349.9, 351.9 (M+1, $^{79}Br/^{81}Br$).

e) 2-(Ethoxycarbonylmethyl-carbamoyl)-4-(4-fluoro-phenyl)-thiophenyl-3-carboxylic acid methyl ester Under a nitrogen atmosphere, 4-bromo-2-(ethoxycarbonylmethyl-carbamoyl)-thiophene-3-carboxylic acid methyl ester, example 30-d (1.0 g, 2.86 mmol), 4-fluoro-phenyl boronic acid (0.479 mg, 3.43 mmol), potassium carbonate (1.42 g, 10.3 mmol), and tetrakis(triphenylphosphine)palladium(0) (495 mg, 0.43 mmol) were suspended in 45 mL of 1,4-dioxane. The reaction mixture was heated at reflux temperature overnight, cooled to room temperature and diluted with ethyl acetate. The organic mixture was successively washed with saturated sodium bicarbonate and brine solutions. The organic fractions were dried over anhydrous sodium sulfate and concentrated to an oil residue, which was then purified by column chromatography, eluting the title compound from silica gel with a gradient of (0-50%) ethyl acetate in hexanes to yield 0.54 g of a brown oil. MS: (+) m/z 365.9 (M+1).

f) 3-(4-Fluoro-phenyl)-4,7-dihydroxy-thieno[3,2-c]pyridine-6-carboxylic acid butyl ester and 3-(4-fluoro-phenyl)-4,7-dihydroxy-thieno[2,3-c]pyridine-5-carboxylic acid butyl ester 2-(Ethoxycarbonylmethyl-carbamoyl)-4-(4-fluoro-phenyl)-thiophenyl-3-carboxylic acid methyl ester (0.54 g, 1.48 mmol), example 30-e, was added to 6.8 mL of 0.44 N sodium n-butoxide in n-butanol. The reaction mixture was heated at 100° C. for 2 hours, cooled, and 0.62 mL of 6 N HCl was added. The reaction mixture was concentrated to a solid residue. The crude product was purified by column chromatography eluting from silica gel with a gradient of 0-50% ethyl acetate in dichloromethane to produce 78 mg of 3-(4-fluoro-phenyl)-4,7-dihydroxy-thieno[3,2-c]pyridine-6-carboxylic acid butyl ester and 252 mg of 3-(4-fluoro-phenyl)-4,7-dihydroxy-thieno[2,3-c]pyridine-5-carboxylic acid butyl ester. MS for 3-(4-fluoro-phenyl)-4,7-dihydroxy-thieno[3,2-c]pyridine-6-carboxylic acid butyl ester: (+) m/z 362.0 (M+1). MS for 3-(4-fluoro-phenyl)-4,7-dihydroxy-thieno[2,3-c]pyridine-5-carboxylic acid butyl ester: (+) m/z 361.9 (M+1).

g) 4-Bromo-3-(4-fluoro-phenyl)-7-hydroxy-thieno[3,2-c]pyridine-6-carboxylic acid butyl ester 3-(4-Fluoro-phenyl)-4,7-dihydroxy-thieno[3,2-c]pyridine-6-carboxylic acid butyl ester (77.9 mg, 0.216 mmol), example 30-f, was suspended in 1.1 mL of anhydrous toluene. Phosphorous oxybromide (0.155 g, 0.539 mmol) was added, and the reaction mixture was heated at 120° C. for 20 min. using a CEM microwave reactor (CEM, Matthews, N.C.). The reaction mixture was diluted with ethyl acetate, and saturated sodium bicarbonate solution was then added. The biphasic mixture was stirred for 15 min. and separated to isolate the organic fraction. The organic fraction was washed with brine, dried over anhydrous sodium sulfate, and concentrated. The crude product was purified by column chromatography eluting from silica gel with dichloromethane to produce 51.2 mg of the title compound. MS: (−) m/z 422.1, 424.1 (M−1, $^{79}Br/^{81}Br$).

h) {[4-Bromo-3-(4-fluoro-phenyl)-7-hydro-thieno[3,2-c]pyridine-6-carbonyl]-amino}-acetic acid 4-Bromo-3-(4-fluoro-phenyl)-7-hydroxy-thieno[3,2-c]pyridine-6-carboxylic acid butyl ester (49.2 mg, 0.116 mmol), example 30-g, and glycine (183 mg, 2.44 mmol) were suspended in 4.64 mL of 0.5 N sodium methoxide in methanol. The reaction mixture was heated at reflux temperature overnight, cooled, and concentrated. The residue was dissolved in water (15 mL), and the solution was acidified to pH 1~2 with 2 N HCl, extracted with ethyl acetate. The combined organic layers were dried, filtered and concentrated to produce 49.3 mg of a yellow solid. MS: (−) m/z 423.0, 425.0 (M−1, $^{79}Br/^{81}Br$)

Example 31

{[3-(4-Fluoro-phenyl)-7-hydro-thieno[3,2-c]pyridine-6-carbonyl]-amino}-acetic acid a) 4-Bromo-3-methyl-thiophene-2-carboxylic acid methyl ester The (trimethylsilyl)diazomethane solution in ether (2.0 M, 41.2 mL, 82.3 mmol) was added dropwise to a solution of 4-bromo-3-methyl-thiophene-2-carboxylic acid (13.0 g, 58.8 mmol, purchased from Oakwood Products) in methanol (50 mL) and tetrahydrofuran (50 mL) at ambient temperature. After the reaction mixture was stirred at ambient temperature for 30 min, acetic acid was added to decompose the excess (trimethylsilyl)diazomethane until the yellow color disappeared. Most of the solvent was evaporated and ethyl acetate was added. The organic solution was washed with saturated sodium bicarbonate solution and brine, dried over anhydrous sodium sulfate and concentrated. The crude product was purified by flash chromatography eluting from silica gel with a gradient of 0-50% ethyl acetate in hexanes to produce 12.8 g of a white solid. $^1H$ NMR (CDCl$_3$, 200 MHz): δ=7.40 (s, 1H), 3.87 (s, 3H), and 2.54 (s, 3H).

b) 4-Bromo-3-bromomethyl-thiophene-2-carboxylic acid methyl ester

4-Bromo-3-methyl-thiophene-2-carboxylic acid methyl ester (3.0 g, 12.8 mmol), example 31-a, N-bromosuccinimide (2.33 g, 13.1 mmol), and benzoyl peroxide (310 mg, 1.28 mmol) were suspended in 32 mL of benzene and heated at reflux temperature for 16 hours. The reaction mixture was cooled and diluted with ethyl acetate. The reaction mixture was washed successively with saturated bicarbonate solution, brine, saturated ammonium chloride solution, and brine. The organic solvent was dried, filtered, and concentrated. The crude product was purified by flash chromatography eluting from silica gel with a gradient of 0-40% ethyl acetate in hexanes to produce 2.28 g of a yellow solid. $^1H$ NMR (CDCl$_3$, 200 MHz): δ=7.48 (s, 1H), 4.91 (s, 2H), and 3.94 (s, 3H).

c) 4-Bromo-3-{[(2,4-dimethoxy-benzyl)-methoxy-carbonylmethyl-amino]-methyl}-thiophene-2-carboxylic acid methyl ester 4-Bromo-3-bromomethyl-thiophene-2-carboxylic acid methyl ester (2.28 g, 7.31 mmol), example 31-b, was dissolved in 18 mL of dry N,N-dimethylformamide. N-(2,4-dimethoxy-benzyl)glycine ethyl ester (1.75 g, 7.31 mmol) and potassium carbonate (1.11 g, 8.04 mmol) were added and the reaction mixture was stirred at room temperature for 18 hours. The reaction mixture was diluted with ethyl acetate and washed with water and brine. The organic fraction was dried over anhydrous sodium sulfate, and concentrated. The crude product was purified by flash chromatography eluting from silica gel with a gradient of 0-60% ethyl acetate in hexanes to produce 3.18 g of a tan oil. MS: (+) m/z 494.1, 496.1 (M+Na$^+$, $^{79}$Br/$^{81}$Br).

d) 3-Bromo-5-(2,4-dimethoxy-benzyl)-7-oxo-4,5,6,7-tetrahydro-thieno[3,2-c]pyridine-6-carboxylic acid methyl ester 4-Bromo-3-{[(2,4-dimethoxy-benzyl)-methoxycarbonyl-methyl-amino]-methyl}-thiophene-2-carboxylic acid methyl ester (13.3 g, 28.2 mmol), example 31-c, was dissolved in 277 mL of anhydrous THF and cooled to −15° C. in a brine dry ice bath. A solution of 62.0 mL of 1.0 M potassium tert-butoxide in THF was added slowly to cold solution, and the reaction mixture was stirred at −15° C. for 30 min. and then at room temperature for 2 hours. The reaction was quenched with 62.0 mL of 1N HCl and 500 mL ammonium chloride, and extracted twice with 600 mL of ethyl acetate. The organic fractions were washed with brine, dried over anhydrous sodium sulfate and concentrated. The crude product was purified by flash chromatography eluting from silica gel with a gradient of 0-50% ethyl acetate in hexanes to produce 12.4 g of a yellow froth. MS: (+) m/z 461.9, 463.9 (M+Na$^+$, $^{79}$Br/$^{81}$Br).

e) 5-(2,4-dimethoxy-benzyl)-3-(4-fluoro-phenyl)-7-oxo-4,5,6,7-tetrahydro-thieno[3,2-c]pyridine-6-carboxylic acid methyl ester The title compound was prepared from 3-bromo-5-(2,4-dimethoxy-benzyl)-7-oxo-4,5,6,7-tetrahydro-thieno[3,2-c]pyridine-6-carboxylic acid methyl ester, example 31-d, under conditions analogous to experimental example 30-e. MS: (+) m/z 478.1 (M+Na$^+$).

f) 3-(4-Fluoro-phenyl)-7-hydroxy-thieno[3,2-c]pyridine-6-carboxylic acid methyl ester 5-(2,4-dimethoxy-benzyl)-3-(4-fluoro-phenyl)-7-oxo-4,5,6,7-tetrahydro-thieno[3,2-c]pyridine-6-carboxylic acid methyl ester (0.39 g, 0.86 mmol), example 31-e, was dissolved in 6 mL of anhydrous dichloromethane. To the solution was added 93.7 μL of thionyl chloride, and the reaction mixture was stirred for 5 hours. The solution was filtered on a fine glass frit filter to collect a white solid precipitate. The solid was washed twice with cold dichloromethane and then partitioned between saturated sodium bicarbonate solution and ethyl acetate. The organic fraction was washed with brine, dried over anhydrous sodium sulfate, and concentrated to produce 0.16 g of a white solid. MS: (+) m/z 304.0 (M+1)

g) {[3-(4-fluoro-phenyl)-7-hydroxy-thieno[3,2-c]pyridine-6-carbonyl]-amino}-acetic acid The title compound was prepared from 3-(4-fluoro-phenyl)-7-hydroxy-thieno[3,2-c]pyridine-6-carboxylic acid methyl ester, example 31-f, under conditions analogous to experimental example 30-h. MS: (−) m/z 345.0 (M−1).

Example 32

{[3-(4-Fluoro-phenyl)-7-hydroxy-4-methyl-thieno[3,2-c]pyridine-6-carbonyl]-amino}-acetic acid a) 4-Bromo-3-(4-fluoro-phenyl)-7-hydroxy-thieno[3,2-c]pyridine-6-carboxylic acid methyl ester A suspension of 3-(4-fluoro-phenyl)-7-hydroxy-thieno[3,2-c]pyridine-6-carboxylic acid methyl ester (100 mg, 0.33 mmol), example 31-f, N-bromosuccinimide (61.6 mg, 0.346 mmol), and benzoyl peroxide (8.0 mg, 0.033 mmol) in 0.83 mL of carbon tetrachloride was heated at reflux temperature for 5 hours. The reaction mixture was washed successively with saturated sodium bicarbonate, brine, saturated ammonium chloride solution, and brine. The organic solution was dried, filtered, and concentrated. The crude product was purified by flash chromatography eluting from silica gel with a gradient of 0-50% ethyl acetate in methylene chloride to produce 77.9 mg of a light yellow solid. MS: (−) m/z 380.3, 382.1 (M−1, $^{79}$Br/$^{81}$Br).

b) 3-(4-Fluoro-phenyl)-7-hydroxy-4-methyl-thieno[3,2-c]pyridine-6-carboxylic acid methyl ester Under a nitrogen atmosphere, a mixture of 4-bromo-3-(4-fluoro-phenyl)-7-hydroxy-thieno[3,2-c]pyridine-6-carboxylic acid methyl ester (77.9 mg, 0.204 mmol), example 32-a, trimethylboroxane (57.0 μL, 0.408 mmol), potassium carbonate (169 mg, 1.22 mmol), and tetrakis(triphenylphosphine)-palladium(0) (35.3 mg, 0.031 mmol) were suspended in 3.5 mL of anhydrous 1,4-dioxane. The reaction mixture was heated at 100° C. for 16 hours, cooled to room temperature, and diluted with ethyl acetate. The organic mixture was successively washed with water, saturated sodium bicarbonate, and brine solutions. The organic fractions were dried over anhydrous sodium sulfate and concentrated. The crude product was purified by flash chromatography eluting from silica gel with a gradient of 0-50% ethyl acetate in hexanes to produce 36.8 mg of a white solid. MS: (+) m/z 318.0 (M+1).

c) {[3-(4-Fluoro-phenyl)-7-hydroxy-4-methyl-thieno[3,2-c]pyridine-6-carbonyl]-amino}-acetic acid The title compound was prepared from 3-(4-fluoro-phenyl)-7-hydroxy-4-methyl-thieno[3,2-c]pyridine-6-carboxylic acid methyl ester, example 32-b, under conditions analogous to experimental example 30-h. MS: (−) m/z 359.0 (M−1).

Example 33

{[4-Cyano-3-(4-fluoro-phenyl)-7-hydroxy-thieno[3,2-c]pyridine-6-carbonyl]-amino}-acetic acid a) 4-Cyano-3-(4-fluoro-phenyl)-7-hydroxy-thieno[3,2-c]pyridine-6-carboxylic acid methyl ester A mixture of 4-bromo-3-(4-fluoro-phenyl)-7-hydroxy-thieno[3,2-c]pyridine-6-carboxylic acid methyl ester (58.5 mg, 0.153 mmol), example 32-a, and copper(I) cyanide (27.4 mg, 0.306 mmol) suspended in 1.5 mL of DMF was heated at 150° C. for 30 minutes. The resultant mixture was partitioned between ethyl acetate and water, and the organic fraction was washed with brine, dried over anhydrous sodium sulfate, and concentrated. The crude product was purified by flash chromatography eluting from silica gel with a gradient of 0-20% methanol in methylene chloride to produce 15.1 mg of a white solid. MS: (+) m/z 329.0 (M+1).

b) {[4-Cyano-3-(4-fluoro-phenyl)-7-hydroxy-thieno [3,2-c]pyridine-6-carbonyl]-amino}-acetic acid The title compound was prepared from 4-cyano-3-(4-fluoro-phenyl)-7-hydroxy-thieno[3,2-c]pyridine-6-carboxylic acid methyl ester, example 33-a, under conditions analogous to experimental example 30-h. MS: (−) m/z 370.0 (M−1).

Example 34

{[2-(4-fluoro-phenyl)-7-hydroxy-thieno[3,2-c]pyridine-6-carbonyl]-amino}-acetic acid a) 2-(Ethoxycarbonylmethyl-carbamoyl)-5-(4-fluoro-phenyl)-thiophene-3-carboxylic acid methyl ester and 3-(ethoxycarbonylmethyl-carbamoyl)-5-(4-fluoro-phenyl)-thiophene-2-carboxylic acid methyl ester The title compound was prepared from 5-bromo-2-(ethoxycarbonylmethyl-carbamoyl)-thiophene-3-carboxylic acid methyl ester and 5-bromo-3-(ethoxycarbonylmethyl-carbamoyl)-thiophene-2-carboxylic acid methyl ester, example 11.c crude intermediate, under conditions analogous to experimental example 30-e. MS: (+) m/z 366.1 (M+1).

b) 2-(4-Fluoro-phenyl)-4,7-dihydroxy-thieno[3,2-c]pyridine-6-carboxylic acid butyl ester and 2-(4-fluoro-phenyl)-4,7-dihydroxy-thieno[2,3-c]pyridine-5-carboxylic acid butyl ester The title compound was prepared from 2-(ethoxycarbonylmethyl-carbamoyl)-5-(4-fluoro-phenyl)-thiophene-3-carboxylic acid methyl ester and 3-(ethoxycarbonylmethyl-carbamoyl)-5-(4-fluoro-phenyl)-thiophene-2-carboxylic acid methyl ester, example 34-a, under conditions analogous to experimental example 30-f. MS: (+) m/z 362.2 (M+1).

c) 4-Bromo-2-(4-fluoro-phenyl)-7-hydroxy-thieno[3, 2-c]pyridine-6-carboxylic acid butyl ester and 7-bromo-2-(4-fluoro-phenyl)-4-hydroxy-thieno[2,3-c]pyridine-5-carboxylic acid butyl ester The title compound was prepared from 2-(4-fluoro-phenyl)-4,7-dihydroxy-thieno[3,2-c]pyridine-6-carboxylic acid butyl ester and 2-(4-fluoro-phenyl)-4,7-dihydroxy-thieno[2,3-c]pyridine-5-carboxylic acid butyl ester, example 34-b, under conditions analogous to experimental example 30-g. MS: (+) m/z 424.0, 425.9 (M+1, $^{79}$Br/$^{81}$Br).

d) 2-(4-Fluoro-phenyl)-7-hydroxy-thieno[3,2-c]pyridine-6-carboxylic acid butyl ester and 2-(4-fluoro-phenyl)-4-hydroxy-thieno[2,3-c]pyridine-5-carboxylic acid butyl ester A mixture of palladium on carbon (10%, 20 mg), ammonium formate (74.4 mg, 1.18 mmol), 4-bromo-2-(4-fluoro-phenyl)-7-hydroxy-thieno[3,2-c]pyridine-6-carboxylic acid butyl ester and 7-bromo-2-(4-fluoro-phenyl)-4-hydroxy-thieno[2,3-c]pyridine-5-carboxylic acid butyl ester (50 mg, 0.118 mmol), example 34-c, in ethyl acetate (1.5 mL) was refluxed for 2.5 h. The catalyst was filtered off and the resulting solution was concentrated. The crude product was purified by flash chromatography eluting from silica gel with a gradient of 0-60% ethyl acetate in hexanes to produce 11.0 mg of 2-(4-fluoro-phenyl)-7-hydroxy-thieno[3,2-c]pyridine-6-carboxylic acid butyl ester and 10.0 mg of 2-(4-fluoro-phenyl)-4-hydroxy-thieno[2,3-c]pyridine-5-carboxylic acid butyl ester. MS for 2-(4-fluoro-phenyl)-7-hydroxy-thieno[3,2-c]pyridine-6-carboxylic acid butyl ester: (+) m/z 346.0 (M+1). MS for 2-(4-fluoro-phenyl)-4-hydroxy-thieno[2,3-c]pyridine-5-carboxylic acid butyl ester: (+) m/z 346.0 (M+1).

e) {[2-(4-fluoro-phenyl)-7-hydroxy-thieno[3,2-c]pyridine-6-carbonyl]-amino}-acetic acid The title compound was prepared from 2-(4-fluoro-phenyl)-7-hydroxy-thieno[3,2-c]pyridine-6-carboxylic acid butyl ester, example 34-d, under conditions analogous to experimental example 30-h. MS: (−) m/z 345.0 (M−1).

Example 35

{[2-(4-fluoro-phenyl)-7-hydroxy-4-methyl-thieno[3, 2-c]pyridine-6-carbonyl]-amino}-acetic acid a) 2-(4-Fluoro-phenyl)-7-hydroxy-4-methyl-thieno [3,2-c]pyridine-6-carboxylic acid butyl ester and 2-(4-fluoro-phenyl)-4-hydroxy-7-methyl-thieno[2,3-c]pyridine-5-carboxylic acid butyl ester The title compound was prepared from 4-bromo-2-(4-fluoro-phenyl)-7-hydroxy-thieno[3,2-c]pyridine-6-carboxylic acid butyl ester and 7-bromo-2-(4-fluoro-phenyl)-4-hydroxy-thieno[2,3-c]pyridine-5-carboxylic acid butyl ester, example 34-c, under conditions analogous to experimental example 32-b. MS for 2-(4-fluoro-phenyl)-7-hydroxy-4-methyl-thieno[3,2-c]pyridine-6-carboxylic acid butyl ester: (+) m/z 360.0.0 (M+1). MS for 2-(4-fluoro-phenyl)-4-hydroxy-7-methyl-thieno[2,3-c]pyridine-5-carboxylic acid butyl ester: (+) m/z 360.0.0 (M+1).

b) {[2-(4-fluoro-phenyl)-7-hydroxy-4-methyl-thieno [3,2-c]pyridine-6-carbonyl]-amino}-acetic acid The title compound was prepared from 2-(4-fluoro-phenyl)-7-hydroxy-4-methyl-thieno[3,2-c]pyridine-6-carboxylic acid butyl ester, example 35-a, under conditions analogous to experimental example 30-h. MS: (−) m/z 359.0 (M−1).

Example 36

{[2,3-Bis-(4-fluoro-phenyl)-7-hydroxy-thieno[3,2-c]pyridine-6-carbonyl]-amino}-acetic acid a) 3-Methyl-thiophene-2-carboxylic acid methyl ester The title compound was prepared from 3-methyl-thiophene-2-carboxylic acid (purchased from VWR), under conditions analogous to experimental example 31-a. MS: (+) m/z 156.9 (M+1).

b) 4,5-Dibromo-3-methyl-thiophene-2-carboxylic acid methyl ester

A mixture of bromine (8.59 mL, 0.168 mol) and 3-methyl-thiophene-2-carboxylic acid methyl ester (2.62 g, 16.8 mmol), example 36-a, was stirred at 0° C. for 1.5 h. Methylene chloride was added and the solution was washed with saturated sodium bicarbonate solution and brine. The organic layer was dried, filtered, and concentrated to produce 5.01 g of a off-white solid. $^1$H NMR (CDCl$_3$, 200 MHz): δ=3.85 (s, 3H) and 2.52 (s, 3H).

c) 4,5-Dibromo-3-bromomethyl-thiophene-2-carboxylic acid methyl ester

The title compound was prepared from 4,5-dibromo-3-methyl-thiophene-2-carboxylic acid methyl ester, example 36-b, under conditions analogous to experimental example 31-b. $^1$H NMR (CDCl$_3$, 200 MHz): δ=4.89 (s, 2H) and 3.91 (s, 3H).

d) 4,5-Dibromo-3-{[(2,4-dimethoxy-benzyl)-methoxycarbonylmethyl-amino]-methyl}-thiophene-2-carboxylic acid methyl ester The title compound was prepared from 4,5-dibromo-3-bromomethyl-thiophene-2-carboxylic acid methyl ester, example 36-c, under conditions analogous to experimental example 31-c. MS: (+) m/z 550.0 (M+1).

e) 2,3-Dibromo-5-(2,4-dimethoxy-benzyl)-7-oxo-4,5,6,7-tetrahydro-thieno[3,2-c]pyridine-6-carboxylic acid methyl ester The title compound was prepared from 4,5-dibromo-3-{[(2,4-dimethoxy-benzyl)-methoxycarbonylmethyl-amino]-methyl}-thiophene-2-carboxylic acid methyl ester, example 36-d, under conditions analogous to experimental example 31-d. MS: (+) m/z 517.6 (M+1).

f) 2,3-Dibromo-7-hydroxy-thieno[3,2-c]pyridine-6-carboxylic acid methyl ester

The title compound was prepared from 2,3-dibromo-5-(2,4-dimethoxy-benzyl)-7-oxo-4,5,6,7-tetrahydro-thieno[3,2-c]pyridine-6-carboxylic acid methyl ester, example 36-e, under conditions analogous to experimental example 31-f. MS: (+) m/z 365.8 (M+1).

g) 3-Bromo-2-(4-fluoro-phenyl)-7-hydroxy-thieno[3,2-c]pyridine-6-carboxylic acid methyl ester The title compound was prepared from 2,3-dibromo-7-hydroxy-thieno[3,2-c]pyridine-6-carboxylic acid methyl ester, example 36-f, under conditions analogous to experimental example 30-e. MS: (−) m/z 380.1, 382.1 (M−1, $^{79}$Br/$^{81}$Br).

h) 2,3-Bis-(4-fluoro-phenyl)-7-hydroxy-thieno[3,2-c]pyridine-6-carboxylic acid methyl ester 3-Bromo-2-(4-fluoro-phenyl)-7-hydroxy-thieno[3,2-c]pyridine-6-carboxylic acid methyl ester (0.34 g, 0.89 mmol), example 36-g, 4-fluoro-phenyl boronic acid (0.373 mg, 2.67 mmol), sodium methoxide (0.433 g, 8.01 mmol), and tetrakis(triphenylphosphine)palladium(0) (257 mg, 0.22 mmol) were suspended in 15 mL of 1,4-dioxane. The reaction mixture was heated at 120° C. for 30 min. using a CEM microwave reactor (CEM, Matthews, N.C.). The reaction mixture was diluted with ethyl acetate, and washed with saturated sodium bicarbonate and brine solutions. The organic fraction was dried over anhydrous sodium sulfate and concentrated. The crude product was purified by flash chromatography eluting from silica gel with a gradient of 0-60% ethyl acetate in hexanes to produce 0.179 g of a yellow solid. MS: (+) m/z 398.0 (M+1).

i) {[2,3-Bis-(4-fluoro-phenyl)-7-hydroxy-thieno[3,2-c]pyridine-6-carbonyl]-amino}-acetic acid The title compound was prepared from 2,3-bis-(4-fluoro-phenyl)-7-hydroxy-thieno[3,2-c]pyridine-6-carboxylic acid methyl ester, example 36-h, under conditions analogous to experimental example 30-h. MS: (−) m/z 439.1 (M−1).

Example 37

{[7-Bromo-3-(4-fluoro-phenyl)-4-hydroxy-thieno[2,3-c]pyridine-5-carbonyl]-amino}-acetic acid a) 7-Bromo-3-(4-fluoro-phenyl)-4-hydroxy-thieno[2,3-c]pyridine-5-carboxylic acid butyl ester The title compound was prepared from 3-(4-fluoro-phenyl)-4,7-dihydroxy-thieno[2,3-c]pyridine-5-carboxylic acid butyl ester, example 30-f, under conditions analogous to experimental example 30-g. MS: (−) m/z 422.1, 424.2 (M−1, $^{79}$Br/$^{81}$Br).

b) {[7-Bromo-3-(4-fluoro-phenyl)-4-hydroxy-thieno[2,3-c]pyridine-5-carbonyl]-amino}-acetic acid The title compound was prepared from 7-bromo-3-(4-fluoro-phenyl)-4-hydroxy-thieno[2,3-c]pyridine-5-carboxylic acid butyl ester, example 37-a, under conditions analogous to experimental example 30-h. MS: (−) m/z 423.0, 424.9 (M−1, $^{79}$Br/$^{81}$Br).

Example 38

{[3-(4-Fluoro-phenyl)-4-hydroxy-thieno[2,3-c]pyridine-5-carbonyl]-amino}-acetic acid a) 3-(4-Fluoro-phenyl)-4-hydroxy-thieno[2,3-c]pyridine-5-carboxylic acid butyl ester The title compound was prepared from 7-bromo-3-(4-fluoro-phenyl)-4-hydroxy-thieno[2,3-c]pyridine-5-carboxylic acid butyl ester, example 37-a, under conditions analogous to experimental example 34-d. MS: (+) m/z 346.0 (M+1).

b) {[3-(4-Fluoro-phenyl)-4-hydroxy-thieno[2,3-c]pyridine-5-carbonyl]-amino}-acetic acid The title compound was prepared from 3-(4-fluoro-phenyl)-4-hydroxy-thieno[2,3-c]pyridine-5-carboxylic acid butyl ester, example 38-a, under conditions analogous to experimental example 30-h. MS: (−) m/z 345.0 (M−1).

Example 39

{[2-(4-Fluoro-phenyl)-4-hydroxy-thieno[2,3-c]pyridine-5-carbonyl]-amino}-acetic acid The title compound was prepared from 2-(4-fluoro-phenyl)-4-hydroxy-thieno[2,3-c]pyridine-5-carboxylic acid butyl ester, example 34-d, under conditions analogous to experimental example 30-h. MS: (−) m/z 344.9 (M−1).

Example 40

{[2-(4-Fluoro-phenyl)-4-hydroxy-7-methyl-thieno[2,3-c]pyridine-5-carbonyl]-amino}-acetic acid The title compound was prepared from 2-(4-fluoro-phenyl)-4-hydroxy-7-methyl-thieno[2,3-c]pyridine-5-carboxylic acid butyl ester, example 35-a, under conditions analogous to experimental example 30-h. MS: (−) m/z 359.0 (M−1).

Example 41

[(7-Chloro-4-hydroxy-thieno[2,3-c]pyridine-5-carbonyl)-amino]-acetic acid a) Thiophene-2,3-dicarboxylic acid A solution of 3-Methyl-thiophene-2-carboxylic acid (0.5 mol; 71.09 g) in aqueous 15% NaOH (2300 ml) was heated to 75-80° C. before $KMnO_4$ (0.42 mol; 67.05 g) was added with stirring. After stirring at 75-80° C. for 30 min another portion of $KMnO_4$ (0.42 mol; 67.05 g) was added. This was repeated another three times. After adding the last portion of $KMnO_4$, stirring was continued at 75-80° C. for 30 min before the mixture was refluxed for 3 h with stirring. The hot mixture was submitted to vacuum filtration and the filtrate was acidified by addition on conc. aqueous HCl. The formed precipitate was separated, washed with water and dried in vacuo at 80° C. to give the title compound as a slightly yellowish solid (43.9 g). $^1$H NMR ($d_6$-DMSO, 200 MHz): δ=7.78 (d, 1H), 7.37 (d, 1H).

b) (4,6-Dioxo-3a,4,6,6a-tetrahydro-thieno[2,3-c]pyrrol-5-yl)-acetic acid methyl ester A mixture of thiophene-2,3-dicarboxylic acid (0.24 mol; 41.32 g) and acetic anhydride (240 ml) was refluxed with stirring for 2 h before it was concentrated in vacuo. The residue was dried in vacuo at 80° C. for 1 h before it was dissolved in anhydrous $CH_2Cl_2$ (480 ml). Then glycine methyl ester hydrochloride (0.36 mol; 45.66 g) was added and the mixture was cooled with an ice bath. Subsequently, triethylamine (0.72 mol, 101 ml) was added dropwise with stirring. Then, the ice-bath was removed and stirring was continued at ambient temperature for 18 h before the mixture was concentrated in vacuo. The residue was dissolved in $H_2O$ (1200 ml) and the solution was acidified by the addition of 6 N HCl. The resulting precipitate was separated, washed thoroughly with $H_2O$ and was dried in vacuo at 80° C. to give an off-white solid (52.4 g). 51.09 g of this solid were added to a solution of thionyl chloride (60 ml) in 1,4-dioxane (600 ml). The mixture was refluxed with stirring for 80 min before it was concentrated in vacuo. The residue was dissolved in EtOAc (600 ml) and the solution was washed thoroughly with conc. aqueous $NaHCO_3$ solution (100 ml) before it was dried over $MgSO_4$ and concentrated in vacuo to give the title compound as a tan solid (46.5 g). $^1$H NMR ($CDCl_3$, 200 MHz): δ=7.79 (d, 1H), 7.33 (d, 1H), 4.37 (s, 2H), 3.76 (s, 3H).

c) 4,7-Dihydroxy-thieno[2,3-c]pyridine-5-carboxylic acid butyl ester (A) and 4,7-dihydroxy-thieno[3,2-c]pyridine-6-carboxylic acid butyl ester (B)

Sodium (20.5 mmol; 476 mg) was dissolved in n-butanol (20 ml) at 90-95° C. with stirring before a solution of (4,6-Dioxo-3a,4,6,6a-tetrahydro-thieno[2,3-c]pyrrol-5-yl)-acetic acid methyl ester (10 mmol; 2.25 g) in hot n-butanol (20 ml) was added with stirring. Stirring was then continued at 95-100° C. for 1 h before the reaction mixture was allowed to cool to 60° C. with stirring. Subsequently, $H_2O$ (10 ml) and 6 N HCl (3.5 ml) were added with stirring. The mixture was stirred vigorously for 30 min before it was submitted to vacuum filtration. The filter cake was washed thoroughly with $H_2O$ (500 ml) and was dried in vacuo at 80° C. to give a tan solid (1.736 g). 1.70 g of this mixture were purified by flash column chromatography on silca gel eluting with $CH_2Cl_2$:EtOAc=9:1. Concentration of the first major fraction yielded A (645 mg). $^1$H NMR ($CDCl_3$, 200 MHz): δ=10.29 (br. s, 1H), 8.72 (br. s, 1H), 7.77 (d, 1H), 7.59 (d, 1H), 4.41 (t, 2H), 1.82 (m, 2H), 1.47 (m, 2H), 1.00 (t, 3H). Concentration of the last major fraction yielded B (84 mg). $^1$H NMR ($CDCl_3$, 200 MHz): δ=7.73 (d, 1H), 7.62 (d, 1H), 4.41 (t, 2H), 1.79 (m, 2H), 1.47 (m, 2H), 0.99 (t, 3H). The separation of the regioisomers A and B was not complete. A regioisomeric mixture (729 mg; A:B=ca. 1:6) was isolated by concentration of the mixed fractions.

d) 7-Chloro-4-hydroxy-thieno[2,3-c]pyridine-5-carboxylic acid butyl ester

A mixture of 4,7-dihydroxy-thieno[2,3-c]pyridine-5-carboxylic acid butyl ester (267 mg, 1 mmol), $POCl_3$ (217 mg, 1.4 mmol), and toluene (4 ml) was heated in a microwave oven at 140° C. for 15 min. The same procedure was repeated with a second batch. Both batches were combined, conc. aqueous $NaHCO_3$ (40 ml) and EtOAc (40 ml) were added and the mixture was stirred vigorously for 45 min. The organic layer was then separated, dried over $MgSO_4$ and concentrated in vacuo to give a tan solid (410 mg). Purification by flash column chromatography on silica gel using $CH_2Cl_2$:EtOAc=9:1 as the eluent yielded the title compound as a tan solid (297 mg, first major fraction). MS-(−)-ion: M−1=284.3.

e) [(7-Chloro-4-hydroxy-thieno[2,3-c]pyridine-5-carbonyl)-amino]-acetic acid

A mixture of 7-chloro-4-hydroxy-thieno[2,3-c]pyridine-5-carboxylic acid butyl ester (143 mg, 0.5 mmol), glycine (751 mg, 10 mmol), and a 0.5 M solution of MeONa in methanol (20 ml, 10 mmol) was refluxed with stirring for 24 h before it was concentrated in vacuo. To the residue was added $H_2O$ (10 ml) and the pH of the mixture was adjusted to 1 to 2 by addition of 6 N HCl. The resulting suspension was extracted with EtOAc (1×25 ml). The organic phase was dried over $MgSO_4$ and concentrated in vacuo to give the title compound as a tan solid (138 mg). MS-(−)-ion: M−1=285.0.

Example 42

[(4-Chloro-7-hydroxy-thieno[3,2-c]pyridine-6-carbonyl)-amino]-acetic acid a) 4-Chloro-7-hydroxy-thieno[3,2-c]pyridine-6-carboxylic acid butyl ester The title compound was obtained from 4,7-dihydroxy-thieno[3,2-c]pyridine-6-carboxylic acid butyl ester (example 41 c) in analogy to example 41 d); MS-(−)-ion: M−1=284.4.

b) [(4-Chloro-7-hydroxy-thieno[3,2-c]pyridine-6-carbonyl)-amino]-acetic acid

The title compound was obtained from 4-chloro-7-hydroxy-thieno[3,2-c]pyridine-6-carboxylic acid butyl ester and glycine in analogy to example 41 e); MS-(−)-ion: M−1=285.1.

Example 43

[(7-Bromo-4-hydroxy-thieno[2,3-c]pyridine-5-carbonyl)-amino]-acetic acid a) 7-Bromo-4-hydroxy-thieno[2,3-c]pyridine-5-carboxylic acid butyl ester The title compound was obtained from 4,7-dihydroxy-thieno[2,3-c]pyridine-5-carboxylic acid butyl ester (example 41 c) and POBr$_3$ in analogy to example 41 d); MS-(+)-ion: MS-(+)-ion: M+1=330.3 ($^{79}$Br), 331.9 ($^{81}$Br).

b) [(7-Bromo-4-hydroxy-thieno[2,3-c]pyridine-5-carbonyl)-amino]-acetic acid

The title compound was obtained from 7-bromo-4-hydroxy-thieno[2,3-c]pyridine-5-carboxylic acid butyl ester and glycine in analogy to example 41 e); MS-(+)-ion: M+1=331.5 ($^{79}$Br), 333.3 ($^{81}$Br).

Example 44

[(4-Bromo-7-hydroxy-thieno[3,2-c]pyridine-6-carbonyl)-amino]-acetic acid a) 4-Bromo-7-hydroxy-thieno[3,2-c]pyridine-6-carboxylic acid butyl ester The title compound was obtained from 4,7-dihydroxy-thieno[3,2-c]pyridine-6-carboxylic acid butyl ester (example 41 c) and POBr$_3$ in analogy to example 41 d); MS-(+)-ion: MS-(+)-ion: M+1=330.3 ($^{79}$Br), 331.9 ($^{81}$Br).

b) [(4-Bromo-7-hydroxy-thieno[3,2-c]pyridine-6-carbonyl)-amino]-acetic acid

The title compound was obtained from 4-bromo-7-hydroxy-thieno[3,2-c]pyridine-6-carboxylic acid butyl ester and glycine in analogy to example 41 e); MS-(+)-ion: M+1=331.5 ($^{79}$Br), 333.3 ($^{81}$Br).

Example 45

[(4-Hydroxy-7-phenyl-thieno[2,3-c]pyridine-5-carbonyl)-amino]-acetic acid a) 4-Hydroxy-7-phenyl-thieno[2,3-c]pyridine-5-carboxylic acid butyl ester A mixture of 7-bromo-4-hydroxy-thieno[2,3-c]pyridine-5-carboxylic acid butyl ester (example 43 a, 165 mg, 0.5 mmol), phenylboronic acid (94 mg, 0.75 mmol), tetrakis (triphenylphosphine) palladium(0) (59 mg, 0.05 mmol), potassium carbonate (208 mg, 1.5 mmol), and anhydrous 1.4-dioxane (3 ml) was heated in a microwave oven at 140° C. for 15 min. Then silica gel was added and the mixture concentrated in vacuo. The residue was added on top of a short column filled with silica gel. Elution with ethyl acetate:hexanes=9:1 and in vacuo concentration gave the title compound as a yellowish oil (95 mg); MS-(+)-ion: MS-(+)-ion: M+1=328.0.

b) [(4-Hydroxy-7-phenyl-thieno[2,3-c]pyridine-5-carbonyl)-amino]-acetic acid

The title compound was obtained from 4-hydroxy-7-phenyl-thieno[2,3-c]pyridine-5-carboxylic acid butyl ester and glycine in analogy to example 41 e); MS-(+)-ion: M+1=329.0.

Example 46

[(7-Hydroxy-4-phenyl-thieno[3,2-c]pyridine-6-carbonyl)-amino]-acetic acid a) 7-Hydroxy-4-phenyl-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) in analogy to example 45 a); MS-(+)-ion: MS-(+)-ion: M+1=328.4.

b) {[7-Hydroxy-4-phenyl-thieno[3,2-c]pyridine-6-carbonyl]-amino}-acetic acid

The title compound was obtained from 7-hydroxy-4-phenyl-thieno[3,2-c]pyridine-6-carboxylic acid butyl ester and glycine in analogy to example 41 e); MS-(+)-ion: M+1=329.2.

Example 47

{[7-(4-Fluoro-phenyl)-4-hydroxy-thieno[2,3-c]pyridine-5-carbonyl]-amino}-acetic acid a) 7-(4-Fluoro-phenyl)-4-hydroxy-thieno[2,3-c]pyridine-5-carboxylic acid butyl ester The title compound was obtained from 7-bromo-4-hydroxy-thieno[2,3-c]pyridine-5-carboxylic acid butyl ester (example 43 a) and 4-fluorophenylboronic acid in analogy to example 45 a); MS-(+)-ion: MS-(+)-ion: M+1=346.2.

b) {[7-(4-Fluoro-phenyl)-4-hydroxy-thieno[2,3-c]pyridine-5-carbonyl]-amino}-acetic acid The title compound was obtained from 7-(4-fluoro-phenyl)-4-hydroxy-thieno[2,3-c]pyridine-5-carboxylic acid butyl ester and glycine in analogy to example 41 e); MS-(−)-ion: M−1=345.3.

Example 48

{[4-(4-Fluoro-phenyl)-7-hydroxy-thieno[3,2-c]pyridine-6-carbonyl]-amino}-acetic acid a) 4-(4-Fluoro-phenyl)-7-hydroxy-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) and 4-fluorophenylboronic acid in analogy to example 45 a); MS-(+)-ion: MS-(+)-ion: M+1=346.2.

b) {[4-(4-Fluoro-phenyl)-7-hydroxy-thieno[3,2-c]
pyridine-6-carbonyl]-amino}-acetic acid The title compound was obtained from 4-(4-fluoro-phenyl)-7-hydroxy-thieno[3,2-c]pyridine-6-carboxylic acid butyl ester and glycine in analogy to example 41 e); MS-(−)-ion: M−1=345.1.

Example 49

[(7-Furan-2-yl-4-hydroxy-thieno[2,3-c]pyridine-5-carbonyl)-amino]-acetic acid a) 7-Furan-2-yl-4-hydroxy-thieno[2,3-c]pyridine-5-carboxylic acid butyl ester The title compound was obtained from 7-bromo-4-hydroxy-thieno[2,3-c]pyridine-5-carboxylic acid butyl ester (example 43 a) and 2-furanboronic acid in analogy to example 45 a); MS-(+)-ion: MS-(+)-ion: M+1=318.0.

b) [(7-Furan-2-yl-4-hydroxy-thieno[2,3-c]pyridine-5-carbonyl)-amino]-acetic acid The title compound was obtained from 7-furan-2-yl-4-hydroxy-thieno[2,3-c]pyridine-5-carboxylic acid butyl ester and glycine in analogy to example 41 e); MS-(−)-ion: M−1=317.0.

Example 50

[(4-Furan-2-yl-7-hydroxy-thieno[3,2-c]pyridine-6-carbonyl)-amino]-acetic acid a) 4-Furan-2-yl-7-hydroxy-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) and 2-furanboronic acid in analogy to example 45 a); MS-(+)-ion: MS-(+)-ion: M+1=318.0.

b) [(4-Furan-2-yl-7-hydroxy-thieno[3,2-c]pyridine-6-carbonyl)-amino]-acetic acid The title compound was obtained from 4-furan-2-yl-7-hydroxy-thieno[3,2-c]pyridine-6-carboxylic acid butyl ester and glycine in analogy to example 41 e); MS-(+)-ion: M+1=318.9.

Example 51

[(7-Furan-3-yl-4-hydroxy-thieno[2,3-c]pyridine-5-carbonyl)-amino]-acetic acid a) 7-Furan-3-yl-4-hydroxy-thieno[2,3-c]pyridine-5-carboxylic acid butyl ester The title compound was obtained from 7-bromo-4-hydroxy-thieno[2,3-c]pyridine-5-carboxylic acid butyl ester (example 43 a) and 3-furanboronic acid in analogy to example 45 a); MS-(+)-ion: MS-(+)-ion: M+1=317.9.

b) [(7-Furan-3-yl-4-hydroxy-thieno[2,3-c]pyridine-5-carbonyl)-amino]-acetic acid The title compound was obtained from 7-furan-3-yl-4-hydroxy-thieno[2,3-c]pyridine-5-carboxylic acid butyl ester and glycine in analogy to example 41 e); MS-(+)-ion: M+1=318.9.

Example 52

[(4-Furan-3-yl-7-hydroxy-thieno[3,2-c]pyridine-6-carbonyl)-amino]-acetic acid a) 4-Furan-3-yl-7-hydroxy-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) and 3-furanboronic acid in analogy to example 45 a); MS-(+)-ion: MS-(+)-ion: M+1=317.9 b) [(4-Furan-3-yl-7-hydroxy-thieno[3,2-c]pyridine-6-carbonyl)-amino]-acetic acid The title compound was obtained from 4-furan-3-yl-7-hydroxy-thieno[3,2-c]pyridine-6-carboxylic acid butyl ester and glycine in analogy to example 41 e); MS-(+)-ion: M+1=318.9.

Example 53

[(4-Hydroxy-7-thiophen-2-yl-thieno[2,3-c]pyridine-5-carbonyl)-amino]-acetic acid a) 4-Hydroxy-7-thiophen-2-yl-thieno[2,3-c]pyridine-5-carboxylic acid butyl ester The title compound was obtained from 7-bromo-4-hydroxy-thieno[2,3-c]pyridine-5-carboxylic acid butyl ester (example 43 a) and 2-thiopheneboronic acid in analogy to example 45 a); MS-(+)-ion: MS-(+)-ion: M+1=333.9.

b) [(4-Hydroxy-7-thiophen-2-yl-thieno[2,3-c]pyridine-5-carbonyl)-amino]-acetic acid The title compound was obtained from 4-hydroxy-7-thiophen-2-yl-thieno[2,3-c]pyridine-5-carboxylic acid butyl ester and glycine in analogy to example 41 e); MS-(−)-ion: M−1=333.0.

Example 54

[(7-Hydroxy-4-thiophen-2-yl-thieno[3,2-c]pyridine-6-carbonyl)-amino]-acetic acid a) 7-Hydroxy-4-thiophen-2-yl-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) and 2-thiopheneboronic acid in analogy to example 45 a); MS-(+)-ion: MS-(+)-ion: M+1=333.9.

b) [(7-Hydroxy-4-thiophen-2-yl-thieno[3,2-c]pyridine-6-carbonyl)-amino]-acetic acid The title compound was obtained from 7-hydroxy-4-thiophen-2-yl-thieno[3,2-c]pyridine-6-carboxylic acid butyl ester and glycine in analogy to example 41 e); MS-(+)-ion: M+1=334.9.

Example 55

[(4-Hydroxy-7-thiophen-3-yl-thieno[2,3-c]pyridine-5-carbonyl)-amino]-acetic acid a) 4-Hydroxy-7-thiophen-3-yl-thieno[2,3-c]pyridine-5-carboxylic acid butyl ester The title compound was obtained from 7-bromo-4-hydroxy-thieno[2,3-c]pyridine-5-carboxylic acid butyl ester (example 43 a) and 3-thiopheneboronic acid in analogy to example 45 a); MS-(+)-ion: MS-(+)-ion: M+1=333.9.

b) [(4-Hydroxy-7-thiophen-3-yl-thieno[2,3-c]pyridine-5-carbonyl)-amino]-acetic acid The title compound was obtained from 4-hydroxy-7-thiophen-3-yl-thieno[2,3-c]pyridine-5-carboxylic acid butyl ester and glycine in analogy to example 41 e); MS-(+)-ion: M+1=334.9.

Example 56

[(7-Hydroxy-4-thiophen-3-yl-thieno[3,2-c]pyridine-6-carbonyl)-amino]-acetic acid a) 7-Hydroxy-4-thiophen-3-yl-thieno[3,2-c]pyridine-6-carboxylic acid butyl ester The title compound was obtained from 4-bromo-7-hydroxy-thieno[3,2-c]pyridine-6-carboxylic acid butyl ester (example 44 a) and 3-thiopheneboronic acid in analogy to example 45 a); MS-(+)-ion: MS-(+)-ion: M+1=333.9.

b) [(7-Hydroxy-4-thiophen-3-yl-thieno[3,2-c]pyridine-6-carbonyl)-amino]-acetic acid The title compound was obtained from 7-hydroxy-4-thiophen-3-yl-thieno[3,2-c]pyridine-6-carboxylic acid butyl ester and glycine in analogy to example 41 e); MS-(+)-ion: M+1=334.9.

Example 57

[(4-Hydroxy-7-methyl-thieno[2,3-c]pyridine-5-carbonyl)-amino]-acetic acid a) 4-Hydroxy-7-methyl-thieno[2,3-c]pyridine-5-carboxylic acid butyl ester

A mixture of 7-bromo-4-hydroxy-thieno[2,3-c]pyridine-5-carboxylic acid butyl ester (example 43 a, 165 mg, 0.5 mmol), trimethylboroxine (70 µl, 0.5 mmol), tetrakis(triphenylphosphine) palladium(0) (118 mg, 0.1 mmol), potassium carbonate (208 mg, 1.5 mmol), and anhydrous 1.4-dioxane (3 ml) was heated in a microwave oven at 140° C. for 15 min. Then silica gel was added and the mixture concentrated in vacuo. The residue was added on top of a short column filled with silica gel. Elution with ethyl acetate:hexanes=9:1 and in vacuo concentration gave the title compound as a yellowish oil; MS-(+)-ion: MS-(+)-ion: M+1=266.0.

b) [(4-Hydroxy-7-methyl-thieno[2,3-c]pyridine-5-carbonyl)-amino]-acetic acid The title compound was obtained from 4-hydroxy-7-methyl-thieno[2,3-c]pyridine-5-carboxylic acid butyl ester and glycine in analogy to example 41 e); MS-(+)-ion: M+1=267.1.

Example 58

[(7-Hydroxy-4-methyl-thieno[3,2-c]pyridine-6-carbonyl)-amino]-acetic acid a) 7-Hydroxy-4-methyl-thieno[3,2-c]pyridine-6-carboxylic acid butyl ester

The title compound was obtained from 4-bromo-7-hydroxy-thieno[3,2-c]pyridine-6-carboxylic acid butyl ester (example 44 a) in analogy to example 57 a); MS-(+)-ion: MS-(+)-ion: M+1=265.9.

b) [(7-Hydroxy-4-methyl-thieno[3,2-c]pyridine-6-carbonyl)-amino]-acetic acid The title compound was obtained from 7-hydroxy-4-methyl-thieno[3,2-c]pyridine-6-carboxylic acid butyl ester and glycine in analogy to example 41 e); MS-(+)-ion: M+1=267.0.

Example 59

[(7-Ethynyl-4-hydroxy-thieno[2,3-c]pyridine-5-carbonyl)-amino]-acetic acid a) 4-Hydroxy-7-trimethylsilanylethynyl-thieno[2,3-c]pyridine-5-carboxylic acid butyl ester A mixture of 7-bromo-4-hydroxy-thieno[2,3-c]pyridine-5-carboxylic acid butyl ester (example 43 a, 165 mg, 0.5 mmol), ethynyl-trimethyl-silane (87 µl, 0.6 mmol), dichlorobis(triphenylphosphine)palladium(II) (11 mg, 0.015 mmol), CuI (5 mg, 0.025 mmol), and triethylamine (1.5 ml) was heated in a microwave oven at 100° C. with stirring for 15 min. After cooling to ambient temperature water (20 ml) was added and the mixture was extracted with diethylether (1×30 ml). The organic phase was dried over $MgSO_4$. Then silica gel was added and the mixture concentrated in vacuo. The residue was added on top of a short column filled with silica gel. Elution with ethyl acetate:hexanes=9:1 and in vacuo concentration gave the title compound as a dark oil (75 mg); MS-(+)-ion: MS-(+)-ion: M+1=348.4.

b) [(7-Ethynyl-4-hydroxy-thieno[2,3-c]pyridine-5-carbonyl)-amino]-acetic acid A mixture of 4-hydroxy-7-trimethylsilanylethynyl-thieno[2,3-c]pyridine-5-carboxylic acid butyl ester (70 mg, 0.2 mmol) and a 0.5 M solution of sodium methoxide in methanol (10 ml, 5 mmol) was refluxed with stirring for 1 h before glycine (375 mg, 5 mmol) was added. Refluxing and stirring was continued for 18 h before the mixture was concentrated in vacuo. The residue was dissolved in water (20 ml), and the pH of the solution was adjusted to 2-3 by addition of 6 N aqueous HCl. The resulting suspension was extracted with ethyl acetate (1×20 ml). The organic phase was dried over MgSO$_4$ and concentrated in vacuo to give the title compound as a tan solid (56 mg); MS-(+)-ion: M+1=277.1.

Example 60

[(4-Ethynyl-7-hydroxy-thieno[3,2-c]pyridine-6-carbonyl)-amino]-acetic acid a) 4-Ethynyl-7-hydroxy-thieno[3,2-c]pyridine-6-carboxylic acid butyl ester A mixture of 4-bromo-7-hydroxy-thieno[3,2-c]pyridine-6-carboxylic acid butyl ester (example 44 a, 165 mg, 0.5 mmol), ethynyl-trimethyl-silane (87 μl, 0.6 mmol), dichlorobis(triphenylphosphine)palladium(II) (11 mg, 0.015 mmol), CuI (5 mg, 0.025 mmol), and triethylamine (1.5 ml) was heated in a microwave oven at 100° C. with stirring for 15 min. After cooling to ambient temperature water (20 ml) was added and the mixture was extracted with diethylether (1×30 ml). The organic phase was dried over MgSO$_4$. Then silica gel was added and the mixture concentrated in vacuo. The residue was added on top of a short column filled with silica gel. Elution with ethyl acetate:hexanes=9:1 and in vacuo concentration gave the title compound as a dark oil (30 mg); MS-(+)-ion: MS-(+)-ion: M+1=275.9.

b) [(4-Ethynyl-7-hydroxy-thieno[3,2-c]pyridine-6-carbonyl)-amino]-acetic acid

The title compound was obtained from 4-ethynyl-7-hydroxy-thieno[3,2-c]pyridine-6-carboxylic acid butyl ester and glycine in analogy to example 41 e); MS-(+)-ion: M+1=276.9.

Example 61

[(7-Cyano-4-hydroxy-thieno[2,3-c]pyridine-5-carbonyl)-amino]-acetic acid a) 7-Cyano-4-hydroxy-thieno[2,3-c]pyridine-5-carboxylic acid butyl ester A mixture of 7-bromo-4-hydroxy-thieno[2,3-c]pyridine-5-carboxylic acid butyl ester (example 43 a, 165 mg, 0.5 mmol), CuCN (91 mg, 1 mmol), and dimethylformamide (2 ml) was heated in a microwave oven at 160° C. with stirring for 15 min. After cooling to ambient temperature water (20 ml) was added and the mixture was extracted with ethyl acetate (1×60 ml). The resulting mixture was filtered through a pad of celite. The organic phase was washed with water (2×25 ml), dried over MgSO$_4$, and concentrated in vacuo to give the title compound as tan solid (72 mg); MS-(−)-ion: MS-(−)-ion: M−1=275.1.

b) [(7-Cyano-4-hydroxy-thieno[2,3-c]pyridine-5-carbonyl)-amino]-acetic acid

The title compound was obtained from 7-cyano-4-hydroxy-thieno[2,3-c]pyridine-5-carboxylic acid butyl ester and glycine in analogy to example 41 e)-; MS-(−)-ion: M−1=276.1.

Example 62

[(4-Cyano-7-hydroxy-thieno[3,2-c]pyridine-6-carbonyl)-amino]-acetic acid a) 4-Cyano-7-hydroxy-thieno[3,2-c]pyridine-6-carboxylic acid butyl ester A mixture of 4-bromo-7-hydroxy-thieno[3,2-c]pyridine-6-carboxylic acid butyl ester (example 44 a, 165 mg, 0.5 mmol), CuCN (181 mg, 2 mmol), tris(dibenzylideneacetone)dipalladium(0) (46 mg, 0.05 mmol), 1,1'-bis(diphenylphosphino)ferrocene (114 mg, 0.2 mmol), tetraethylammonium cyanide (83 mg, 0.5 mmol), and anhydrous 1.4-dioxane (3 ml) was heated in a microwave oven at 140° C. with stirring for 15 min. Then silica gel was added and the mixture concentrated in vacuo. The residue was added on top of a short column filled with silica gel. Elution with ethyl acetate:hexanes=1:1 and in vacuo concentration gave a tan solid (209 mg). Purification by flash column chromatography on silica gel using ethyl acetate:hexanes=3:7 and then 1:1 gave the title compound as a tan solid (63 mg); MS-(+)-ion: MS-(−)-ion: M−1=275.1.

b) [(4-Cyano-7-hydroxy-thieno[3,2-c]pyridine-6-carbonyl)-amino]-acetic acid

The title compound was obtained from 4-cyano-7-hydroxy-thieno[3,2-c]pyridine-6-carboxylic acid butyl ester and glycine in analogy to example 41 e); MS-(−)-ion: M−1=276.0.

We claim:
1. A compound of formula Ia:

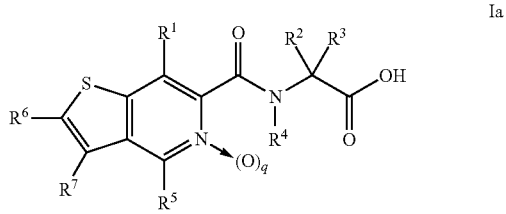

wherein
q is 0 or 1;
$R^1$ is selected from the group consisting of hydroxy, alkoxy, substituted alkoxy, acyloxy, cycloalkoxy, substituted cycloalkoxy, aryloxy, substituted aryloxy, mercapto, thioether, amino, substituted amino, and aminoacyl;
$R^2$ is selected from the group consisting of hydrogen, deuterium, and methyl;
$R^3$ is selected from the group consisting of hydrogen, deuterium, alkyl, and $R^{101}$;
$R^4$ is selected from the group consisting of hydrogen, alkyl, and $R^{101}$;
$R^5$ is selected from the group consisting of hydrogen, halo, alkyl, $R^{101}$, alkenyl, $R^{111}$, alkynyl, $R^{113}$ alkoxy, substituted alkoxy, cycloalkyl, $R^{103}$, cycloalkoxy, substituted cycloalkoxy, amino, substituted amino, aminoacyl, aryl, $R^{105}$, aryloxy, substituted aryloxy, furanyl, thienyl, thioether, cyano, and acyl; and
$R^6$ and $R^7$ are independently selected from the group consisting of hydrogen, hydroxy, cyano, halo, nitro, acyl, amino, substituted amino, acylamino, sulfonyl, alkyl, $R^{101}$, alkenyl, $R^{111}$, alkynyl, $R^{113}$ alkoxy, substituted alkoxy, aryl, $R^{105}$, aryloxy, substituted aryloxy, thioether, arylthio, and substituted arylthio;

or a pharmaceutically acceptable salt, single stereoisomer, or mixture of stereoisomers thereof, or an ester or amide of the —COOH group on the glycine- or alanine-based substituent of the thienopyridine ring, which ester is selected from —C(O)O-alkyl, —C(O)O—$R^{101}$, —C(O)O-alkenyl, —C(O)O—$R^{111}$, —C(O)O-alkynyl, —C(O)O—$R^{113}$, —C(O)O-aryl, and —C(O)O—$R^{105}$; and the amide is derived from amines of the formula $HNR^{20}R^{21}$, where $R^{20}$ and $R^{21}$ are independently hydrogen, alkyl, $R^{101}$, aryl, or $R^{105}$; and further wherein $R^{101}$ is substituted alkyl, wherein substituted alkyl is alkyl having from 1 to 5 substituents selected from the group consisting of $R^{200}$, $R^{201}$, $R^{202}$, and $R^{203}$;

$R^{103}$ is substituted cycloalkyl, wherein substituted cycloalkyl is cycloalkyl having from 3 to 10 carbon atoms having single or multiple cyclic rings and from 1 to 5 substituents selected from the group consisting of oxo (=O), thioxo (=S), alkyl, $R^{101}$, and $R^{201}$;

$R^{105}$ is substituted aryl, wherein substituted aryl is aryl having from 1 to 4 substituents selected from the group consisting of $R^{201}$, alkyl, $R^{101}$, alkenyl, $R^{111}$, alkynyl, $R^{113}$, $R^{202}$, $R^{203}$, amidino, aminocarbonyloxy, aminocarbonylamino, aminothiocarbonylamino, cycloalkoxy, substituted cycloalkoxy, thiol, alkylthio, substituted alkylthio, arylthio, substituted arylthio, cycloalkylthio, substituted cycloalkylthio, guanidino, oxycarbonylamino, oxythiocarbonylamino, —S(O)$_2$-alkyl, —S(O)$_2$—$R^{101}$, —S(O)$_2$-cycloalkyl, —S(O)$_2$—$R^{103}$, —S(O)$_2$-alkenyl, —S(O)$_2$—$R^{111}$, —S(O)$_2$-aryl, and —S(O)$_2$—$R^{105}$;

$R^{111}$ is substituted alkenyl, wherein substituted alkenyl is alkenyl having from 1 to 3 $R^{201}$;

$R^{113}$ is substituted alkynyl, wherein substituted alkynyl is alkynyl having from 1 to 3 $R^{201}$;

$R^{200}$ is aminocarbonylamino, aminothiocarbonylamino, aminocarbonyloxy, aryloxyaryl, substituted aryloxyaryl, oxo, thioxo, thiol, alkylthio, substituted alkylthio, arylthio, substituted arylthio, cycloalkylthio, substituted cycloalkylthio, cycloalkoxy, substituted cycloalkoxy, oxycarbonylamino, and oxythiocarbonylamino;

$R^{201}$ is alkoxy, substituted alkoxy, acyl, acylamino, acyloxy, amino, substituted amino, aminoacyl, aryloxy, substituted aryloxy, cyano, halogen, hydroxyl, nitro, carboxyl, carboxyl esters, cycloalkyl, $R^{103}$, aryl, and $R^{105}$;

$R^{202}$ is —NR$^{40}$S(O)$_2$-alkyl, —NR$^{40}$S(O)$_2$—$R^{101}$, —NR$^{40}$S(O)$_2$-aryl, —NR$^{40}$S(O)$_2$—$R^{105}$, —NR$^{40}$S(O)$_2$—NR$^{40}$-alkyl, —NR$^{40}$S(O)$_2$—NR$^{40}$—$R^{101}$, —NR$^{40}$S(O)$_2$—NR$^{40}$-aryl, and —NR$^{40}$S(O)$_2$—NR$^{40}$—$R^{105}$, where each $R^{40}$ is hydrogen or alkyl; and $R^{203}$ is —OS(O)$_2$-alkyl, —OS(O)$_2$—$R^{101}$, —OS(O)$_2$-aryl, —OS(O)$_2$—$R^{105}$, and —OSO$_2$—NR$^{40}$R$^{40}$ where each $R^{40}$ is hydrogen or alkyl;

and further wherein substituted alkoxy is —O—$R^{101}$;
substituted cycloalkoxy is —O—$R^{103}$;
substituted aryloxy is —O—$R^{105}$;
substituted amino is —NR$^{41}$R$^{41}$, where each $R^{41}$ group is independently selected from the group consisting of hydrogen, alkyl, $R^{101}$, alkenyl, $R^{111}$, alkynyl, $R^{113}$, cycloalkyl, $R^{103}$, aryl, $R^{105}$, —S(O)$_2$-alkyl, —S(O)$_2$—$R^{101}$, —S(O)$_2$-cycloalkyl, —S(O)$_2$—$R^{103}$, —S(O)$_2$-alkenyl, —S(O)$_2$—$R^{111}$, —S(O)$_2$-aryl, and —S(O)$_2$—$R^{105}$, provided that both $R^{41}$ groups are not hydrogen;

substituted alkylthio is —S—$R^{101}$;
substituted arylthio is —S—$R^{105}$;
substituted cycloalkylthio is —S—$R^{103}$;
substituted aryloxyaryl is aryl-O-aryl, wherein each aryl group is substituted on either or both aryl rings with from 1 to 3 substituents selected from the group consisting of $R^{201}$, alkyl, $R^{101}$, alkenyl, $R^{111}$, alkynyl, $R^{113}$, $R^{202}$, $R^{203}$, amidino, aminocarbonyloxy, aminocarbonylamino, aminothiocarbonylamino, cycloalkoxy, substituted cycloalkoxy, thiol, alkylthio, substituted alkylthio, arylthio, substituted arylthio, cycloalkylthio, substituted cycloalkylthio, guanidino, oxycarbonylamino, oxythiocarbonylamino, —S(O)$_2$-alkyl, —S(O)$_2$—$R^{101}$, —S(O)$_2$-cycloalkyl, —S(O)$_2$—$R^{103}$, —S(O)$_2$-alkenyl, —S(O)$_2$—$R^{111}$, —S(O)$_2$-aryl, and —S(O)$_2$—$R^{105}$; and acyl is H—C(O)—, alkyl-C(O)—, $R^{101}$—C(O)—, alkenyl-C(O)—, $R^{111}$—C(O)—, alkynyl-C(O)—, $R^{113}$—C(O)—, cycloalkyl-C(O)—, $R^{103}$—C(O)—, aryl-C(O)—, or $R^{105}$—C(O)—.

2. The compound of claim 1, wherein q is 0.

3. The compound of claim 1, wherein $R^1$ is hydroxy.

4. The compound of claim 3, wherein $R^2$, $R^3$, and $R^4$ are all hydrogen.

5. The compound of claim 1, wherein $R^5$ is selected from the group consisting of hydrogen, alkyl, halo, aryl, $R^{105}$, cyano, alkynyl, furanyl, and thienyl.

6. The compound of claim 5, wherein $R^5$ is selected from the group consisting of hydrogen, methyl, bromo, chloro, phenyl, fluorophenyl, cyano, ethynyl, furanyl, and thienyl.

7. The compound of claim 1, wherein $R^6$ is selected from the group consisting of hydrogen, halo, alkyl, $R^{101}$, alkenyl, $R^{111}$, aryl, $R^{105}$, aryloxy, arylthio, and cyano.

8. The compound of claim 7, wherein $R^6$ is selected from the group consisting of hydrogen, bromo, methyl, phenyl, trifluoromethylphenyl, phenoxyphenyl, fluorophenyl, phenylsulfanyl, phenethyl, phenylethenyl, phenoxy, and cyano.

9. The compound of claim 1, wherein $R^7$ is selected from the group consisting of hydrogen, aryl, and $R^{105}$.

10. The compound of claim 1, wherein $R^7$ is selected from the group consisting of hydrogen, phenyl, and fluorophenyl.

11. The compound of claim 1, wherein $R^1$ is hydroxy;
$R^2$, $R^3$, and $R^4$ are hydrogen;
$R^5$ is hydrogen, halo, alkyl, or aryl;
$R^6$ is hydrogen, halo, alkyl, $R^{101}$, aryl, $R^{105}$, arylthio, alkenyl, $R^{111}$, or aryloxy; and
$R^7$ is hydrogen, aryl, or $R^{105}$;

or a pharmaceutically acceptable salt, single stereoisomer, or mixture of stereoisomers thereof, or an ester or amide of the —COOH group on the glycine- or alanine-based substituent of the thienopyridine ring, which ester is selected from —C(O)O-alkyl, —C(O)O—$R^{101}$, —C(O)O-alkenyl, —C(O)O—$R^{111}$, —C(O)O-alkynyl, —C(O)O—$R^{113}$, —C(O)O-aryl, and —C(O)O—$R^{105}$; and the amide is derived from amines of the formula $HNR^{20}R^{21}$, where $R^{20}$ and $R^{21}$ are independently hydrogen, alkyl, $R^{101}$, aryl, or $R^{105}$.

12. The compound of claim 1, wherein $R^1$ is hydroxy;
$R^2$, $R^3$, and $R^4$ are hydrogen;
$R^5$ is halo, alkyl, alkynyl, cyano, aryl, $R^{105}$, furanyl or thienyl;
$R^6$ is hydrogen, halo, alkyl, aryl, $R^{105}$ or cyano; and
$R^7$ is hydrogen, aryl, or $R^{105}$;

or a pharmaceutically acceptable salt, single stereoisomer, or mixture of stereoisomers thereof, or an ester or amide of the —COOH group on the glycine- or alanine-based substituent of the thienopyridine ring, which ester is selected from —C(O)O-alkyl, —C(O)O—$R^{101}$, —C(O)O-alkenyl, —C(O)O—$R^{111}$, —C(O)O-alkynyl, —C(O)O—$R^{113}$, —C(O)O-aryl, and —C(O)O—$R^{105}$; and the amide is derived from amines of the formula HN$R^{20}R^{21}$, where $R^{20}$ and $R^{21}$ are independently hydrogen, alkyl, $R^{101}$, aryl, or $R^{105}$.

13. A compound of claim 1, selected from the group consisting of:

[(2-Bromo-7-hydroxy-thieno[3,2-c]pyridine-6-carbonyl)-amino]-acetic acid;

{[7-Hydroxy-2-(4-methoxy-phenyl)-thieno[3,2-c]pyridine-6-carbonyl]-amino}-acetic acid;

[(7-Hydroxy-2,4-dimethyl-thieno[3,2-c]pyridine-6-carbonyl)-amino]-acetic acid;

{[7-Hydroxy-4-methyl-2-(4-phenoxy-phenyl)-thieno[3,2-c]pyridine-6-carbonyl]-amino}-acetic acid;

{[7-Hydroxy-2-(4-phenoxy-phenyl)-thieno[3,2-c]pyridine-6-carbonyl]-amino}-acetic acid;

[(7-Hydroxy-thieno[3,2-c]pyridine-6-carbonyl)-amino]-acetic acid;

[(2-Bromo-4-chloro-7-hydroxy-thieno[3,2-c]pyridine-6-carbonyl)-amino]-acetic acid;

[(2,4-Dibromo-7-hydroxy-thieno[3,2-c]pyridine-6-carbonyl)-amino]-acetic acid;

[(7-Hydroxy-2-phenylsulfanyl-thieno[3,2-c]pyridine-6-carbonyl)-amino]-acetic acid;

[(7-Hydroxy-2,4-diphenyl-thieno[3,2-c]pyridine-6-carbonyl)-amino]-acetic acid;

[(7-Hydroxy-2-styryl-thieno[3,2-c]pyridine-6-carbonyl)-amino]-acetic acid;

[(7-Hydroxy-2-phenoxy-thieno[3,2-c]pyridine-6-carbonyl)-amino]-acetic acid;

[(7-Hydroxy-2-phenethyl-thieno[3,2-c]pyridine-6-carbonyl)-amino]-acetic acid;

{[7-Hydroxy-2-(3-trifluoromethyl-phenyl)-thieno[3,2-c]pyridine-6-carbonyl]-amino}-acetic acid;

{[4-Bromo-7-hydroxy-2-(3-trifluoromethyl-phenyl)-thieno[3,2-c]pyridine-6-carbonyl]-amino}-acetic acid;

{[4-Cyano-7-hydroxy-2-(3-trifluoromethyl-phenyl)-thieno[3,2-c]pyridine-6-carbonyl]-amino}-acetic acid;

[(2-Cyano-7-hydroxy-thieno[3,2-c]pyridine-6-carbonyl)-amino]-acetic acid;

{[7-Hydroxy-2-(4-trifluoromethyl-phenyl)-thieno[3,2-c]pyridine-6-carbonyl]-amino}-acetic acid;

{[7-Hydroxy-2-(2-trifluoromethyl-phenyl)-thieno[3,2-c]pyridine-6-carbonyl]-amino}-acetic acid;

{[4-Bromo-3-(4-fluoro-phenyl)-7-hydroxy-thieno[3,2-c]pyridine-6-carbonyl]-amino}-acetic acid;

{[3-(4-Fluoro-phenyl)-7-hydro-thieno[3,2-c]pyridine-6-carbonyl]-amino}-acetic acid;

{[3-(4-Fluoro-phenyl)-7-hydroxy-4-methyl-thieno[3,2-c]pyridine-6-carbonyl]-amino}-acetic acid;

{[4-Cyano-3-(4-fluoro-phenyl)-7-hydroxy-thieno[3,2-c]pyridine-6-carbonyl]-amino}-acetic acid;

{[2-(4-fluoro-phenyl)-7-hydroxy-thieno[3,2-c]pyridine-6-carbonyl]-amino}-acetic acid;

{[2-(4-fluoro-phenyl)-7-hydroxy-4-methyl-thieno[3,2-c]pyridine-6-carbonyl]-amino}-acetic acid;

{[2,3-Bis-(4-fluoro-phenyl)-7-hydroxy-thieno[3,2-c]pyridine-6-carbonyl]-amino}-acetic acid;

[(4-Chloro-7-hydroxy-thieno[3,2-c]pyridine-6-carbonyl)-amino]-acetic acid;

[(4-Bromo-7-hydroxy-thieno[3,2-c]pyridine-6-carbonyl)-amino]-acetic acid;

[(7-Hydroxy-4-phenyl-thieno[3,2-c]pyridine-6-carbonyl)-amino]-acetic acid;

{[4-(4-Fluoro-phenyl)-7-hydroxy-thieno[3,2-c]pyridine-6-carbonyl]-amino}-acetic acid;

[(4-Furan-2-yl-7-hydroxy-thieno[3,2-c]pyridine-6-carbonyl)-amino]-acetic acid;

[(4-Furan-3-yl-7-hydroxy-thieno[3,2-c]pyridine-6-carbonyl)-amino]-acetic acid;

[(7-Hydroxy-4-thiophen-2-yl-thieno[3,2-c]pyridine-6-carbonyl)-amino]-acetic acid;

[(7-Hydroxy-4-thiophen-3-yl-thieno[3,2-c]pyridine-6-carbonyl)-amino]-acetic acid;

[(7-Hydroxy-4-methyl-thieno[3,2-c]pyridine-6-carbonyl)-amino]-acetic acid;

[(4-Ethynyl-7-hydroxy-thieno[3,2-c]pyridine-6-carbonyl)-amino]-acetic acid;

and

[(4-Cyano-7-hydroxy-thieno[3,2-c]pyridine-6-carbonyl)-amino]-acetic acid;

or a pharmaceutically acceptable salt, single stereoisomer, or mixture of stereoisomers thereof, or an ester or amide of the —COOH group on the glycine- or alanine-based substituent of the thienopyridine ring, which ester is selected from —C(O)O-alkyl, —C(O)O—$R^{101}$, —C(O)O-alkenyl, —C(O)O—$R^{111}$, —C(O)O-alkenyl, —C(O)O—$R^{113}$, —C(O)O-aryl, and —C(O)O—$R^{105}$; and the amide is derived from amines of the formula HN$R^{20}R^{21}$, where $R^{20}$ and $R^{21}$ are independently hydrogen, alkyl, $R^{101}$, aryl, or $R^{105}$.

14. A pharmaceutical composition comprising a pharmaceutically acceptable excipient or carrier, and a therapeutically effective amount of one or more compound as claimed in any one of claims 1, 12, and 13.

* * * * *

UNITED STATES PATENT AND TRADEMARK OFFICE
CERTIFICATE OF CORRECTION

| | | |
|---|---|---|
| PATENT NO. | : 8,703,795 B2 | Page 1 of 1 |
| APPLICATION NO. | : 11/367969 | |
| DATED | : April 22, 2014 | |
| INVENTOR(S) | : Turtle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2025 days.

Signed and Sealed this
Twentieth Day of October, 2015

Michelle K. Lee
*Director of the United States Patent and Trademark Office*